US006946261B1

(12) United States Patent
Burian et al.

(10) Patent No.: US 6,946,261 B1
(45) Date of Patent: Sep. 20, 2005

(54) EFFICIENT METHODS FOR PRODUCING ANTI-MICROBIAL CATIONIC PEPTIDES IN HOST CELLS

(75) Inventors: Jàn Burian, Victoria (CA); Daniel Bartfeld, Vancouver (CA)

(73) Assignee: Migenix Inc., Vancouver (CA)

( * ) Notice: Subject to any disclaimer, the term of this patent is extended or adjusted under 35 U.S.C. 154(b) by 0 days.

(21) Appl. No.: 09/444,281

(22) Filed: Nov. 19, 1999

Related U.S. Application Data
(60) Provisional application No. 60/109,218, filed on Nov. 20, 1998.

(51) Int. Cl.$^7$ .......................... C07K 1/00; C12N 15/63; C12N 1/21

(52) U.S. Cl. ................... 435/69.1; 435/320.1; 435/325; 435/252.3; 435/252.33; 514/12; 514/13; 530/300; 530/324; 536/23.1; 536/23.4

(58) Field of Search .............................. 435/69.1, 320.1, 435/325, 252.3, 252.33; 514/12, 13; 530/300, 324; 536/23.1, 23.4

(56) References Cited

U.S. PATENT DOCUMENTS

| | | | |
|---|---|---|---|
| 5,206,154 A | 4/1993 | Lai et al. ................... | 435/69.7 |
| 5,589,364 A | 12/1996 | Williams et al. ........... | 435/69.7 |
| 5,593,866 A | 1/1997 | Hancock et al. ........... | 435/69.7 |
| 5,851,802 A | 12/1998 | Better ....................... | 435/69.7 |
| 6,180,604 B1 | 1/2001 | Fraser et al. ................... | 514/12 |
| 6,183,992 B1 | 2/2001 | Kim et al. .................. | 435/69.7 |
| 6,191,254 B1 | 2/2001 | Falla et al. ................. | 530/300 |
| 6,242,219 B1 | 6/2001 | Better et al. ............... | 435/69.7 |
| 6,444,645 B1 * | 9/2002 | Selsted et al. ................. | 514/14 |
| 6,503,881 B2 | 1/2003 | Krieger et al. .................. | 514/2 |
| 6,538,106 B1 | 3/2003 | Fraser et al. ................ | 530/327 |

FOREIGN PATENT DOCUMENTS

| | | |
|---|---|---|
| EP | 0925308 | 6/1902 |
| WO | WO 95/09239 | 4/1995 |
| WO | WO 96/04373 | 2/1996 |
| WO | WO 96/28559 | 9/1996 |
| WO | WO 97/08199 | 3/1997 |
| WO | WO 98/07745 | 2/1998 |
| WO | WO 98/40401 | 9/1998 |
| WO | WO 98/54336 | 12/1998 |
| WO | WO 99/64611 | 12/1999 |
| WO | WO 00/55322 | 9/2000 |

OTHER PUBLICATIONS

Rosenburg, Protein Analysis and Purification: Benchtop Techniques, 1996, Birkhauser, Boston MA, pp. 184–185.*
Stratagene Product Catalog, 1993, pp 38, 44, and 48.*
Pharmacia Product Catalog, 1996, pp. 110 and 121–123.*
Molecular Cloning: A laboratory Manual, $2^{nd}$ ed., 1989, Sambrook et al., Cold Spring Harbor Press, pp. 1.14–1.15.*

Lee, Jae–Hyun et al., "Multimeric expression of the antimicrobial peptide buforin II in *Escherichia coli* by fusion to a cysteine–rich acidic peptide," *Journal of Microbiology and Biotechnology* 9(3):303–310, 1999.
Broekaert et al., "Plant Defensins: Novel Antimicrobial Peptides as Components of the Host Defense System," *Plant Physiology* 108(4): 1353–1358, Aug. 1995.
Ganz et al., "Defensins," *Pharmacology & Therapeutics* 66(2):191–205, 1995.
Martin et al., "Defensins and other endogenous peptide antibiotics of vertebrates," *Journal of Leukocyte Biology* 58(2): 128–136, Aug. 1995.
Hancock et al., "Cationic peptides: a new source of antibiotics," *Trends in Biotechnology* 16: 82–88, Feb. 1998.
Gough et al., "Antiendotoxin Activity of Cationic Peptide Antimicrobial Agents," *Infection and Immunity* 64(11): 4922–4927, Nov. 1996.
Steinberg et al., "Protegrin–1: a Broad–Spectrum, Rapidly Microbicidal Peptide with In Vivo Activity," *Antimicrobial Agents & Chemotherapy* 41(7): 1738–1742, Jul. 1997.
Ahmad et al., "Liposomal entrapment of the neutrophil–derived peptide indolicidin endows it with in vivo antifungal activity," *Biochimica et Biophysica Acta* 1237(1): 109–114, Jul. 6, 1995.
Piers et al., "Recombinant DNA procedures for producing small antimicrobial cationic peptides in bacteria," *Gene* 134: 7–13, 1993.
Reichhart et al., Expression and secretion in yeast of active insect defensin, an inducible antibacterial peptide from the fleshfly *Phormia terranovae*, *Invertebrate Reproduction & Development* 21(1): 15–24, Feb. 1992.
Hellers et al., "Expression and post–translational processing of preprocecropin A using a baculovirus vector," *European Journal of Biochemistry* 199(2): 435–439, Jul. 1991.
Sharma et al., "High–efficiency synthesis of human α–endorphin and magainin in the erythrocytes of transgenic mice: A production system for therapeutic peptides," *Proceedings of the National Academy of Sciences of the USA* 91: 9337–9341, Sep. 1994.
Callaway et al., "Modification of the C Terminus of Cecropin Is Essential for Broad–Spectrum Antimicrobial Activity," *Antimicrobial Agents & Chemotherapy* 37(8): 1614–1619, Aug. 1993.

(Continued)

*Primary Examiner*—Jon Weber
*Assistant Examiner*—Holly Schnizer
(74) *Attorney, Agent, or Firm*—Darby & Darby PC

(57) ABSTRACT

Endogenously produced cationic antimicrobial peptides are ubiquitous components of host defenses in mammals, birds, amphibia, insects, and plants. Cationic peptides are also effective when administered as therapeutic agents. A practical drawback in cationic peptide therapy, however, is the cost of producing the agents. The methods described herein provide a means to efficiently produce cationic peptides from recombinant host cells. These recombinantly-produced cationic peptides can be rapidly purified from host cell proteins using anion exchange chromatography.

29 Claims, 16 Drawing Sheets

OTHER PUBLICATIONS

Hara et al., Production in *Escherichia coli* of Moricin, a Novel Type Antibacterial Peptide from the Silkworm, *Bombyx mori*, *Biochemical And Biophysical Research Communications* 220(3): 664–669, Mar. 27, 1996.

Casteels–Josson et al., "Apidaecin multipeptide precursor structure: a putative mechanism for amplification of the insect antibacterial response," *The EMBO Journal* 12(4): 1569–4578 Apr. 1993.

Lee et al., "Acidic Peptide–Mediated Expression of the Antimicrobial Peptide Buforin II as Tandem Repeats in *Escherichia coli*," *Protein Expression and Purification* 12(1): 53–60, Feb. 1998.

Shen, "Multiple joined genes prevent product degradation in *Eschdrichia coli*," *Proceedings of the National Academy of Sciences of the USA* 81(15): 4627–4631, Aug. 1984.

Lennick et al., "High–level expression of α–human atrial natriuretic peptide from multiple joined genes in *Escherichia coli*," *Gene* 61(1): 103–112, 1987.

Kempe et al., "Multiple–copy genes: production and modification of monomeric peptides from large multimeric fusion proteins," *Gene* 39(2 and 3): 239–245, 1985.

Zhang et al., "Determinants of Recombinant Production of Antimicrobial Catiionic Peptides and Creation of Peptide Variants in Bacteria," *Biochemical and Biophysical Research Communications* 247: 674–680, 1998.

* cited by examiner

EFFICIENT METHODS FOR PRODUCING ANTI-MICROBIAL CATIONIC PEPTIDES IN HOST CELLS

CROSS-REFERENCE TO RELATED APPLICATIONS

This application claims priority from U.S. Provisional Application Ser. No. 60/109,218, filed Nov. 20, 1998, which application is incorporated by reference in its entirety.

TECHNICAL FIELD

The present invention relates generally to methods for obtaining recombinant peptides and proteins from host cells. In particular, the present invention relates to improved processes for producing and purifying cationic peptides from recombinant host cells in which the peptide is expressed in high yield and is easily recovered.

BACKGROUND OF THE INVENTION

Antimicrobial peptides, particularly cationic peptides have received increasing attention as a new pharmaceutical substance, because of their broad spectrum of antimicrobial activities and the rapid development of multi-drug-resistant pathogenic microorganisms. Endogenous peptide antibiotics are ubiquitous components of host defenses in mammals, birds, amphibia, insects, and plants. These endogenous antimicrobial peptides are usually cationic amphipathic molecules that contain 10 to 45 amino acid residues and an excess of lysine and arginine residues. (for a review, see Broekaert et al., *Plant Physiol.* 108:1353, 1995; Ganz and Lehrer, *Pharmacol. Ther.* 66:191, 1995; Martin et al., *J. Leukoc. Biol.* 58:128, 1995; Hancock and Lehrer, *TIBTECH* 16:82, 1998). Examples of cationic peptides include rabbit defensin, crab tachyplesin, bovine bactenecin, silk-moth cecropin A, frog magainins, and bovine indolicidin. The main site of action of the peptides is the cytoplasmic membrane of bacteria and other microbes. Due to their amphipathic nature, the peptides disrupt the membrane, causing a loss of potassium ions, membrane depolarization, and a decrease in cytoplasmic ATP.

Since their de novo synthesis or release from storage sites can be induced rapidly, cationic peptides are particularly important in the initial phases of resistance to microbial invasion. Cationic peptides are also effective when administered as therapeutic agents. In the treatment of topical infection, for example, an α-helical magainin variant peptide has been shown to be effective against polymicrobic foot ulcer infections in diabetics, and a protegrin-derived peptide was found useful for treatment of oral polymicrobic ulcers in cancer patients (Hancock and Lehrer, *TIBTECH* 16:82, 1998). Efficacy against systemic infection has been shown with an α-helical peptide used to treat *Pseudomonas aeruginosa* peritoneal infection, a β-sheet protegrin against methicillin-resistant *Staphylococcus aureus* and against vancomycin-resistant *Enterococcus faecalis*, and extended-helix indolicidin against *Aspergillus* fungal infections (Gough et al., *Infect. Immun.* 64:4922, 1996; Steinberg et al., *Antimicrob. Agents Chemother.* 41:1738, 1997; and Ahmad et al, *Biochim. Biophys. Acta* 1237:109, 1995). Therefore, naturally-occurring cationic peptides, and their synthetic variants, are valuable antimicrobial therapeutics.

A practical drawback in cationic peptide therapy is the lack of a cost effective, mass-production method of the agents. Typically, the isolation of cationic peptides from natural sources is not cost-effective, and does not apply to the production of engineered cationic peptide variants which may have increased efficacy. While chemical peptide synthesis can be used to manufacture either natural or engineered cationic peptides, this approach is very costly.

Therefore, alternate, more economical and efficient methods of synthesis are needed, such as in vivo synthesis in host cells using recombinant DNA methods. Researchers have attempted various methods for recombinant production of cationic peptides. For example, cationic peptides have been produced in bacteria, such as *E. coli* or *Staphylococcus aureus*, yeast, insect cells, and transgenic mammals (Piers et al., *Gene* 134:7, 1993, Reichhart et al., *Invertebrate Reprod. Develop.* 21:15, 1992, Hellers et at, *Eur. J. Biochem.* 199:435, 1991, and Sharma et al, *Proc. Nat'l Acad Sci. USA* 91:9337, 1994).

Much attention has focused on production in *E. coli*, since those versed in the art are familiar with the fact that high productivity can be obtained in *E. coli* using the recombinant DNA technology. However, for small peptides it is often necessary to produce them as part of a larger fusion protein. In this technique the gene for the peptide is joined to that of a larger carrier protein and the fusion expressed as a single larger protein. Following synthesis the peptide must be cleaved from the fusion partner. There is an extensive body of literature on protein fusion, especially in the gene expression host *E. coli*. For example, a number of recombinant proteins have been produced as fusion proteins in *E. coli*, such as, insulin A and B chain, calcitonin, Beta-globin, myoglobin, and a human growth hormone (Uhlen and Moks, "Gene Fusions for Purposes of Expression, An Introduction" in *Methods in Enzymology* 185:129–143 Academic Press, Inc. 1990). Nevertheless, recombinant gene expression from a host cell presents a number of technical problems, particularly if it is desired to produce large quantities of a particular protein. For example, if the protein is a cationic peptide, such peptides are very susceptible to proteolytic degradation, possibly due to their small size or lack of highly ordered tertiary structure. One approach to solving this problem is to produce recombinant cationic proteins in protease-deficient *E. coli* host cell strains (see, for example, Williams et al., U.S. Pat. No. 5,589,364, and WO 96/04373). Yet there is no general way to predict which protease-deficient strains will be effective for a particular recombinant protein.

In principle the recombinant DNA technique is straight forward. However, any sequence that interferes with bacterial growth through replication or production of products toxic to the bacteria, such as lytic cationic peptides, are problematic for cloning. Foreign peptide gene products that are unstable or toxic, like cationic peptides, can also be stabilized by expressing the peptides as part of a fusion protein comprising a host cell protein. For example, Callaway et al. et al., *Antimicrob. Agents Chemother.* 37:1614, 1993, expressed cecropin A in *E. coli* as a fusion peptide with a truncated portion of the L-ribulokinase gene product, Piers et al. et al., *Gene* 134:7, 1993, expressed fusion proteins in *E. coli* that comprised glutathione-S-transferase and either defensin (HNP-1) or a synthetic cecropin-melittin hybrid, while Hara et al., *Biochem. Biophys. Res. Commun.* 220:664, 1996, expressed silkworm moricin in *E. coli* as a fusion protein with a β-galactosidase or a maltose-binding protein moiety.

One of the better options to avoid the toxic effects of a bacteriolytic peptide on the host bacterial cells in highly efficient production, and to avoid proteolytic degradation of the peptides, is to utilize the intrinsic bacterial host mechanism of driving heterologous proteins into inclusion bodies as a denatured insoluble form.

The approach outlined above suffers from the inherent limitation on overall productivity imposed by the use of a small single peptide (circa 10%) in the large fusion protein.

Accordingly, a need exists for a means to efficiently produce cationic peptides from recombinant host cells.

SUMMARY OF THE INVENTION

The present invention provides compositions and methods for expressing large quantities of a selected polypeptide. Within one aspect of the invention, large quantities of a selected polypeptide can be expressed utilizing a multi-domain fusion protein expression cassette which comprises a promoter operably linked to a nucleic acid molecule which is expressed as an insoluble protein, wherein the nucleic acid molecule encodes a polypeptide comprising the structure (cationic peptide)-[(cleavage site)-(cationic peptide)]$_n$, wherein n is an integer having a value between 1 and 100. Within certain embodiments, a cleavage site may be inserted on either side of the structure, e.g., (cleavage site)-(cationic peptide)-[(cleavage site)-(cationic peptide)]$_n$ cleavage site, wherein n is an integer having a value between 1 and 100.

Within certain embodiments, utilizing the methods described herein, the unit: -(cleavage site)-(cationic peptide)- can be added to the above expression cassette in order to specifically add a defined number of cationic sequences to be expressed. Within various embodiments, n is an integer having a value of 2, 3, 5, 10, or, 20 on the lower end, and 10, 15, 20, 30, 40, 50, 75, or 80 on the upper end (e.g., n may be an integer between about 2 and 30, 2 and 40, etc., 5 and 30, 6, or, 7 and 40, etc., up to 10 or 20 to 40, 50, 70 or 80). As an example, within one embodiment n has a value of between 5 and 40 or 10 and 40.

Within certain embodiments, the nucleic acid molecule may further comprise a carrier protein. Within various embodiments, to the extent that a carrier protein is to be expressed by the expression cassette, it can be located at either the N-terminus or the C-terminus of the fusion protein. A wide range of carrier proteins can be utilized, including for example, a cellulose binding domain (CBD), or, a fragment of CBD. Within various embodiments, the carrier protein can be greater than, equal to, or less than 100 amino acids in length.

Within further embodiments, the cleavage sites within the expression cassette can be cleaved by, for example, low pH, or, by a reagent such as cyanogen bromide, 2-(2-nitrophenylsulphenyl)-3-methyl-3'-bromoindolenine, hydroxylamine, o-iodosobenzoic acid, Factor Xa, thrombin, enterokinase, collagenase, *Staphylococcus aureus* V8 protease, endoproteinase Arg-C, or trypsin.

Within another embodiment, the expression cassette may more specifically be comprised of (a) a carrier protein, (b) an anionic spacer peptide component having at least one peptide with the structure (cleavage site)-(anionic spacer peptide), and (c) a cationic peptide component having at least peptide with the structure (cleavage site)-(cationic peptide) wherein the cleavage site can be on either side of the anionic spacer peptide or cationic peptide, and elements (a), (b), and (c) can be in any order and or number. Within a further related embodiment, the expression cassette may be comprised of (a) an anionic spacer peptide component having at least one peptide with the structure (cleavage site)-(anionic spacer peptide), and (b) a cationic peptide component having at least peptide with the structure (cleavage site)-(cationic peptide), wherein the cumulative charge of said anionic spacer peptide component reduces the cumulative charge of said cationic peptide component.

To the extent an anionic spacer is included, such a spacer may have, 0, 1, 2, or more cysteine residues. Within certain embodiments, there can be more, the same number, or fewer anionic spacers than cationic peptides in the fusion construct. Within certain embodiments, the anionic spacer is smaller in size than the cationic peptide.

A wide variety of cleavage sites can be utilized, including for example, a methionine residue. In addition, a wide variety of promoters can be utilized, including for example the lacP promoter, tacP promoter, trcP promoter, srpP promoter, SP6 promoter, T7 promoter, araP promoter, trpP promoter, and λ promoter.

The present invention also provides methods for producing fusion proteins utilizing the above-described expression cassettes. Within one embodiment, such methods generally comprise the step of culturing a recombinant host cell containing an expression cassette, under conditions and for a time sufficient to produce the fusion protein. Representative examples of suitable host cells include yeast, fungi, bacteria (e.g., *E. coli*), insect, and plant cells.

Once the fusion protein has been produced, it may be further purified 1 and isolated. Further, the fusion protein may be cleaved into its respective components (e.g., utilizing low pH, or, a reagent such as cyanogen bromide, 2-(2-nitrophenylsulphenyl)-3-methyl-3'-bromoindolenine, hydroxylamine, o-iodosobenzoic acid, Factor Xa, thrombin, enterokinase, collagenase, *Staphylococcus aureus* V8 protease, endoproteinase Arg-C, or trypsin).

Further, the fusion protein or cleaved cationic peptide may be purified utilizing a chromatographic method (e.g., an anion chromatography column or resin). Within certain embodiments, the column can be charged with a base, and washed with water prior to loading the column with said cationic peptide. Within various embodiments, the column can be equilibrated with water and up to about 8 M urea. Moreover, the cationic peptide is solubilized in a solution comprising up to about 8 M urea. Within further embodiments, the cationic peptide is solubilized in a solution comprising a mild organic solvent, such as, for example, acetonitrile, or, an alcohol such as methanol or ethanol.

These and other aspects of the present invention will become evident upon reference to the following detailed description and attached drawings. In addition, various references are identified below and are incorporated by reference in their entirety.

DETAILED DESCRIPTION OF THE INVENTION

1. Overview

Figure 1A:
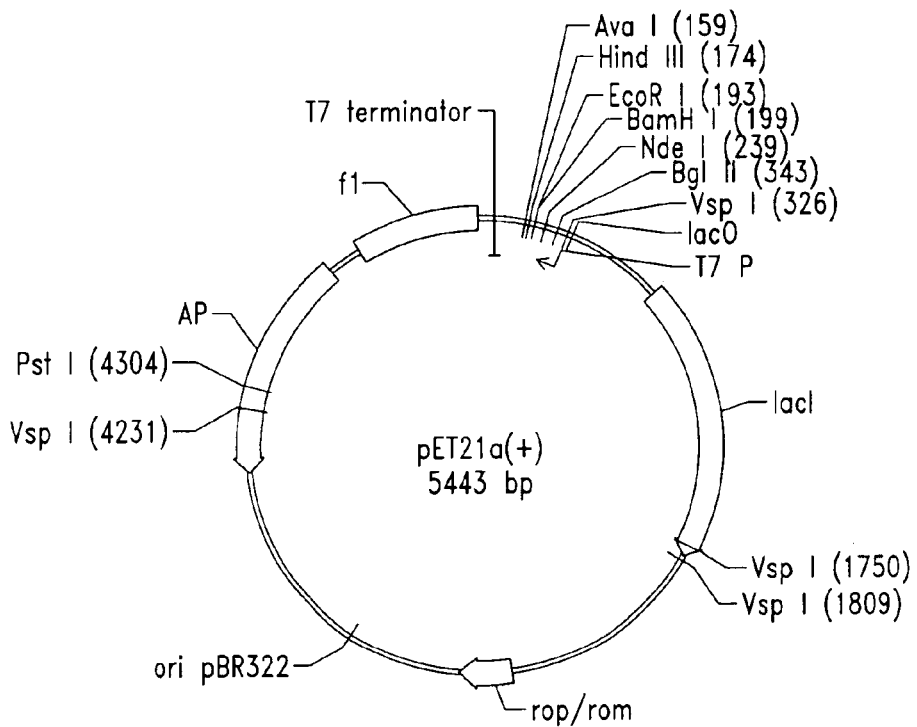
FIG. 1 is the maps of: (A) plasmid pET21(+), (B) plasmid pET-CBD 180, (C) a PCR fragment containing cbd 180 and (D) plasmids pET21CBD 180-B and pET21CBD180-X.

As discussed above, a successful approach to stabilizing foreign peptide gene products which are inherently unstable or toxic is to express them fused to a protein which displays stability in the relevant host cell. In the case of small cationic peptides, however, production of a fusion protein will lead to a small portion of the desired peptide and an apparent low yield. A major gain in productivity and therefore economics of the process can be made if the fraction of desired peptide in the fusion protein is substantially greater. A favored route for this concept concerns expression of a fusion protein containing multiple sequential copies (a concatomer or multi-domain protein) of the peptide separated by linker sequences. The linkers are the points at which the concatomer (multi-domain protein) will be cleaved to give monomers of the desired peptide with most probably modified C-termini as a result of the cleavage process.

On the other hand, increasing the number of copies of a cationic peptide per fusion protein will make it a more and more basic protein, which may effect the expression of the fusion protein and/or increase its toxicity for the host cell.

An approach to overcome the high basicity of the recombinantly-produced multi-domain cationic protein, and also decrease its toxicity, is to include small acidic peptide sequences in the linker sequences that neutralize the positive charge of the cationic peptide. To keep the economic concept of high ratio of the cationic peptide in the multi-domain protein it is important to engineer the acidic peptide to be as small as possible, preferably smaller than the cationic peptide. The natural phenomenon of a multipeptide precursor structure consisting of cationic peptide and anionic spacer has been described (Casteels-Josson et al (1993) EMBO J., vol. 12, 1569–1578). In this publication the authors describe the natural production of apidaecin, an antibacterial cationic peptide, in insects such as the honeybee (*Apis mellifera*). Apidaecin is generated as a single gene comprising multiple repeated precursor units, each consisting of an apidaecin peptide gene (18 amino acids) preceded by an acidic spacer region (6–8 amino acids). In a further example, Lee et al., *Protein Exp. Purif* 12:53 (1998), expressed in *E. coli* six copies of the cationic peptide buforin II per fusion protein, which also included as acidic peptide modified magainin intervening sequences that alternated with the cationic peptide sequences. The magainin intervening sequences were "modified" in that the sequences included flanking cysteine residues. According to Lee et al., the "presence of cysteine residues in the acidic peptide was critical for the high level expression of the fusion peptide multimers."

In initial studies, the present inventors used carrier proteins of different sizes to express monomer and polymer forms of cationic peptides. The test carrier protein of these studies were CBD and a fragment of the same derived from *Clostridium cellulovorans* cellulose binding protein A. The chosen carrier protein fulfilled the requirements of high expression and accumulation in *E. coli* as insoluble forms. This approach was limited by a significant decrease in expression when the number of cationic fused peptide genes exceeded three copies. There was essentially no expression from vectors containing more than four copies of a peptide gene. A new procedure was designed which allowed the multiplication of relevant cationic peptide genes using a specific anionic spacer sequence that encoded a negatively charged peptide. In these studies, the anionic spacer peptide consisted of 11 amino acids. Various genes encoding cationic peptide-anionic spacer peptide multi-domain proteins were constructed and fused to the carrier protein. A high level of expression was achieved for all constructs harboring more than thirty copies of the relevant cationic peptide gene. In subsequent studies, polymers of cationic peptide genes with anionic spacers were liberated from the carrier and expressed directly. These constructs achieved high levels of expression and a high percentage of target cationic peptide in the carrier-free multi-domain protein.

2. Definitions

In the description that follows, a number of terms are used extensively. The following definitions are provided to facilitate understanding of the invention.

A "structural gene" is a nucleotide sequence that is transcribed into messenger RNA (mRNA), which is then translated into a sequence of amino acids characteristic of a specific polypeptide.

As used herein, "nucleic acid" or "nucleic acid molecule" refers to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally-occurring nucleotides (such as deoxyribonucleotides and ribonucleotides), or analogs of naturally-occurring nucleotides (e.g., α-enantiomeric forms of naturally-occurring nucleotides), or a combination of both. An "isolated nucleic acid molecule" is a nucleic acid molecule that is not integrated in the genomic DNA of an organism. For example, a DNA molecule that encodes a cationic peptide that has been separated from the genomic DNA of a cell is an isolated DNA molecule. Another example of an isolated nucleic acid molecule is a chemically-synthesized nucleic acid molecule that is not integrated in the genome of an organism.

An "isolated polypeptide or protein" is a polypeptide that is essentially free from contaminating cellular components, such as carbohydrate, lipid, nucleic acid (DNA or RNA) or other proteinaceous impurities associated with the polypeptide in nature. Preferably the isolated polypeptide is sufficiently pure for clinical injection at the desired dose. Whether a particular cationic polypeptide preparation contains an isolated cationic polypeptide can be determined utilizing methods such as Urea/acetic acid polyacrylamide gel electrophoresis and Coomassie Brilliant Blue staining of the gel, reverse phase high pressure liquid chromatography, capillary electrophoresis, nucleic acid detection assays, and the Limulus Amebocyte Lysate test. Utilizing such a method an isolated polypeptide preparation will be at least about 95% pure polypeptide.

An "insoluble polypeptide" refers to a polypeptide that, when cells are broken open and cellular debris precipitated by centrifugation (e.g., 10,000 g to 15,000 g), produces substantially no soluble component, as determined by SDS polyacrylamide gel with Coomassie Blue staining.

A "promoter" is a nucleotide sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

The term "expression" refers to the biosynthesis of a gene product. For example, in the case of a structural gene, expression involves transcription of the structural gene into mRNA and the translation of mRNA into one or more polypeptides.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites at which foreign nucleotide sequences can be inserted in a determinable fashion without loss of an essential biological function of the vector, as well as nucleotide sequences encoding a marker gene that is suitable for use in the identification and selection of cells transformed with the cloning vector. Marker genes typically include genes that provide antibiotic resistance.

An "expression vector" is a nucleic acid molecule (plasmid, cosmid, or bacteriophage) encoding a gene that is expressed in a host cell. Typically, gene expression is placed under the control of a promoter, and optionally, under the control of at least one regulatory element. Such a gene is said to be "operably linked to" the promoter. Similarly, a regulatory element and a promoter are operably linked if the regulatory element modulates the activity of the promoter.

A "recombinant host" may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

As used herein, "cationic peptide" refers to a peptide that possesses an isoelectric point (pI) of 9 and above. A cationic peptide is at least five amino acids in length, and has at least one basic amino acid (e.g., arginine, lysine, histidine). Cationic peptides commonly do not have more than 50 amino acids, and typically contain 10 to 35 amino acid residues.

A "carrier protein" is an amino acid sequence that can be individually expressed in host cells and, by recombinant fusion to a desired peptide or polypeptide can act as a carrier, enabling the expression of the desired peptide in host cells.

An "anionic spacer peptide domain" is a peptide sequence that is sufficiently anionic to decrease the positive charge of an associated cationic peptide. That is, the combination of a cationic peptide and an anionic spacer peptide has a net charge that is essentially slightly positive, negative or neutral. The size of an anionic spacer domain is similar to but preferably smaller than the size of the cationic peptide domain.

As used herein, a "fusion protein" is a hybrid protein expressed by a nucleic acid molecule comprising nucleotide sequences of at least two genes. A "multi-domain protein" comprises a combination of preferably more than one "cationic peptide domain," and an equal, smaller or higher number of "anionic spacer peptide domains" with suitable cleavage sites for separating cationic peptide from the rest of the multi-domain protein. The multi-domain protein can be fused to a carrier protein to achieve higher expression and/or stability. If stability and expression level of multi-domain protein are satisfactory, there is no need to use a carrier protein. An "anionic spacer peptide component" comprises at least one anionic spacer peptide with a cleavage site. The "cumulative charge" of a cationic peptide component refers to the total charge of all cationic peptides that comprise the cationic peptide component. Similarly, the "cumulative charge" of an anionic spacer peptide component refers to the total charge of all anionic spacer peptides that comprise the anionic spacer peptide component.

As used herein, "antimicrobial activity" refers to the ability to kill or to prevent the growth of a microbe, or to kill or to prevent the growth of microbe-infected cells. The term "microbe" includes bacteria, fungi, yeast, algae, protozoa, and viruses. This term includes but will not be limited to all these interpretive descriptions of the biological activity of the cationic peptide.

L 3. Construction and Expression of Vectors Comprising Cationic Peptide Genes a. Cationic Peptide Expression Vectors The present invention contemplates the production of "cationic peptide," as that term is defined above. For example, suitable cationic peptides include but are not limited to, naturally occurring cationic peptides and analogs thereof, cecropins, normally made by lepidoptera (Steiner et al., Nature 292:246, 1981) and diptera (Merrifield et al., Ciba Found. Symp. 186:5, 1994), by porcine intestine (Lee et al., Proc. Nat'l Acad. Sci. USA 86:9159, 1989), by blood cells of a marine protochordate (Zhao et al., FEBS Lett. 412:144, 1997), synthetic analogs of cecropin A, melittin, and cecropin-melittin chimeric peptides (Wade et al., Int. J. Pept. Protein Res. 40:429, 1992), cecropin B analogs (Jaynes et al., Plant Sci. 89:43, 1993), chimeric cecropin A/B hybrids (Düring, Mol. Breed 2:297, 1996), magainins (Zasloff, Proc. Nat'l Acad. Sci USA 84:5449, 1987), cathelin-associated antimicrobial peptides from leukocytes of humans, cattle, pigs, mice, rabbits, and sheep (Zanetti et al., FEBS Lett. 374:1, 1995), vertebrate defensins, such as human neutrophil defensins [HNP 1–4], paneth cell defensins of mouse and human small intestine (Oulette and Selsted, *FASEB J.* 10:1280, 1996; Porter et al., *Infect. Immun.* 65:2396, 1997), vertebrate β-defensins, such as HBD-1 of human epithelial cells (Zhao et al., *FEBS Lett.* 368:331, 1995), HBD-2 of inflamed human skin (Harder et al., *Nature* 387:861, 1997), bovine β-defensins (Russell et al., *Infect. Immun.* 64:1565, 1996), plant defensins, such as Rs-AFP1 of radish seeds (Fehlbaum et al., *J. Biol. Chem.* 269:33159, 1994), α- and β-thionins (Stuart et al., *Cereal Chem.* 19:288, 1942; Bohlmann and Apel, *Annu. Rev. Physiol. Plant Mol. Biol.* 42:227, 1991), γ-thionins (Broekaert et al., *Plant Physiol.* 108:1353, 1995), the antifungal drosomycin (Fehlbaum et al., *J. Biol. Chem.* 269:33159, 1994), apidaecins, produced by honey bee, bumble bee, cicada killer, hornet, yellow jacket, and wasp (Casteels et al., *J. Biol. Chem.* 269:26107, 1994; Levashina et al., *Eur. J. Biochem.* 233:694, 1995), cathelicidins, such as indolicidin from bovine neutrophils (Falla et al., *J. Biol. Chem.* 277:19298, 1996), bacteriocins, such as nisin (Delves-Broughton et al., *Antonie van Leeuwenhoek J. Microbiol.* 69:193, 1996), and the protegrins and tachyplesins, which have antifingal, antibacterial and antiviral activities (Tamamura et al., *Biochim. Biophys. Acta* 1163:209, 1993; Aumelas et al., *Eur. J. Biochem.* 237:575, 1996; Iwanga et al., *Ciba Found. Symp.* 186:160, 1994). Illustrative cationic peptides are listed in Table 1.

TABLE 1

ILLUSTRATIVE CATIONIC PEPTIDES**

| Group Name | Peptide | Sequence | SEQ ID | Reference* |
|---|---|---|---|---|
| Abaecins | Abaecin | YVPLPNVPQPGRRPFPTF PGQGPFNPKIKWPQGY | 37 | Casteels et al. (1990) |
| Andropins | Andropin | VFIDILDKVENAIHNAAQ VGIGFAKPFEKLINPK | 38 | Samakovlis et al. (1991) |
| Apidaecins | Apidaecin IA | GNNRPVYIPQPRPPHPRI | 39 | Casteels et al. (1989) |
| | Apidaecin IB | GNNRPVYIPQPRPPHPRL | 40 | Casteels et al. (1989) |
| | Apidaecin II | GNNRPIYIPQPRPPHPRL | 41 | Casteels et al. (1989) |
| AS | AS-48 | 7.4 kDa | | Galvez et al. (1989) |
| Bactenecins | Bactenecin | RLCRIVVIRVCR | 42 | Romeo et al. (1988) |
| Bac | Bac5 | RFRPPIRRPPIRPPFYPPFRPPIRPPI FPPIRPPFRPPLRFP | 43 | Frank et al. (1990) |
| | Bac7 | RRIRPRPPRLPRPRPRPLPFPRPGP RPIPRPLPFPRPGPRPIPRPLPFPRP GPRPIPRP | 44 | Frank et al. (1990) |
| Bactericidins | Bactericidin B2 | WNPFKELERAGQRVRDAVISAA PAVATVGQAAAIARG* | 45 | Dickinson et al. (1988) |
| | Bactericidin B-3 | WNPFKELERAGQRVRDAIISAGP AVATVGQAAAIARG | 46 | Dickinson et al. (1988) |
| | Bactericidin B-4 | WNPFKELERAGQRVRDAIISAAP AVATVGQAAAIARG | 47 | Dickinson et al. (1988) |
| | Bactericidin B-5P | WNPFKELERAGQRVRDAVISAA AVATVGQAAAIARG | 48 | Dickinson et al. (1988) |
| Bacteriocins | Bacteriocin C3603 | 4.8 kDa | | Takada et al. (1984) |
| | Bacteriocin IY52 | 5 kDa | | Nakamura et al. (1983) |
| Bombinins | Bombinin | GIGALSAKGALKGLAKGLAZHF AN* | 49 | Csordas and Michl (1970) |
| | BLP-1 | GIGASILSAGKSALKGLAKGLAE HFAN* | 50 | Gibson et al. (1991) |
| | BLP-2 | GIGSAILSAGKSALKGIAKGLAE HFAN* | 51 | Gibson et al. (1991) |
| Bombolitins | Bombolitin BI | IKITTMLAKLGKVLAHV* | 52 | Argiolas and Pisano (1985) |
| | Bombolitin BII | SKITDILAKLGKVLAHV* | 53 | Argiolas and Pisano (1985) |
| BPTI | Bovine Pancreatic Trypsin Inhibitor (BPTI) | RPDFCLEPPYTGPCKARIIRYFYN AKAGLCQTFVYGGCRAKRNNF KSAEDCMRTCGGA | 54 | Creighton and Charles (1987) |
| Brevinins | Brevinin-1E | FLPLLAGLAANFLPKIFCKITRKC | 55 | Simmaco et al. (1993) |
| | Brevinin-2E | GIMDTLKNLAKTAGKGALQSLL NKASCKLSGQC | 56 | Simmaco et al. (1993) |
| Cecropins | Cecropin A | KWKLFKKIEKVGQNIRDGIIKAG PAVAVVGQATQIAK* | 57 | Gudmundsson et al. (1991) |
| | Cecropin B | KWKVFKKIEKMGRNIRNGIVKA GPAIAVLGEAKAL* | 58 | Xanthopoulos et al. (1988) |
| | Cecropin C | GWLKKLGKRIERIGQHTRDATIQ GLGIAQQAANVAATARG* | 59 | Tryselius et al. (1992) |
| | Cecropin D | WNPFKELEKVGQRVRDAVISAG PAVATVAQATALAK* | 60 | Hultmark et al. (1982) |
| | Cecropin $P_1$ | SWLSKTAKKLENSAKKRISEGIA IAIQGGPR | 61 | Lee et al. (1989) |
| Charybdtoxins | Charybdtoxin | ZFTNVSCTTSKECWSVCQRLHN TSRGKCMNKKCRCYS | 62 | Schweitz et al. (1989) |
| Coleoptericins | Coleoptericin | 8.1 kDa | | Bulet et al. (1991) |
| Crabrolins | Crabrolin | FLPLILRKIVTAL* | 63 | Argiolas and Pisano (1984) |

TABLE 1-continued

ILLUSTRATIVE CATIONIC PEPTIDES**

| Group Name | Peptide | Sequence | SEQ ID | Reference* |
|---|---|---|---|---|
| α-Defensins | Cryptdin 1 | LRDLVCYCRSRGCKGRERMNGTCRKGHLLYTLCCR | 64 | Selsted et al. (1992) |
| | Cryptdin 2 | LRDLVCYCRTRGCKRRERMNGTCRKGHLMYTLCCR | 65 | Selsted et al. (1992) |
| | MCP1 | VVCACRRALCLPRERRAGFCRIRGRIHPLCCRR | 66 | Selsted et al. (1983) |
| | MCP2 | VVCACRRALCLPLERRAGFCRIRGRIHPLCCRR | 67 | Ganz et al. (1989) |
| | GNCP-1 | RRCICTTRTCRFPYRRLGTCIFQNRVYTFCC | 68 | Yamashita and Saito (1989) |
| | GNCP-2 | RRCICTTRTCRFPYRRLGTCLFQNRVYTFCC | 69 | Yamashita and Saito (1989) |
| | HNP-1 | ACYCRIPACIAGERRYGTCIYQGRLWAFCC | 70 | Lehrer et al. (1991) |
| | HNP-2 | CYCRIPACIAGERRYGTCIYQGRLWAFCC | 71 | Lehrer et al. (1991) |
| | NP-1 | VVCACRRALCLPRERRAGFCRIRGRIHPLCCRR | 72 | Ganz et al. (1989) |
| | NP-2 | VVCACRRALCLPLERRAGFCRIRGRIHPLCCRR | 73 | Ganz et al. (1989) |
| | RatNP-1 | VTCYCRRTRCGFRERLSGACGYRGRIYRLCCR | 74 | Eisenhauer et al. (1989) |
| | RatNP-2 | VTCYCRSTRCGFRERLSGACGYRGRIYRLCCR | 75 | Eisenhauer et al. (1989) |
| β-Defensins | BNBD-1 | DFASCHTNGGICLPNRCPGHMIQIGICFRPRVKCCRSW | 76 | Selsted et al. (1993) |
| | BNBD-2 | VRNHVTCRINRGFCVPIRCPGRTRQIGTCFGPRIKCCRSW | 77 | Selsted et al. (1993) |
| | TAP | NPVSCVRNKGICVPIRCPGSMKQIGTCVGRAVKCCRKK | 78 | Diamond et al. (1991) |
| Defensins-insect | Sapecin | ATCDLLSGTGINHSACAAHCLLRGNRGGYCNGKAVCVCRN | 79 | Hanzawa et al. (1990) |
| | Insect defensin | GFGCPLDQMQCHRHCQTITGRSGGYCSGPLKLTCTCYR | 80 | Bulet et al. (1992) |
| Defensins-scorpion | Scorpion defensin | GFGCPLNQGACHRHCRSIRRRGGYCAGFFKQTCTCYRN | 81 | Cociancich et al. (1993) |
| Dermaseptins | Dermaseptin | ALWKTMLKKLGTMALHAGKAALGAADTISQTQ | 82 | Mor et al. (1991) |
| Diptericins | Diptericin | 9 kDa | | Reichhardt et al. (1989) |
| Drosocins | Drosocin | GKPRPYSPRPTSHPRPIRV | 83 | Bulet et al. (1993) |
| Esculentins | Esculentin | GIFSKLGRKKIKNLLISGLKNVGKEVGMDVVRTGIDIAGCKIKGEC | 84 | Simmaco et al. (1993) |
| Indolicidins | Indolicidin | ILPWKWPWWPWRR* | 85 | Selsted et al. (1992) |
| Lactoferricins | Lactoferricin B | FKCRRWQWRMKKLGAPSITCVRRAF | 86 | Bellamy et al. (1992b) |
| Lantibiotics | Nisin | ITSISLCTPGCKTGALMGCNMKTATCHCSIHVSK | 87 | Hurst (1981) |
| | Pep 5 | TAGPAIRASVKQCQKTLKATRLFTVSCKGKNGCK | 88 | Keletta et al. (1989) |
| | Subtilin | MSKFDDFDLDVVKVSKQDSKITPQWKSESLCTPGCVTGALQTCFLQTLTCNCKISK | 89 | Banerjee and Hansen (1988) |
| Leukocins | Leukocin A-val 187 | KYYGNGVHCTKSGCSVNWGEAFSAGVHRLANGGNGFW | 90 | Hastings et al. (1991) |
| Magainins | Magainin I | GIGKFLHSAGKFGKAFVGEIMKS* | 91 | Zasloff (1987) |
| | Magainin II | GIGKFLHSAKKFGKAFVGEIMNS* | 92 | Zasloff (1987) |
| | PGLa | GMASKAGAIAGKIAKVALKAL* | 93 | Kuchler et al. (1989) |
| | PGQ | GVLSNVIGYLKKLGTGALNAVLKQ | 94 | Moore et al. (1989) |
| | XPF | GWASKIGQTLGKIAKVGLKELIQPK | 95 | Sures and Crippa (1984) |
| Mastoparans | Mastoparan | INLKALAALAKKIL* | 96 | Bernheimer and Rudy (1986) |
| Melittins | Melittin | GIGAVLKVLTTGLPALISWIKRKRQQ | 97 | Tosteson and Tosteson (1984) |
| Phormicins | Phormicin A | ATCDLLSGTGINHSACAAHCLLRGNRGGYCNGKGVCVCRN | 98 | Lambert et al. (1989) |
| | Phormicin B | ATCDLLSGTGINHSACAAHCLLRGNRGGYCNRKGVCVRN | 99 | Lambert et al. (1989) |
| Polyphemusins | Polyphemusin I | RRWCFRVCYRGFCYRKCR* | 100 | Miyata et al. (1989) |
| | Polyphemusin II | RRWCFRVCYKGFCYRKCR* | 101 | Miyata et al. (1989) |

TABLE 1-continued

ILLUSTRATIVE CATIONIC PEPTIDES**

| Group Name | Peptide | Sequence | SEQ ID | Reference* |
|---|---|---|---|---|
| Protegrins | Protegrin I | RGGRLCYCRRRFCVCVGR | 102 | Kokryakov et al. (1993) |
| | Protegrin II | RGGRLCYCRRRFCICV | 103 | Kokryakov et al. (1993) |
| | Protegrin III | RGGGLCYCRRRFCVCVGR | 104 | Kokryakov et al. (1993) |
| Royalisins | Royalisin | VTCDLLSFKGQVNDSACAANCLSLGKAGGHCEKGVCICRKTSFKDLWDKYF | 105 | Fujiwara et al. (1990) |
| Sarcotoxins | Sarcotoxin IA | GWLKKIGKKIERVGQHTRDATIQGLGIAQQAANVAATAR* | 106 | Okada and Natori (1985b) |
| | Sarcotoxin IB | GWLKKIGKKIERVGQHTRDATIQVIGVAQQAANVAATAR* | 107 | Okada and Natori (1985b) |
| Seminal plasmins | Seminalplasmin | SDEKASPDKHHRFSLSRYAKLANRLANPKLLETFLSKWIGDRGNRSV | 108 | Reddy and Bhargava (1979) |
| Tachyplesins | Tachyplesin I | KWCFRVCYRGICYRRCR* | 109 | Nakamura et al. (1988) |
| | Tachyplesin II | RWCFRVCYRGICYRKCR* | 110 | Muta et al. (1990) |
| Thionins | Thionin BTH6 | KSCCKDTLARNCYNTCRFAGGSRPVCAGACRCKIISGPKCPSDYPK | 111 | Bohlmann et al. (1988) |
| Toxins | Toxin 1 | GGKPDLRPCIIPPCHYIPRPKPR | 112 | Schimdt et al. (1992) |
| | Toxin 2 | VKDGYIVDDVNCTYFCGRNAYCNEECTKLKGESGYCQWASPYGNACYCKLPDHVRTKGPGRCH | 113 | Bontems et al. (1991) |

*Argiolas and Pisano, JBC 259:10106 (1984); Argiolas and Pisano, JBC 260:1437 (1985); Banerjee and Hansen, JBC 263:9508 (1988); Bellamy et al., J. Appl. Bacter. 73:472 (1992); Bernheimer and Rudy, BBA 864:123 (1986); Bohlmann et al., EMBO J. 7:1559 (1988); Bontems et al., Science 254:1 (1991); Bulet et al., JBC 266:24520 (1991); Bulet et al., Eur. J. Biochem. 209:977 (1992); Bulet et al., JBC 14893 (1993); Casteels et al., EMBO J. 8:2387 (1989); Casteels et al., Eur. J. Biochem. 187:381 (1990); Cociancich et al., BBRC 194:17 (1993); Creighton and Charles, J. Mol. Biol. 194:11 (1987); Csordas and Michl, Monatsh Chemistry 101:82 (1970); Diamond et al., PNAS 88:3952 (1991); Dickinson et al., JBC 263:19424 (1988); Eisenhauer et al., Infect. and Imm. 57:2021 (1989); Frank et al., JBC 26518871 (1990); Fujiwara et al., JBC 265:11333 (1990); Gálvez et al., Antimicrobial Agents and Chemotherapy 33:437 (1989); Ganz et al., J. Immunol. 143:1358 (1989); Gibson et al., JBC 266:23103 (1991); Gudmundsson et al., JBC 266:11510 (1991); Hanzawa et al., FEBS Letters 269:413 (1990); Hastings et al., J. Bacteriology 173:7491 (1991); Hultmark et al., Eur. J. Biochem. 127:207 (1982); Hurst, Adv. Appl. Micro. 27:85 (1981); Kaletta et al., Archives of Microbiology 152:16 (1989); Kokryakov et al., FEBS Letters 327:231 (1993); Kuchler et al., Eur. J. Biochem. 179:281 (1989); Lambert er al., PNAS 86:262 (1989); Lee et al., PNAS 86:9159 (1989); Lehrer et al., Cell 64:229 (1991); Miyata et al., J. Biochem. 106:663 (1989); Moore et al., JBC 266:19851 (1991); Mor et al., Biochemistry 30:8824 (1991); Muta et al., J. Biochem. 108:261 (1990); Nakamura et al., JBC 263:16709 (1988); Nakamura et al., Infection and Immunity 39:609 (1983); Okada and Natori, Biochem. J. 229:453 (1985); Reddy and Bhargava, Nature 279:725 (1979); Reichhart et al., Eur. J. Biochem. 182:423 (1989); Romeo et al., JBC 263:9573 (1988); Samakovlis et al., EMBO J. 10:163 (1991); Schmidt et al., Toxicon 30:1027 (1992); Schweitz et al., Biochem. 28:9708 (1989); Selsted et al., JBC 258:14485 (1983); Selsted et al., JBC 267:4292 (1992); Simmaco et al., FEBS Lett. 324:159 (1993); Sures and Crippa, PNAS 81:380 (1984); Takada et al., Infect. and Imm. 44:370 (1984); Tosteson and Tosteson, Biophysical J. 45:112 (1984); Tryselius et al., Eur. J. Biochem. 204:395 (1992); Xanthopoulos et al., Eur. J. Biochem. 172:371 (1988); Yamashita Saito, Infect. and Imm. 57:2405 (1989); Zasloff, PNSA 84:5449 (1987).
**See also U.S. Pat. Nos. 4,822,608; 4,962,277; 4,980,163; 5,028,530; 5,096,886; 5,166,321; 5,179,078; 5,202,420; 5,212,073; 5,242,902; 5,254,537; 5,278,287; 5,300,629; 5,304,540; 5,324,716; 5,344,765; 5,422,424; 5,424,395; 5,446,127; 5,459,235; 5,464,823; 5,466,671; 5,512,269; 5,516,682; 5,519,115; 5,519,116; 5,547,939; 5,556,782; 5,610,139; 5,645,966; 5,567,681; 5,525,353; 5,589,568; 5,594,103, 5,610,139; 5,631,144; 5,635,479; 5,656,456; 5,707,855; 5,731,149; 5,714,467; 5,726,155; 5,747,449; 5,756,462; PCT Publication Nos. WO 89/00199; WO 90/11766; WO 90/11771; WO 91/00869; WO 91/12815; WO 91/17760; WO 94/05251; WO 94/05156; WO 94/07528; WO 95/21601; WO 97/00694; WO 97/11713; WO 97/18826; WO 97/02287; WO 98/03192; WO 98/07833; WO 98/07745; WO 98/06425 European Application Nos. EP 17785; 349451; 607080; 665239; and Japanese Patent/Patent Application Nos. 4341179; 435883; 7196408; 798381; and 8143596.

Argiolas and Pisano, *JBC* 259:10106 (1984); Argiolas and Pisano, *JBC* 260:1437 (1985); Banerjee and Hansen, *JBC* 263:9508 (1988); Bellamy et al., *J. Appl. Bacter.* 73:472 (1992); Bernheimer and Rudy, *BBA* 864:123 (1986); Bohlmann et al., *EMBO J.* 7:1559 (1988); Bontems et al., *Science* 254:1521 (1991); Bulet et al., *JBC* 266:24520 (1991); Bulet et al., *Eur. J. Biochem.* 209:977 (1992); Bulet et al., *JBC* 268:14893 (1993); Casteels et al., *EMBO J.* 8:2387 (1989); Casteels et al., *Eur. J. Biochem.* 187:381 (1990); Cociancich et al., *BBRC* 194:17 (1993); Creighton and Charles, *J. Mol. Biol.* 194:11 (1987); Csordas and Michl, *Monatsh Chemistry* 101:82 (1970); Diamond et al., *PNAS* 88:3952 (1991); Dickinson et al., *JBC* 263:19424 (1988); Eisenhauer et al., *Infect and Imm.* 57:2021 (1989); Frank et al., *JBC* 26518871 (1990); Fujiwara et al., *JBC* 265:11333 (1990); Gálvez et al., *Antimicrobial Agents and Chemotherapy* 33:437 (1989); Ganz et al., *J. Immunol.* 143:1358 (1989); Gibson et al., *JBC* 266:23103 (1991); Gudmundsson et al., *JBC* 266:11510 (1991); Hanzawa et al., *FEBS Letters* 269:413 (1990); Hastings et al., *J. Bacteriology* 173:7491 (1991); Hultmark et al., *Eur. J. Biochem.* 127:207 (1982); Hurst, *Adv. Appl. Micro.* 27:85 (1981); Kaletta et al., *Archives of Microbiology* 152:16 (1989); Kokryakov et al., *FEBS Letters* 327:231 (1993); Kuchler et al., *Eur. J. Biochem.* 179:281 (1989); Lambert et al., *PNAS* 86:262 (1989); Lee et al., *PNAS* 86:9159 (1989); Lehrer et at., *Cell* 64:229 (1991); Miyata et al., *J. Biochem.* 106:663 (1989); Moore et al., *JBC* 266:19851 (1991); Mor et al., *Biochemistry* 30:8824 (1991); Muta et al., *J. Biochem.* 108:261 (1990); Nakamura et al., *JBC* 263:16709 (1988); Nakamura et al., *Infection and*

*Immunity* 39:609 (1983); Okada and Natori, *Biochem. J.* 229:453 (1985); Reddy and Bhargava, *Nature* 279:725 (1979); Reichhart et al., *Eur. J. Biochem.* 182:423 (1989); Romeo et al., *JBC* 263:9573 (1988); Samakovlis et al., *EMBO J.* 10:163 (1991); Schmidt et al., *Toxicon* 30:1027 (1992); Schweitz et al., *Biochem.* 28:9708 (1989); Selsted et al., *JBC* 258:14485 (1983); Selsted et al., *JBC* 267:4292 (1992); Simmaco et al., *FEBS Lett.* 324:159 (1993); Sures and Crippa, *PNAS* 81:380 (1984); Takada et al., *Infect. and Imm.* 44:370 (1984); Tosteson and Tosteson, *Biophysical J* 45:112 (1984); Tryselius et al., *Eur. J. Biochem.* 204:395 (1992); Xanthopoulos et al., *Eur. J. Biochem.* 172:371 (1988); Yamashita and Saito, *Infect. and Imm.* 57:2405 (1989); Zasloff, *PNAS* 84:5449 (1987).

See also U.S. Pat. Nos. 4,822,608; 4,962,277; 4,980,163; 5,028,530; 5,096,886; 5,166,321; 5,179,078; 5,202,420; 5,212,073; 5,242,902; 5,254,537; 5,278,287; 5,300,629; 5,304,540; 5,324,716; 5,344,765; 5,422,424; 5,424,395; 5,445,127; 5,459,235; 5,464,823; 5,466,671; 5,512,269; 5,516,682; 5,519,115; 5,519,116; 5,547,939; 5,556,782; 5,610,139; 5,645,966; 5,567,681; 5,585,353; 5,589,568; 5,594,103; 5,610,139; 5,631,144; 5,635,479; 5,656,456; 5,707,855; 5,731,149; 5,714,467; 5,726,155; 5,747,449; 5,756,462; PCT Publication Nos. WO 89/00199; WO 90/11766; WO 90/11771; WO 91/00869; WO 91/12815; WO 91/17760; WO 94/05251; WO 94/05156; WO 94/07528; WO 95/21601; WO 97/00694; WO 97/11713; WO 97/18826; WO 97/02287; WO 98/03192; WO 98/07833; WO 98/07745; WO 98/06425 European Application Nos. EP 17785; 349451; 607080; 665239; and Japanese Patent/Patent Application Nos. 4341179; 435883; 7196408; 798381; and 8143596.

Nucleic acid molecules encoding cationic peptides can be isolated from natural sources or can also be obtained by automated synthesis of nucleic acid molecules or by using the polymerase chain reaction (PCR) with oligonucleotide primers having nucleotide sequences that are based upon known nucleotide sequences of cationic peptides. In the latter approach, a cationic peptide gene is synthesized using mutually priming long oligonucleotides (see, for example, Ausubel et al. (eds.), *Short Protocols in Molecular Biology, $3^{rd}$ Edition*, pages 8–8 to 8–9 (John Wiley & Sons 1995), "Ausubel (1995)"). Established techniques using the polymerase chain reaction provide the ability to synthesize DNA molecules of at least two kilobases in length (Adang et al., *Plant Molec. Biol.* 21:1131, 1993; Bambot et al., *PCR Methods and Applications* 2: 266, 1993; Dillon et al., "Use of the Polymerase Chain Reaction for the Rapid Construction of Synthetic Genes," in *Methods in Molecular Biology, Vol. 15: PCR Protocols: Current Methods and Applications*, White (ed.), pages 263–268, (Humana Press, Inc. 1993); Holowachuk et al., *PCR Methods Appl.* 4: 299, 1995).

As noted above, analogs of natural cationic peptides can also be recombinantly produced by the presently described methods. The presence of a codon may have an adverse effect on expression and therefore a DNA sequence encoding the desired cationic peptide is optimized for a particular host system, in this case *E. coli*. Amino acid sequences of novel cationic peptides are disclosed, for example, by Falla et al., WO 97/08199, and by Fraser et al., WO 98/07745.

One type of cationic peptide analog is a peptide that has one or more conservative amino acid substitutions, compared with the amino acid sequence of a naturally occurring cationic peptide. For example, a cationic peptide analog can be devised that contains one or more amino acid substitutions of a known cationic peptide sequence, in which an alkyl amino acid is substituted for an alkyl amino acid in the natural amino acid sequence, an aromatic amino acid is substituted for an aromatic amino acid in the natural amino acid sequence, a sulfur-containing amino acid is substituted for a sulfur-containing amino acid in the natural amino acid sequence, a hydroxy-containing amino acid is substituted for a hydroxy-containing amino acid in the natural amino acid sequence, an acidic amino acid is substituted for an acidic amino acid in the natural amino acid sequence, a basic amino acid is substituted for a basic amino acid in the natural amino acid sequence, or a dibasic monocarboxylic amino acid is substituted for a dibasic monocarboxylic amino acid in the natural amino acid sequence.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

Nucleotide sequences encoding such "conservative amino acid" analogs can be obtained, for example, by oligonucleotide-directed mutagenesis, linker-scanning mutagenesis, mutagenesis using the polymerase chain reaction, and the like (see Ausubel (1995) at pages 8–10 to 8–22; and McPherson (ed.), *Directed Mutagenesis: A Practical Approach* (IRL Press 1991)). The antimicrobial activity of such analogs can be determined using a standard method, such as the assays described herein. Alternatively, a cationic peptide analog can be identified by the ability to specifically bind anti-cationic peptide antibodies. Typically, cationic peptide analogs should exhibit at least 50%, and preferably, greater than 70, 80 or 90%, of the activity of the corresponding naturally occurring cationic peptide.

Although one objective in constructing a cationic peptide variant may be to improve its activity, it may also be desirable to alter the amino acid sequence of a naturally occurring cationic peptide to enhance its production in a recombinant host cell. For example, a nucleotide sequence encoding a radish cationic peptide may include a codon that is commonly found in radish, but is rare for *E. coli*. The presence of a rare codon may have an adverse effect on protein levels when the radish cationic peptide is expressed in recombinant *E. coli*. Methods for altering nucleotide sequences to alleviate the codon usage problem are well known to those of skill in the art (see, for example, Kane, *Curr. Opin. Biotechnol.* 6: 494, 1995, Makrides, *Microbiol Rev.* 60:512, 1996, and Brown (Ed.), *Molecular Biology LabFax* (BIOS Scientific Publishers, Ltd. 1991), which provides a codon usage table on pages 245–253).

The present invention contemplates the use of "anionic spacer peptide" as that term is defined above. As described below, an illustrative anionic spacer peptide has the amino acid sequence of HEAEPEAEPIM (SEQ ID NO: 27) where the methionine residue can be used as a cleavage site. Similar naturally occurring examples of anionic spacer peptides include EAEPEAEP (SEQ ID NO:28), EAKPEAEP (SEQ ID NO:29), EAEPKAEP (SEQ ID NO:30), EAESEAEP (SEQ ID NO:31), EAELEAEP (SEQ ID NO:32), EPEAEP (SEQ ID NO:33) and EAEP (SEQ ID NO:34), (Casteels-Josson, et al. EMBO J., 12:1569–1578, 1993). Additional anionic spacer peptides are suitable for use in producing cationic peptides such as doubles or other combinations of those illustrated above. When designing an anionic spacer peptide for expression of a particular cationic peptide in the multi-domain protein concept, the following criteria should be borne in mind: the negative charge of the anionic spacer peptide should substantially reduce the positive charge of the cationic peptide in the multi-domain fusion proteins, a cleavage point must be present at which the multi-domain protein will be cleaved to give monomers of the desired peptide, and the anionic spacer peptide is preferably smaller than the cationic peptide. Such fusion proteins can be designed with alternating units of cationic peptide and anionic spacer peptide. Such a configuration, however, is not required. Any sequence of cationic peptide and anionic spacer peptide is acceptable, as long as the cumulative charge of the concatomer in the multidomain protein will not effect its expression in host cells.

In the examples described herein, a cellulose binding domain (CBD) carrier protein was used to illustrate methods for producing cationic peptides. Additional suitable examples of carrier proteins include, but are not limited to, glutathione-S-transferase (GST), *Staphylococcus aureus* protein A, two synthetic IgG-binding domains (ZZ) of protein A, outer membrane protein F, β-galactosidase (lacZ), and various products of bacteriophage λ and bacteriophage T7. From the teachings provided herein, it is apparent that many other proteins may be used as carriers. As shown by the use of the CBD fragment, an entire carrier protein need not be used, as long as it is highly expressed in the host cell. For the sake of simplicity and economics, suitable carrier proteins should be as small as possible, around 100 amino acid residues or preferably less. In certain cases, it is desirable to use a carrier protein that either lacks cysteine residues or that contains no more than one cysteine residue. It is also desirable to avoid methionine residues except in the cleavage site if CNBr reagent is to be used to release the linked peptide.

To facilitate isolation of the cationic peptide sequence, amino acids susceptible to cleavage can be used to bridge the carrier protein, a cationic peptide moiety, and an anionic spacer peptide moiety in the multi-domain protein. The determination and design of the amino acid sequence of the cleavage site is highly dependent on the strategy of cleavage and the amino acid sequence of the cationic peptide, anionic spacer peptide and carrier protein. The removal of the cationic peptide can be accomplished through any known chemical or enzymatic cleavages specific for peptide bonds. Chemical cleavages include (R. A. Jue & R. F. Doolittle, Biochemistry, (1985) 24:162–170; R. L. Lundblad, Chemical Reagents for Protein Modification (CRC Press, Boca Raton, Fla.; 1991), Chapter 5.), but are not limited to those treated by cyanogen bromide cleavages at methionine (Met↓), N-chlorosuccinimide or o-iodosobenzoic acid at tryptophan (Trp↓), hydroxylamine at asparaginyl-glycine bonds (Asn↓Gly), or low pH at aspartyl-proline bonds (Asp↓Pro). Alternatively, there are a vast number of proteases described in the literature but the majority have little specificity for a cleavage site. Enzymatic cleavages which can be performed include, but are not limited to those catalyzed by Factor Xa, Factor XIIa, thrombin, enterokinase, collagenase, *Staphylococcus aureus* V8 protease (endoproteinase Glu-C), endoproteinase Arg-C, endoproteinase Lys-C, chymotrypsin or trypsin.

To express a cationic peptide gene, a nucleic acid molecule encoding the peptide must be operably linked to regulatory sequences that control transcription and translation (expression) in an expression vector and then introduced into a host cell. In addition, expression vectors can include a marker gene which is suitable for selection of cells that carry the expression vector.

The expression vectors of the present invention comprise nucleic acid molecules encoding multi-domain fusion proteins with more than one copy of a cationic peptide gene. As can be shown, multi-domain fusion proteins having a carrier protein domain, an anionic spacer peptide component, and a cationic peptide component may include from two to more than 30 copies, of a cationic peptide gene. Multi-domain fusion proteins that lack an anionic spacer peptide component, but contain a carrier protein domain and a cationic peptide component include two to four copies of a cationic peptide gene. Moreover, multi-domain fusion proteins that lack a carrier protein domain, but include both anionic spacer peptide and cationic peptide components may include from five to more than 20 copies of a cationic peptide gene.

Preferably, cationic peptides are produced in prokaryotic host cells. Suitable promoters that can be used to express polypeptides in a prokaryotic host are well-known to those of skill in the art and for example include T4, T3, SP6 and T7 promoters recognized by specific phage RNA polymerases, the int, $P_R$ and $P_L$ promoters of bacteriophage lambda, the trp, recA, heat shock, lacUV5, tac, lpp-lacSpr, phoA, lacP, tacP, trcP, srpP, araP, and lacZ promoters of *E. coli*, promoters of *B. subtilis*, the promoters of the bacteriophages of *Bacillus, Streptomyces* promoters, the bla promoter of the cat promoter. Prokaryotic promoters have been reviewed by Glick, *J. Ind. Microbiol.* 1: 277, 1987, Watson et al., *Molecular Biology of the Gene, 4th Ed.* (Benjamin Cummins 1987), and by Ausubel et al. (1995).

Preferred prokaryotic hosts include *E. coli, Bacillus subtilus,* and *Staphylococcus aureus*. Suitable strains of *E. coli* include BL21(DE3), BL21(DE3)pLysS, BL21(DE3) pLysE, DH1, DH4I, DH5, DH5I, DH5IF', DH51MCR, DH10B, DH10B/p3, DH11S, C600, HB101, JM105, JM105, JM109, JM110, K38, RR1, Y1088, Y1089, CSH18, ER1451, and ER1647 (see, for example, Brown (Ed.), *Molecular Biology Labfax* (Academic Press 1991)). Suitable strains of *Bacillus subtilus* include BR151, YB886, MI119, MI120, and B170 (see, for example, Hardy, "*Bacillus* Cloning Methods," in *DNA Cloning: A Practical Approach*, Glover (Ed.) (IRL Press 1985)). An illustrative strain of *Staphylococcus aureus* is RN4220 (Kreiswirth et al., *Nature* 305: 709, 1983). The present invention does not require the use of bacterial strains that are protease deficient.

An expression vector can be introduced into host cells using a variety of standard techniques including calcium phosphate transfection, microprojectile-mediated delivery, electroporation, and the like. Methods for introducing expression vectors into bacterial cells are provided by Ausubel (1995). Methods for expressing proteins in prokaryotic hosts are well-known to those of skill in the art (see, for example, Williams et al., "Expression of foreign proteins in *E. coli* using plasmid vectors and purification of specific polyclonal antibodies," in DNA Cloning 2: Expression Systems, 2nd Edition, Glover et al. (eds.), page 15 (Oxford University Press 1995); and Georgiou, "Expression of Proteins in Bacteria," in *Protein Engineering: Principles and Practice*, Cleland et al. (eds.), page 101 (John Wiley & Sons, Inc. 1996)).

Cationic peptides can also be expressed in recombinant yeast cells. Promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include Yip-based vectors, such as YIp5, YRp vectors, such as YRp17, YEp vectors such as YEp13 and YCp vectors, such as YCp19. One skilled in the art will appreciate that there are a wide variety of suitable vectors for expression in yeast cells.

The baculovirus system provides an efficient means to express cationic peptide genes in insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila* metallothionein promoter. Suitable insect host cells include cell lines derived from IPLB-Sf-21, a *Spodoptera frugiperda* pupal ovarian cell line, such as Sf21 (AQTCC CRL 1711), Sf21AE, and Sf21 (Invitrogen Corporation; San Diego, Calif.), as well as *Drosophila* Schneider-2 cells. Established techniques for producing recombinant proteins in baculovirus systems are provided by Bailey et al., "Manipulation of Baculovirus Vectors," in *Methods in Molecular Biology, Volume 7: Gene Transfer and Expression Protocols*, Murray (ed.), pages 147–168 (The Humana Press, Inc. 1991), by Patel et al., "The baculovirus expression system," in *DNA Cloning 2: Expression Systems*, 2nd *Edition*, Glover et al. (eds.), pages 205–244 (Oxford University Press 1995), by Ausubel (1995) at pages 16–37 to 16–57, by Richardson (ed.), Baculovirus Expression Protocols (The Humana Press, Inc. 1995), and by Lucknow, "Insect Cell Expression Technology," in *Protein Engineering: Principles and Practice*, Cleland et al. (eds.), pages 183–218 (John Wiley & Sons, Inc. 1996). Established methods for isolating recombinant proteins from a baculovirus system are described by Richardson (ed.), *Baculovirus Expression Protocols* (The Humana Press, Inc. 1995).

Figure 1B:
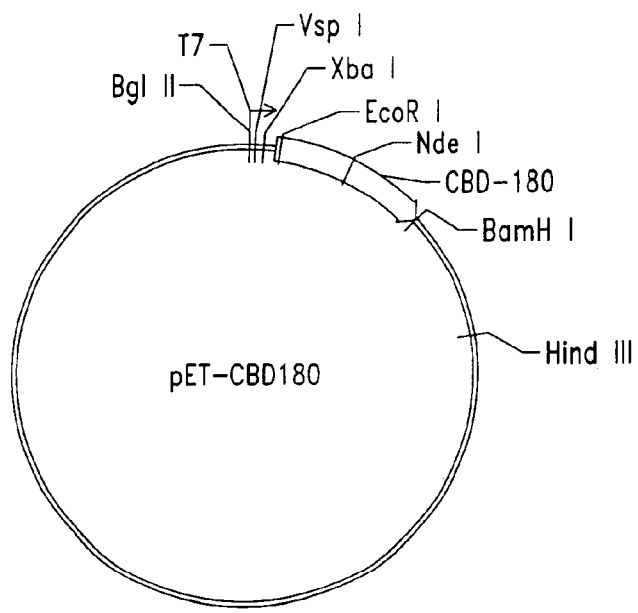
Figure 1C:
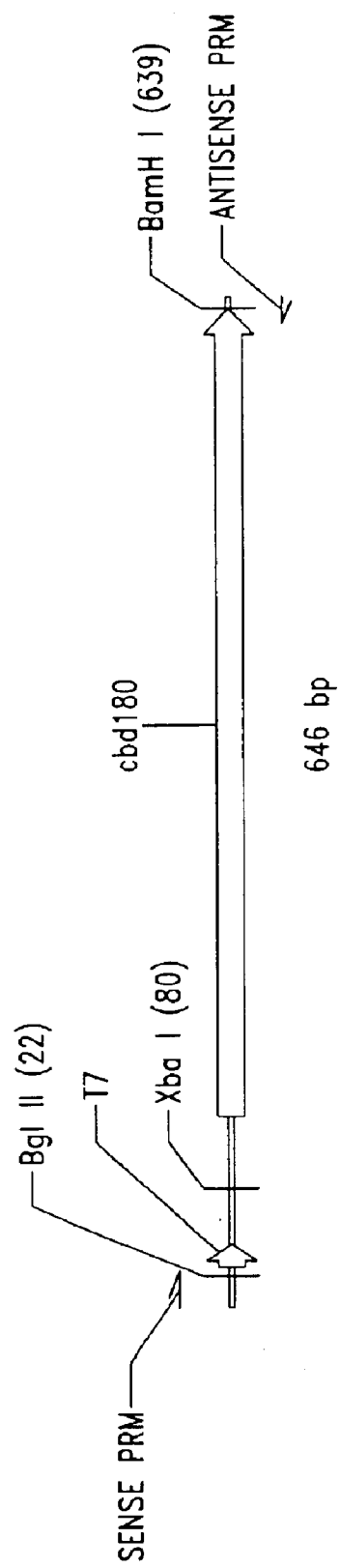
Figure 1D:
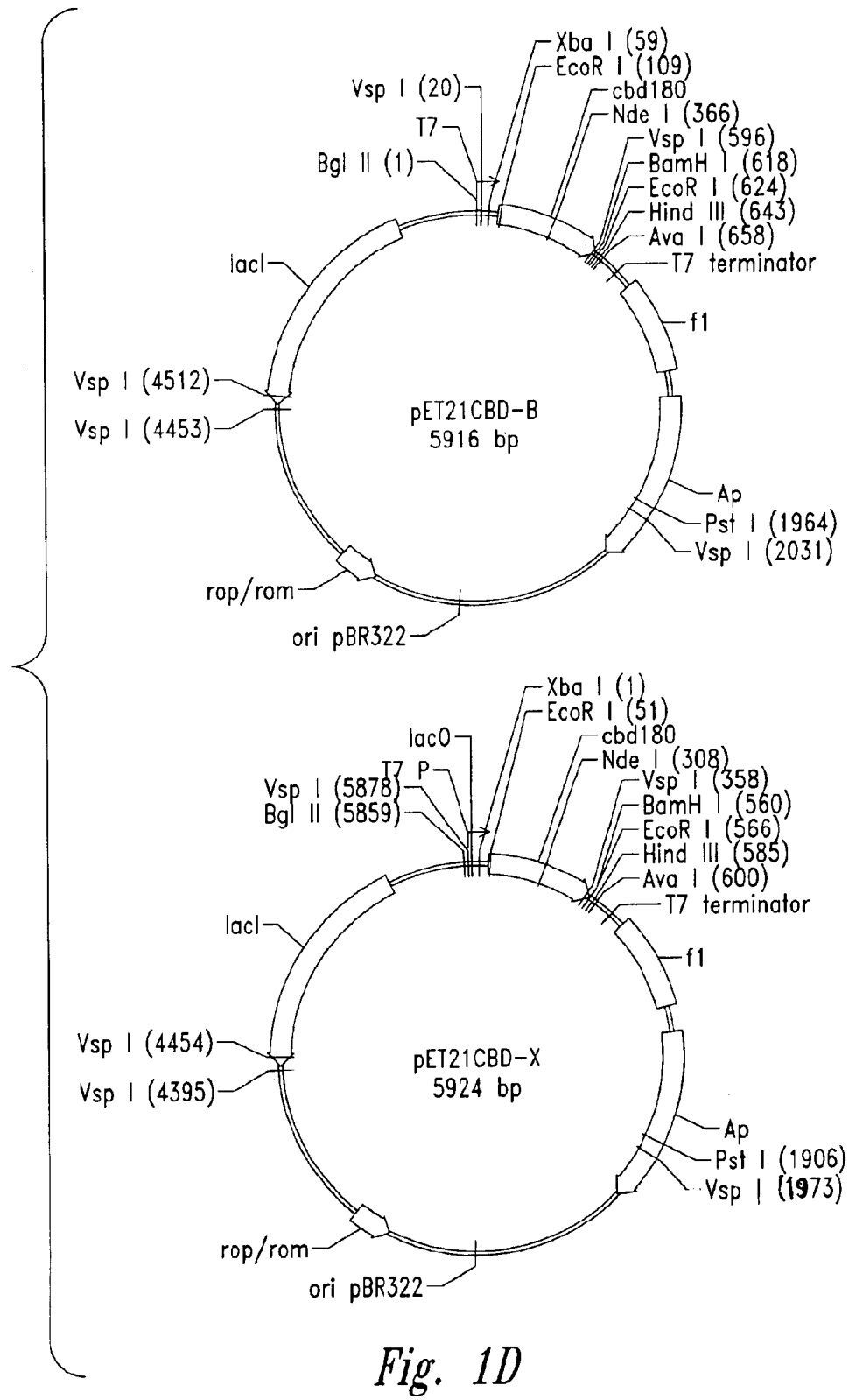

The recombinant host cells are cultured according to means known in the art to achieve optimal cell growth. In the case of recombinant bacterial hosts, preferably *E. coli*, the bacteria are introduced into a suitable culture medium containing nutrient materials that meet growth requirements. After inoculation, the bacteria continue to divide and grow until reaching a concentration, saturation density. For example, shake flask fermentation may require 15–17 hours at 30° C. to reach this point. Then the bacteria are diluted 1:3 in fresh medium and allowed to grow to mid or late exponential phase, at which time synthesis of the cationic peptide is induced. There are several methods of inducing the bacteria to synthesize the relevant recombinant proteins. Suitable induction conditions will vary with the strain of *E. coli* and the plasmid it contains. For example, in the case of temperature-dependent induction, the induction is obtained by raising the temperature to 42° C. and maintaining it from about 1 to about 5 hours at a preferred pH range of 6.5–7.2. When the expression of the desired gene reaches optimum levels the bacteria are harvested and the cells are either frozen or continue through the recovery process.

b. Illustrative Vectors Having a Nucleotide Sequence Encoding a Carrier Protein-Cationic Peptide As described in detail in the examples, plasmids were constructed that contained illustrative carrier protein genes. Briefly, plasmid vector pET21 a(+), a T7 expression plasmid (Novagen Corporation, USA), was used as the core plasmid for initial studies (FIG. 1A). Plasmid pET-CBD180 (see Shpigel et al., Biotech. Bioeng. 65:17–23, 1999) was used as the source for the gene encoding the cellulose binding domain (CBD) carrier protein (FIG. 1B). A PCR reaction was designed to amplify a fragment containing the CBD 180 gene from pET-CBD 180 as a 646 bp fragment (FIG. 1C). A BamHI restriction site (GGATCC) was incorporated at the 3'-end of the CBD 180 PCR fragment. The BglII or XbaI sites of pET-CBD 180 and BamHI were used to cleave the PCR fragment and two fragments were separately ligated into pET21 a(+) resulting in two plasmids pET21CBD-B and pET21CBD-X, respectively (FIG. 1D). Plasmid pET21CBD-X contains lacO from pET21a(+), which improves the regulation of the T7 expression system. Both plasmids contain a stop codon downstream of BamHI to allow expression of CBD180 protein. A T7 expression system was prepared in *E. coli* MC4100 based on pGP1-2, which carries the T7 RNA polymerase gene under a $\lambda_R$ promoter controlled by cI857 thermo-sensitive repressor. CBD180 protein was expressed at high levels in both systems. Plasmid pET21CBD-X was used for subsequent studies.

Figure 2:
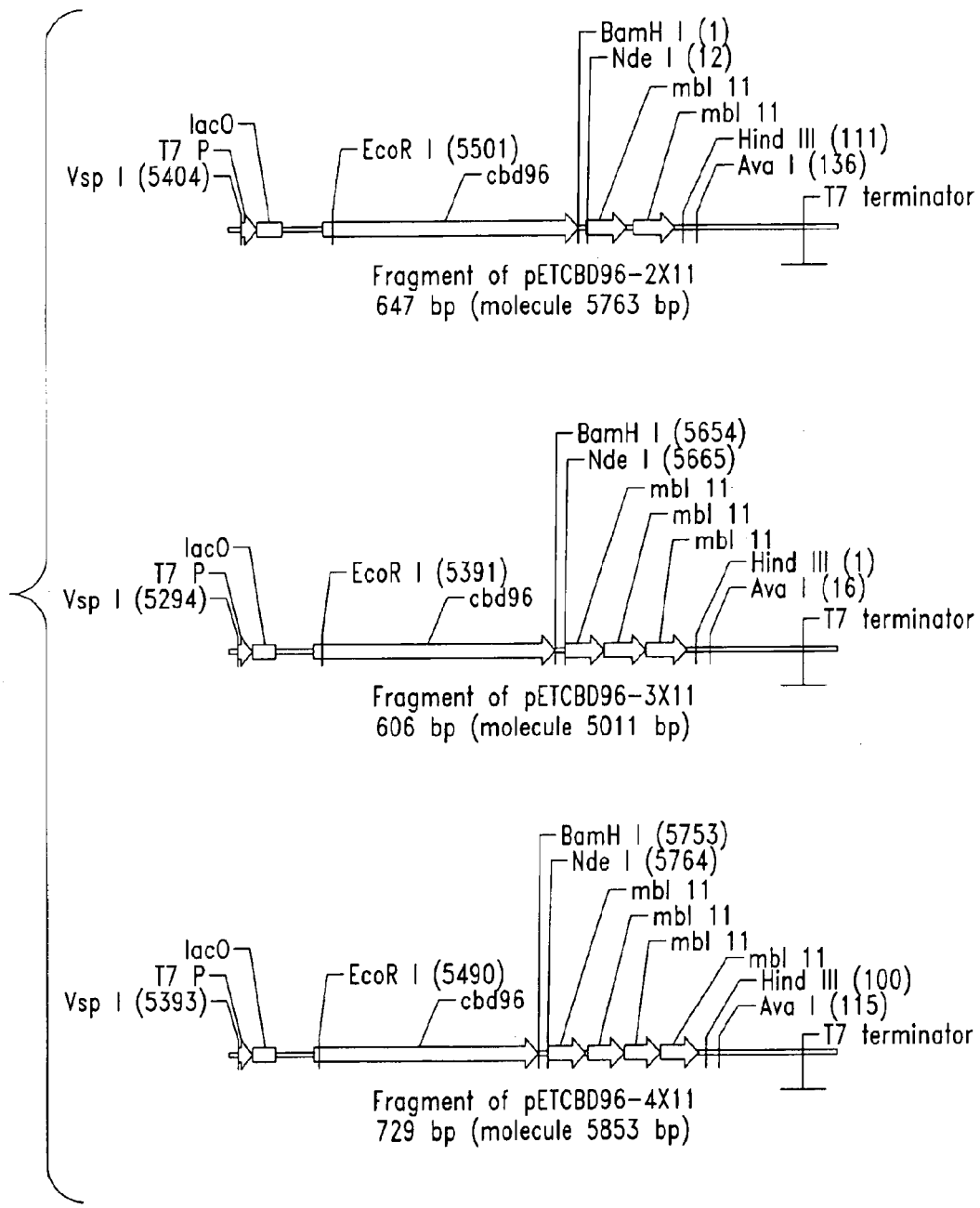
FIG. 2 shows maps of fusion poly cationic peptide genes.
Figure 3:
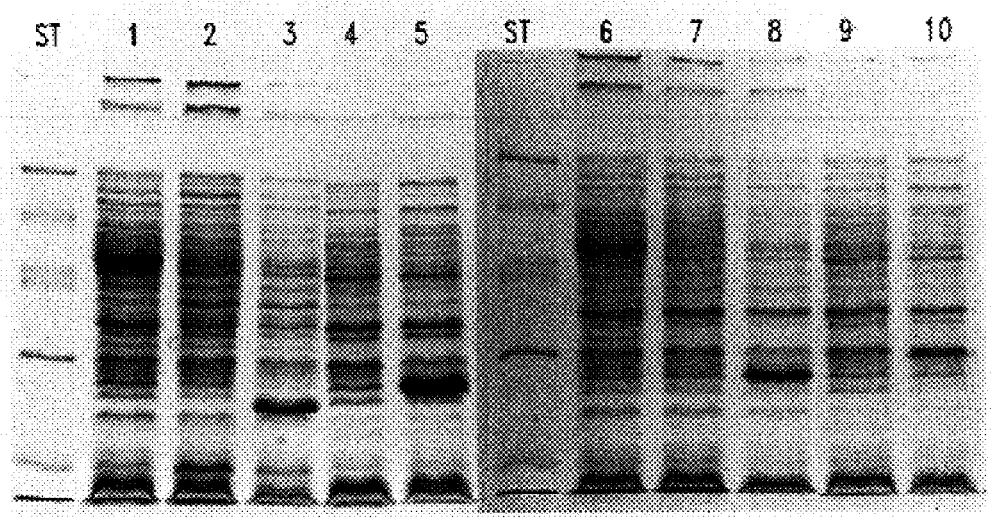
FIG. 3 is an SDS-PAGE analysis showing the expression of different CBD-poly-MBI-11 fusion proteins. Column ST: molecular weight markers: 14.4, 21.5, 31, 45, 66.2 and 97.4 kDa; Column 1: whole cell lysate of *E. coli* MC4100 (pGP1-2) cultivated at 30° C.; Column 2: whole cell lysate of *E. coli* MC4100 (pGP1-2, pET21CBD96-11) cultivated at 30° C.; Column 3: whole cell lysate of induced *E. coli* MC4100 (pGP1-2, pET21CBD96-11) at 42° C.; Column 4: whole cell lysate of *E. coli* MC4100 (pGP1-2, pET21CBD96-2x11) cultivated at 30° C.; Column 5: whole cell lysate of induced *E. coli* MC4100 (pGP1-2, pET21CBD96-2x11) at 42° C.; Column 6: whole cell lysate of *E. coli* MC4100 (pGP1-2) cultivated at 30° C.; Column 7: whole cell lysate of *E. coli* MC4100 (pGP1-2, pET21CBD96-3x11) cultivated at 30° C.; Column 8: whole cell lysate of induced *E. coli* MC4100 (pGP1-2, pET21CBD96-3x11) at 42° C.; Column 9: whole cell lysate of *E. coli* MC4100 (pGP1-2, pET21CBD96-4x11) cultivated at 30° C.; Column 10: whole cell lysate of induced *E. coli* MC4100 (pGP1-2, pET21CBD96-4x11) at 42° C.

Indolicidin is a natural 13-amino acid antimicrobial cationic peptide present in the cytoplasmic granules of bovine neutrophils and has a unique composition consisting of 39% tryptophan and 23% proline. Initial studies used two cationic peptides derived from modifications of indolicidin, MBI-11 peptide (I L K K W P W W P W R R K) and MBI-11B7 peptide (I L R W P W W P W R R K), as described by Falla et al., WO 97/08199, and by Fraser et al., WO 98/07745. A gene encoding the indolicidin-type cationic peptide MBI-11 was synthesized with BamHI and HindIII cloning sites, fused to CBD180 carrier protein and expressed. The level of expression was high and equal to that of CBD180 alone. Next, a tandem of two MBI-11 genes (2×11) was fused to CBD180, and again high expression was achieved. In order to increase the ratio of cationic peptide to carrier protein, the 177 amino acids of CBD180 were truncated to 96 amino acids, and this version of the carrier protein, designated CBD96, was used as a new carrier protein. The DNA fragment carrying CBD96 was prepared by PCR, using pET-CBD180 as a template, and cloned into pET21a(+) resulting in plasmid pET21CBD96. Both single and double copies of the MBI-11 gene were fused to CBD96 and expressed at high levels. Then poly genes containing up to ten MBI-11 units were prepared. However, expression was only achieved with a fusion protein containing four MBI-11 genes in tandem. A dramatic decrease in expression was encountered when the number of genes exceeded three (FIGS. 2 and 3.)

c. Illustrative Vectors Having a Nucleotide Sequence Encoding a Carrier Protein-Cationic Peptide With Anionic Spacers In another approach, vectors were constructed comprising multi-domain fusion proteins with small anionic peptide spacers between the cationic peptide domains. This method of construction of multi-domain genes allows the polymerization of any cationic peptide gene without changing its amino acid sequence. In initial studies, the MBI-11B7 cationic peptide was used.

Figure 4:
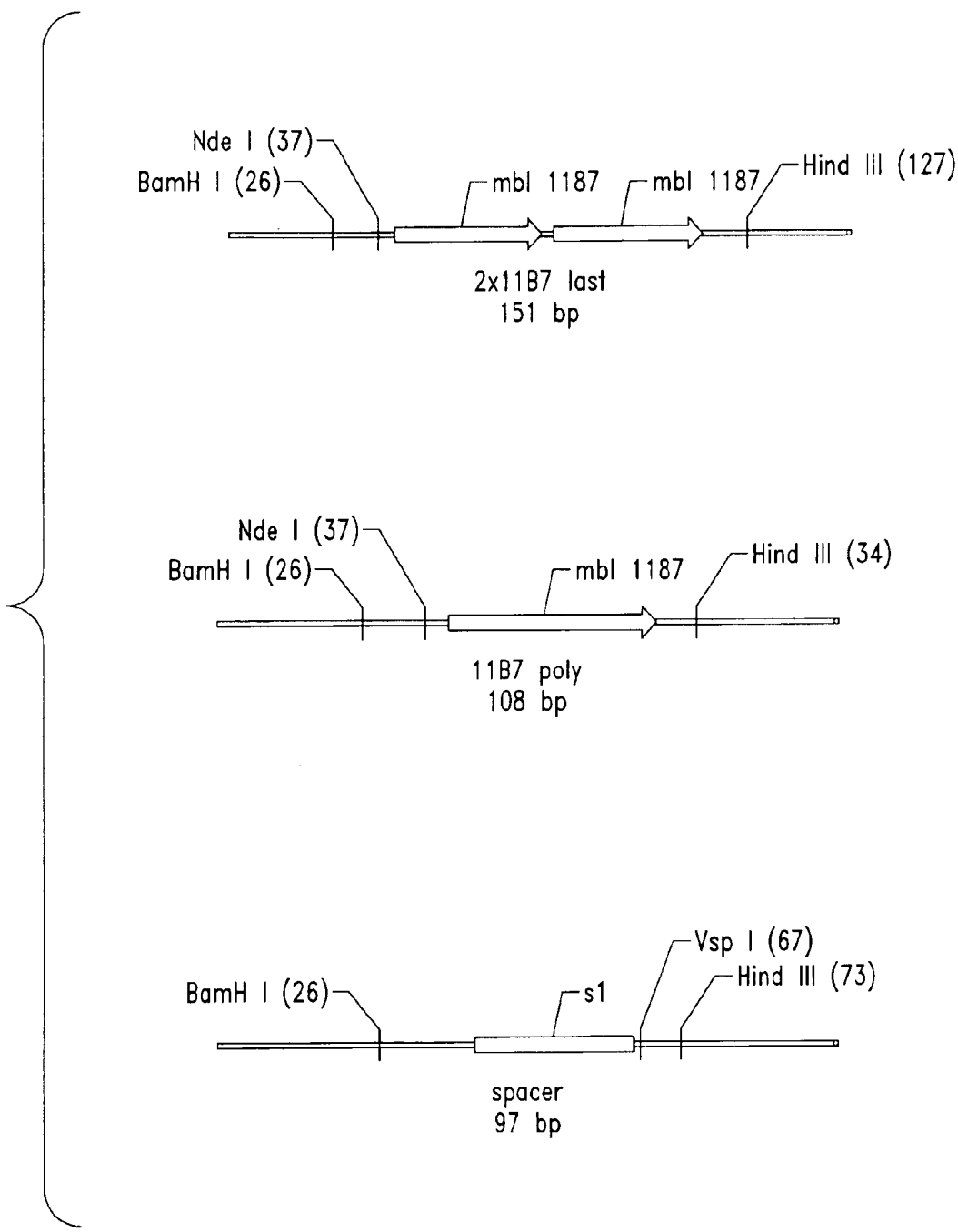
FIG. 4 shows maps of cassettes used for construction of genes of multi-domain proteins.
Figure 5:
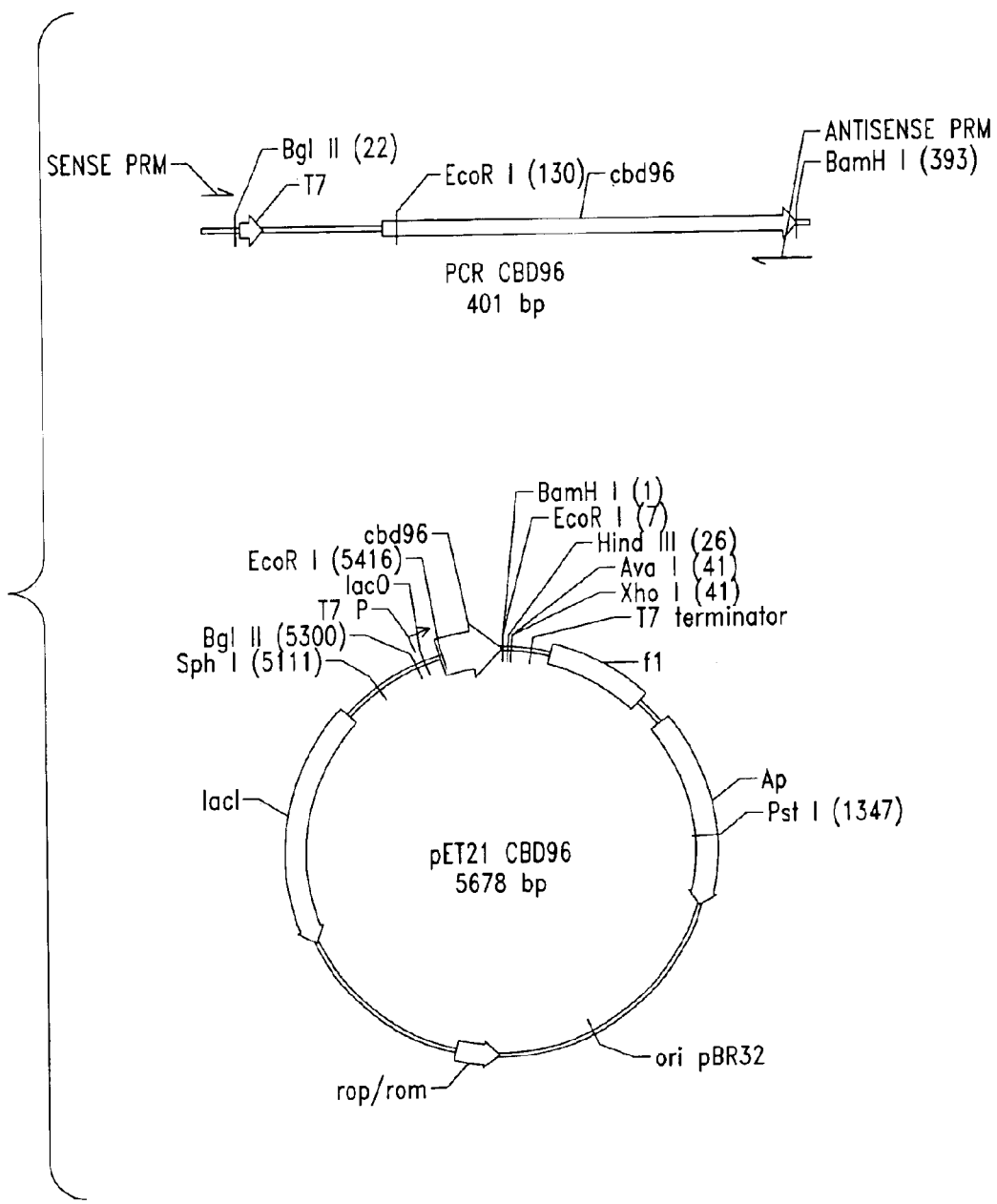
FIG. 5 presents maps of plasmid pET21CBD96 and one of its inserts.
Figure 6A:
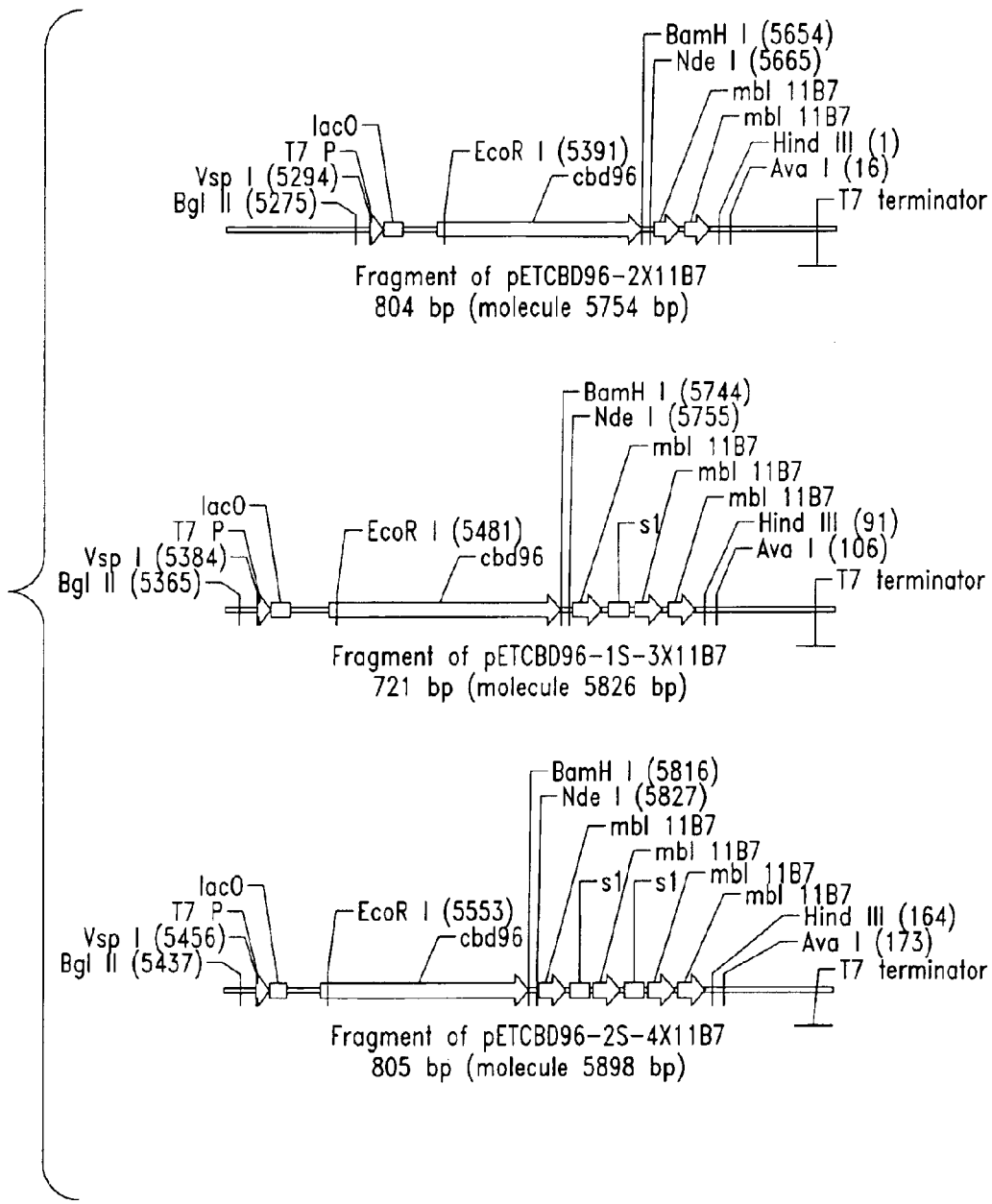
FIG. 6 shows maps of fusion multi-domain protein genes.
Figure 6B:
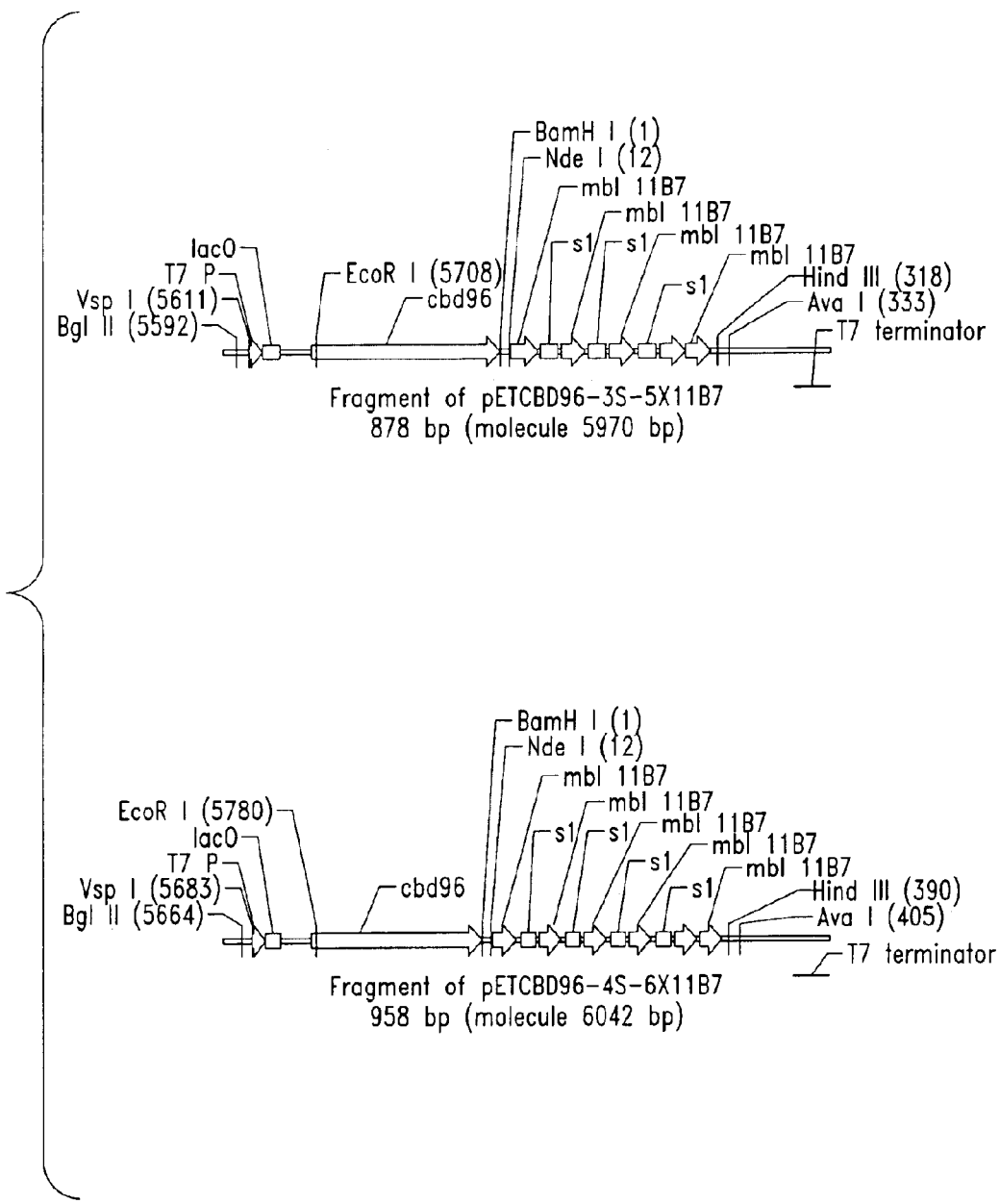
Figure 6C:
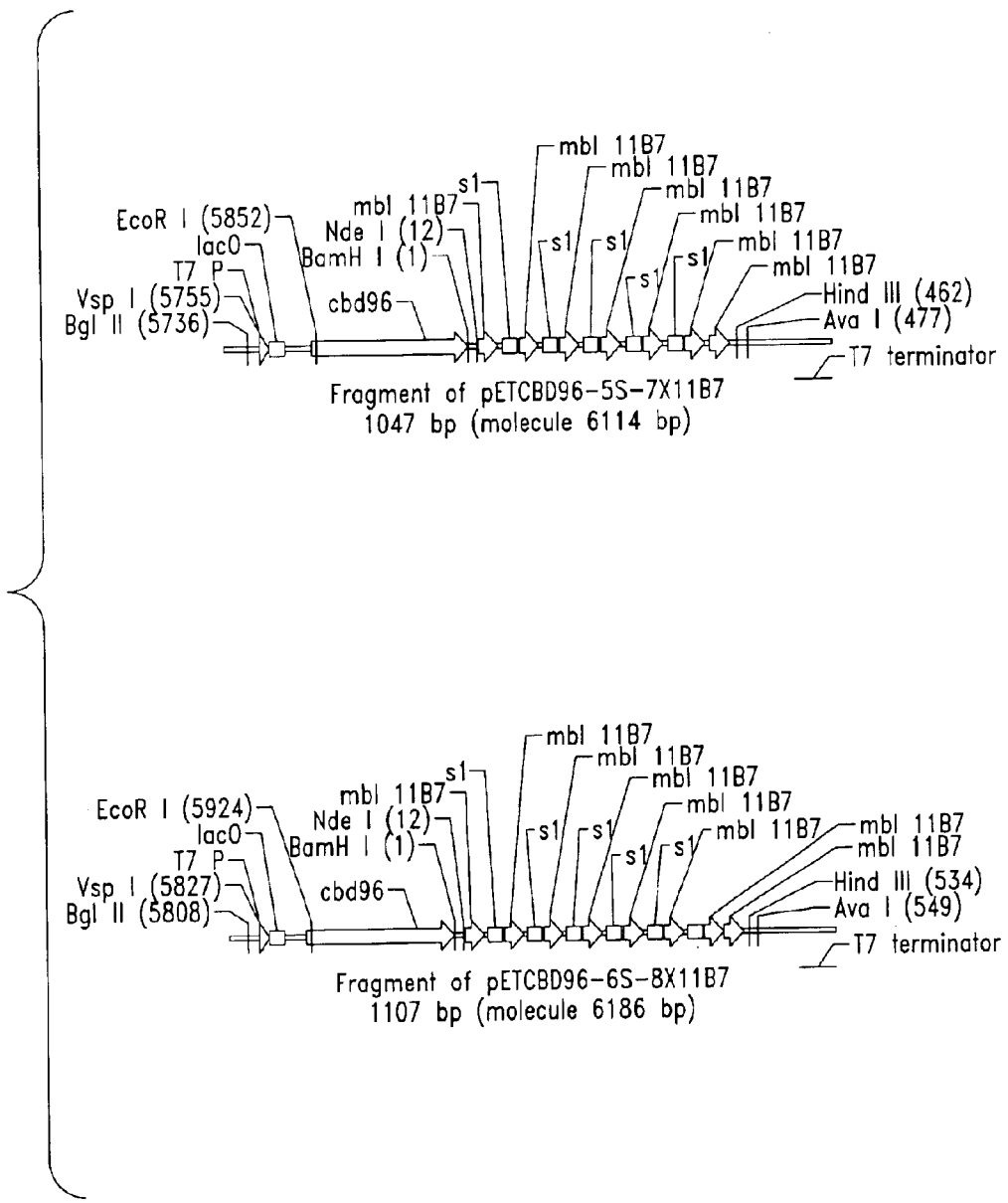
Figure 7:
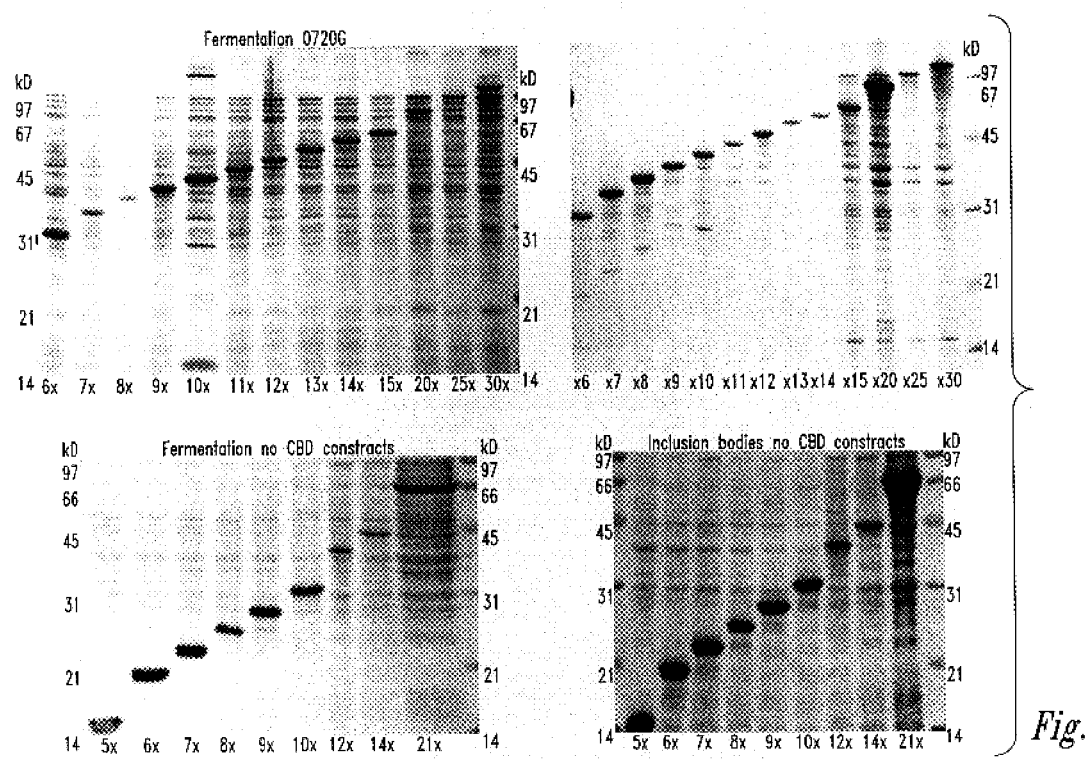
FIG. 7 is SDS-PAGE analyses showing the results of fermentation of multi-domain clones having five or more MBI-11B7 copies. The upper panels represent the multidomain clones fused to CBD carrier. The lower panels show the multi-domain clones carrier-free. The left panels show the whole cell lysates, where the right side panels show the inclusion bodies partitioning step. The major band in each lane represents the relevant multidomain protein and the "x" numbers appearing at the bottom of each lane indicate the number of the MBI- peptide copies. Numbers appearing along the left edge of the gels represents molecular weight standards (kD).
Figure 8:
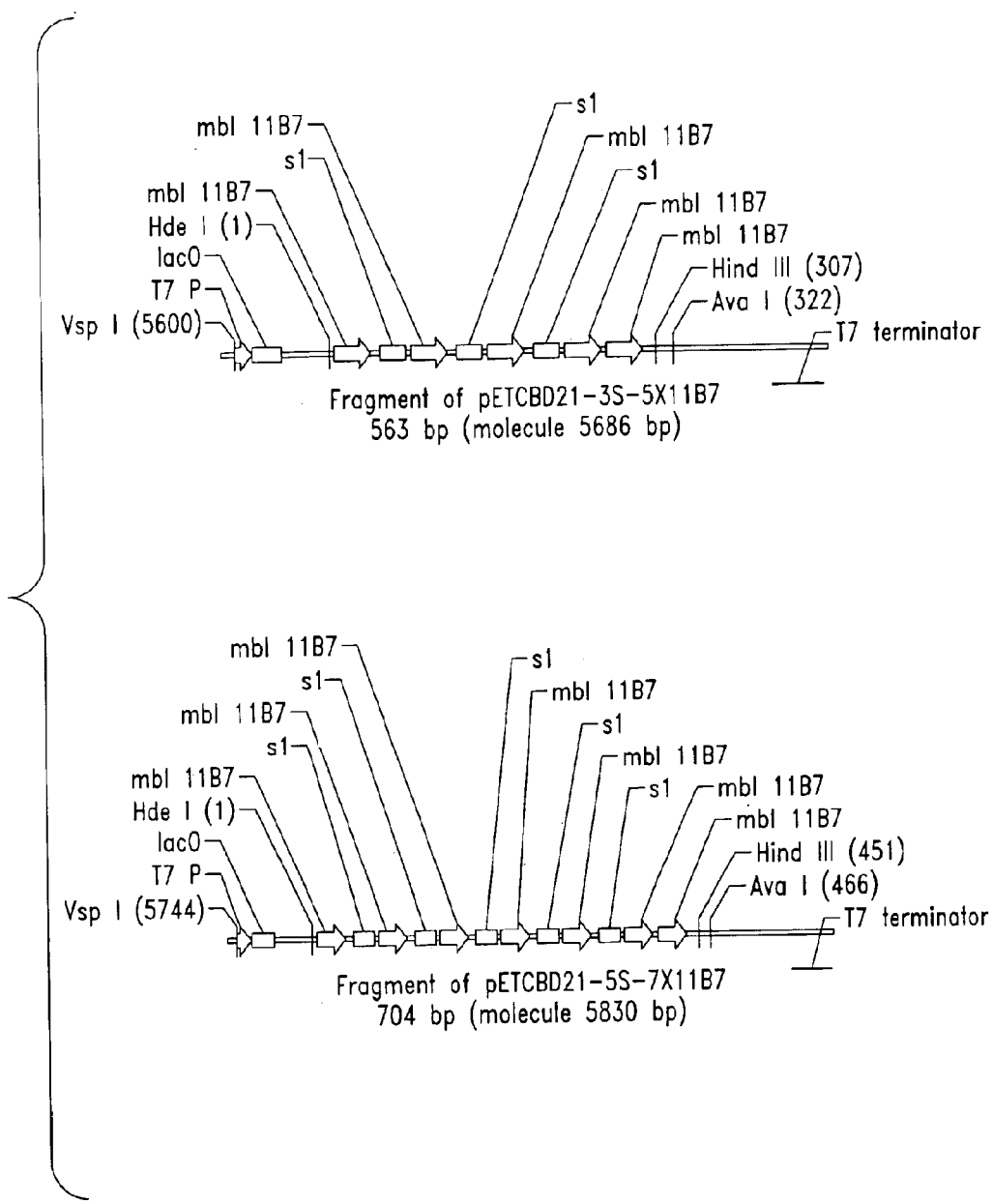
FIG. 8 shows maps of portions of plasmids pET21-3s-5x11B7 and pET21-5s-7x11B7.

Three distinct DNA cassettes specifying MBI-11B7 cationic peptide genes and a negatively charged peptide spacer were synthesized: 11B7-poly, anionic spacer, and 2x11B7-last (FIG. 4), and cloned into appropriate plasmid vectors. Cassettes of 11B7-poly and spacer were linked together resulting in the 11B7poly-spacer cassette. The anionic spacer peptide and cationic peptide genes were separated by codons for Met to create sites for cleavage by cyanogen bromide (CNBr). Two codons, specifying Ala and a stop codon, were linked to the last 2x11B7 gene. The 2x11B7-last cassette was then cloned downstream of the gene encoding CBD96 in pET21CBD96 (FIG. 5) resulting in plasmid pET21CBD96x11B7. This plasmid was later used in the construction of several fused multi-domain genes. The 11B7poly-spacer cassette was used in a serial cloning procedure which allowed polymerization of 11B7 genes into multi-domain fusion CBD96-spacer-poly 11B7 proteins in the pET21CBD96 expression system (FIG. 6). All multi-domain constructs containing n copies (where n=3 to 30) of MBI-11B7 genes and (n–2) spacers were expressed at high levels. Examples of expression are shown in FIG. 7. In order to accelerate the serial cloning procedure a polymerization cassette containing five 11B7 domains and five anionic spacer domains was prepared and used for construction of multidomain genes containing more than fifteen 11B7 domains (i.e., 20 copies, 25, 30, etc.). This cassette has an anionic spacer domain at the end followed by a stop codon. Use of this cassette allowed construction of CBD96-based multi-domain systems containing equal numbers of 11B7 and spacer domains.

d. Illustrative Vectors Having a Nucleotide Sequence Encoding a Cationic Peptide With Anionic Spacers, But Lacking a Carrier Protein One series of the multi-domain proteins comprises n times MBI-11B7 peptides and n–2 anionic spacer peptides. When n=5, the molecular weight of the multi-domain protein equals 13.46 kDa, which should be sufficiently large for expression in $E.\ coli$. DNA fragments containing multi-domain genes of approximately this size were excised from relevant plasmids using restriction endonucleases NdeI and HindIII and fused into plasmid containing specifically designed leader 11B7 domain. In $E.\ coli$, the first methionine in all proteins is translated as formyl-methionine which cannot be cleaved by CNBr. Accordingly, the carrier-free multi-domain proteins were modified in such a way that the first domain begins with M-T-M amino acids, allowing CNBr to cleave the first peptide at the second methionine and release authentic peptide. The relevant portions of plasmids pET21-3S-5x11B7 and pET21-5S-7x11B7 are shown in FIG. 8. All of the carrier-free multi-domain constructs containing from 5 to 14 copies of MBI-11B7 genes were expressed at high levels as shown in FIG. 7. In the same way, constructs were prepared containing an equal number of 11B7 and anionic spacer domains with a spacer sequence at the end. They were also expressed at high levels. The theoretical yield of the MBI-11 B7 peptide, within experimentally obtained multi-domain proteins, can be seen in Table 2.

The invention also provides an additional example of another antimicrobial cationic peptide (MBI-26), twice the size of the peptide described above (MBI-11B7), consisting of 26 amino acids, where seven of them are basic amino acids. This peptide was artificially designed by a fusion between selected sequences of the natural antimicrobial cationic peptides cecropin and melittin. In the present invention, the last amino acid serine at the carboxy end was replaced with a methionine residue, which was used for release of the peptide from the multi-domain protein. The production of this peptide was obtained by recombinant synthesis in host cells, using the multi-domain protein method, as described above for MBI-11B7 peptide. Details are provided in Example 8.

TABLE 2

SUMMARY OF SUCCESSFULLY EXPRESSED CONSTRUCTS*
AND THEIR THEORETICAL MBI-11B7CATIONIC PEPTIDE RATIO
IN THE MULTI-DOMAIN PROTEINS,
WITH AND WITHOUT CARRIER PROTEIN

| Construct | Multi-domain Protein Mass (Da) | % Cationic Peptide per Multi-domain Protein (Da/Da) |
|---|---|---|
| With Carrier Protein | — | — |
| PET21CBD-11B7 | 21,249 | 8.9 |
| pET21CBD-2x11B7 | 23,142 | 16.5 |
| pET21CBD96-11B7 | 12,697 | 15.0 |
| pET21CBD96-2x11B7 | 14,590 | 26.1 |
| pET21CBD96-1S-3x11B7 | 17,718 | 32.3 |
| pET21CBD96-2S-4x11B7 | 20,845 | 36.6 |
| pET21CBD96-3S-5x11B7 | 23,973 | 39.8 |
| pET21CBD96-4S-6x11B7 | 27,101 | 42.2 |
| pET21CBD96-5S-7x11B7 | 30,228 | 44.2 |
| pET21CBD96-6S-8x11B7 | 33,356 | 45.8 |
| pET21CBD96-7S-9x11B7 | 36,484 | 47.1 |
| pET21CBD96-8S-10x11B7 | 39,612 | 48.2 |
| pET21CBD96-9S-11x11B7 | 42,739 | 49.1 |
| pET21CBD96-10S-12x11B7 | 45,867 | 49.9 |
| pET21CBD96-11S-13x11B7 | 48,995 | 50.6 |
| pET21CBD96-12S-14x11B7 | 52,122 | 51.3 |
| pET21CBD96-13S-15x11B7 | 55,250 | 51.8 |
| pET21CBD96-18S-20x11B7 | 70,888 | 53.9 |
| pET21CBD96-23S-25x11B7 | 86,527 | 55.1 |
| pET21CBD96-28S-30x11B7 | 102,162 | 56.1 |
| With equal spacers number | — | — |
| pET21CBD96-5S-5x11B7 | 26,282 | 36.3 |
| pET21CBD96-10S-10x11B7 | 41,921 | 45.5 |
| pET21CBD96-15S-15x11B7 | 57,559 | 48.9 |
| Without Carrier Protein | — | — |
| pET21-3s-5x11B7-F | 13,692 | 69.7 |
| pET21-4s-6x11B7-F | 16,820 | 68.1 |
| pET21-5s-7x11B7-F | 19,947 | 67.0 |
| pET21-6s-8x11B7-F | 23,075 | 66.2 |
| pET21-7s-9x11B7-F | 26,203 | 65.6 |
| pET21-8s-10x11B7-F | 29,330 | 65.1 |
| pET21-9s-11x11B7-F | 32,458 | 64.7 |
| pET21-10s-12x11B7-F | 35,586 | 64.4 |
| pET21-11s-13x11B7-F | 38,713 | 64.1 |
| pET21-12s-14x11B7-F | 41,841 | 63.9 |
| pET21-19s-21x11B7-F | 63,735 | 61.9 |
| With equal spacers number | — | — |
| pET21-6s-6x11B7-F | 19,129 | 59.9 |
| PET21-11s-11x11B7-F | 34,767 | 60.4 |
| pET21-16s-16x11B7-F | 50,405 | 60.6 |

*Examples of the expression can be seen in FIG. 7.

4. Purification and Assay of Cationic Peptides Produced by Recombinant Host Cells General techniques for recovering protein produced by a recombinant host cell are provided, for example, by Grisshammer et al., "Purification of over-produced proteins from $E.\ coli$ cells," in *DNA Cloning 2: Expression Systems, 2nd Edition*, Glover et al. (eds.), pages 59–92 (Oxford University Press 1995), Georgiou, "Expression of Proteins in Bacteria," in *Protein Engineering: Principles and Practice*, Cleland et al. (eds.), page 101 (John Wiley & Sons, Inc. 1996), Richardson (ed.), *Baculovirus Expression Protocols* (The Humana Press, Inc. 1995), and by Etcheverry, "Expression of Engineered Proteins in Mammalian Cell Culture," in *Protein Engineering: Principles and Practice*, Cleland et al. (eds.), pages 163 (Wiley-Liss, Inc. 1996). Variations in cationic peptide isolation and purification can be devised by those of skill in the art, including, for example, affinity chromatography, size exclusion chromatography, ion exchange chromatography, HPLC and the like (see, for example, Selsted, "HPLC Methods for Purification of Antimicrobial Peptides," in *Antibacterial Peptide Protocols*, Shafer (ed.) (Humana Press, Inc. 1997)). Particular purification methods are described below.

The present invention provides a novel, scaleable, cost-effective purification process for recombinant production of cationic peptides in host cells. The multi-domain fused polypeptide forms an insoluble complex in E. coli called the inclusion body. After the bacteria are mechanically disrupted, these inclusion bodies can be separated from the soluble components of the cell, according to means known in the art such as filtration or precipitation. Host impurities can be removed using solvents such as detergent (Triton X-100), enzyme (lysozyme, DNAse) and salt.

Cationic peptides can be released from anionic spacer peptides and carrier protein (such as truncated CBD) using standard techniques. If methionine residues have been included at desired cleavage points, for example, chemical cleavage with cyanogen bromide (CNBr) reagent in an acidic environment can be used. The reaction can be performed in 70% formic acid or 70% formic acid and 0.1 N HCl or 70% TFA (trifluoroacetic acid). At the end of the reaction, which can last 4–15 hours, the reaction mixture is diluted in water, preferably 15 times the volume of the reaction mixture, and then dried. At this stage, the carboxyl terminus of the cationic peptide is present as homoserine lactone.

Figure 9:
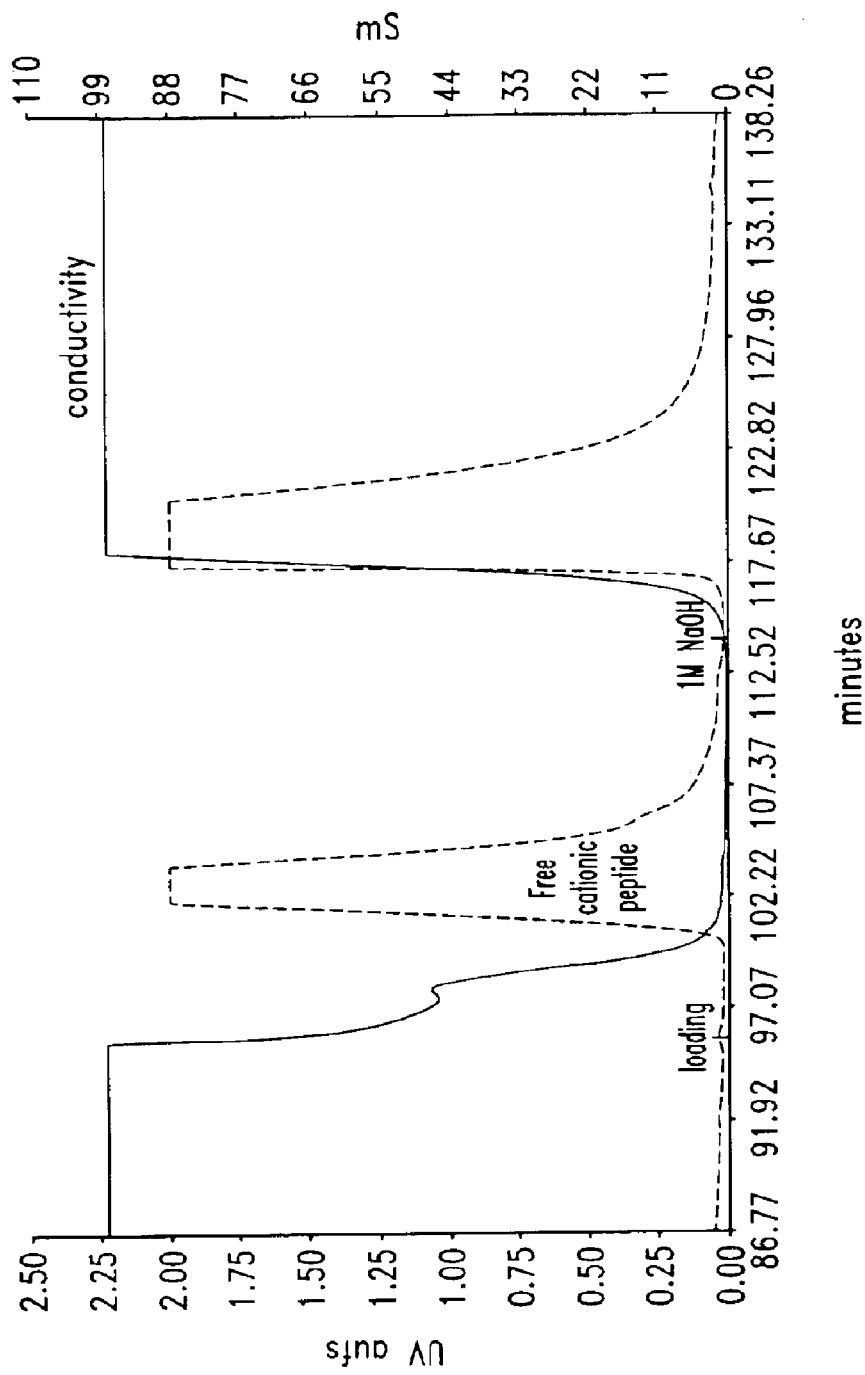
FIG. 9 is a chromatogram of the Q-Sepharose chromatography step for cationic peptide purification, which monitors UV absorbance at 280 nm and conductivity.

The isoelectric point of polycationic peptides is very high (10.5–12.5) which enables the development of a very unique purification process using an anion exchange chromatography column under unusual conditions. Almost any anion exchange resin coupled to weak or strong cation ligand, particularly those used for industrial purpose to purify proteins, peptides, carbohydrates and nucleic acids, can be used in the following purification process for cationic peptides. This procedure requires the use of only one chromatography step to obtain 95% purification. The advantages of this chromatography are that it is short, fast, does not require high pressure equipment and can be performed without organic solvents. The preferred procedure relies on dissolving the dried cleavage materials in 7–8 M urea (alternatively in 50% ethanol or water) and loading them onto an anion exchange column. At this stage, the pH of the loading sample is acidic (pH 2-3). The column is previously washed with two column volumes of 0.5–1 M NaOH and one short wash in water to a conductivity of less than 10 mS, preferably less than 1 mS, detected at the exit of the column. If the dried cleavage materials have been dissolved in 8 M urea, one column wash with 8 M urea before loading is preferred. The cationic peptide, in contrast to the impurities, passes through the column whereas the impurities are bound to the resin and thus separated (FIG. 9). At this stage, the carboxy terminus of the cationic peptide has been converted and appears as homoserine. In addition, the pH of the cationic peptide sample has changed from acidic to basic (above pH 11).

If the dried cleavage materials loaded on the anion exchange column are in the presence of 7–8 M urea, the flow through purified peptide will be in urea solution, which can be separated and further purified by high-throughput reverse phase chromatography using the perfusive supports Poros 20 or 50 R-2 resin (PerSeptive Biosystems Inc.). For mass production, Poros 50 is preferred due to better flow and the fact that the use of high pressure equipment is avoided.

Another more common, but more expensive procedure can be performed according to means known in the art, such as reverse phase chromatography where the dried cleavage materials may be dissolved in water or 0.1% TFA and loaded onto a C8 or C18 column using the RP-HPLC technique. However, this method requires high pressure equipment and organic solvents and results in a cationic peptide with a C-terminal homoserine lactone.

In the studies described above, the recombinant cationic peptide MBI-11B7 was obtained from a multi-domain construct. As a result, CNBr cleavage causes the formation of a homoserine lactone residue at the carboxy end which may be easily converted to homoserine by raising the pH. This carboxy terminus is different from the bactericidal amidated chemical synthetic MBI-11B7CN. Hence, the antimicrobial activity was compared between chemically and recombinantly synthesized cationic peptide.

There are various in vitro methods for determining the activity of a cationic peptide, including an agarose dilution MIC assay, a broth dilution, time-kill assay, or equivalent methods (see, for example, Shafer (ed.), *Antibacterial Peptide Protocols* (Humana Press, Inc. 1997)). Antibiotic activity is typically measured as inhibition of growth or killing of a microorganism or a microorganism-infected cell.

For example, a cationic peptide is first dissolved in Mueller Hinton broth supplemented with calcium and magnesium, and then this solution is mixed with molten agarose. Other broth and agars may be used as long as the peptide can freely diffuse through the medium. The agarose is poured into petri dishes or wells and allowed to solidify, and a test strain is applied to the agarose plate. The test strain is chosen, in part, based on the intended application of the peptide. Plates are incubated overnight and inspected visually for bacterial growth. A minimum inhibitory concentration (MIC) of a cationic peptide is the lowest concentration of peptide that completely inhibits growth of the organism. Peptides that exhibit acceptable activity against the test strain, or group of strains, typically having an MIC of less than or equal to 16 $\mu$g/ml, can be subjected to further testing.

Alternatively, time kill curves can be used to determine the differences in colony counts over a set time period, typically 24 hours. Briefly, a suspension of organisms of known concentration is prepared and a cationic peptide is added. Aliquots of the suspension are removed at set times, diluted, plated on medium, incubated, and counted. MIC is measured as the lowest concentration of peptide that completely inhibits growth of the organism.

Cationic peptides may also be tested for their toxicity to normal mammalian cells. An exemplary assay is a red blood cell (RBC) (erythrocyte) hemolysis assay. Briefly, in this assay, red blood cells are isolated from whole blood, typically by centrifugation, and washed free of plasma components. A 5% (v/v) suspension of erythrocytes in isotonic saline is incubated with different concentrations of cationic peptide. After incubation for approximately one hour at 37° C., the cells are centrifuged, and the absorbance of the supernatant at 540 nm is determined. A relative measure of lysis is determined by comparison to absorbance after complete lysis of erythrocytes using $NH_4Cl$ or equivalent (establishing a 100% value). A peptide with less than 10% lysis at 100 g/ml is suitable. Preferably, the cationic peptide induces less than 5% lysis at 100 g/ml. Cationic peptides that are not lytic, or are only moderately lytic, are desirable and suitable for further screening. In vitro toxicity may also be assessed by measurement of toxicity towards cultured mammalian cells.

Additional in vitro assays may be carried out to assess the therapeutic potential of a cationic peptide. Such assays include peptide solubility in formulations, pharmacology in blood or plasma, serum protein binding, analysis of secondary structure, for example by circular dichroism, liposome permeabilization, and bacterial inner membrane permeabilization.

In the present case, the antimicrobial activities of MBI-11B7CN, MBI-11B7HSL (homoserine lactone form) and MBI-11B7HS (homoserine form) were tested against various gram-negative and gram-positive strains, including antibiotic resistant strains. The assay was performed as described in "Methods for Dilution Antimicrobial Susceptibility Tests for Bacteria That Grow Aerobically-Fourth Edition; Approved Standard" NCCLS document M7-A4 (ISBN 1-56238-309-4) Vol. 17, No. 2 (1977). Determination of the minimum inhibitory concentration (MIC) of the peptides, demonstrated that MBI-11B7HSL and MBI-11B7HS peptides maintain similar bactericidal activity to the amidated MBI-11B7CN peptide. See Table 3 in Example 13.

Cationic peptides can also be tested in vivo for efficacy, toxicity and the like. The antibiotic activity of selected peptides may be assessed in vivo for their ability to ameliorate microbial infections using a variety of animal models. A cationic peptide is considered to be therapeutically useful if inhibition of microorganism growth, compared to inhibition with vehicle alone, is statistically significant. This measurement can be made directly from cultures isolated from body fluids or sites, or indirectly, by assessing survival rates of infected animals. For assessment of antibacterial activity, several animal models are available, such as acute infection models including those in which (a) normal mice receive a lethal dose of microorganisms, (b) neutropenic mice receive a lethal dose of microorganisms, or (c) rabbits receive an inoculum in the heart, and chronic infection models. The model selected will depend in part on the intended clinical indication of the cationic peptide.

As an illustration, in a normal mouse model, mice are inoculated ip or iv with a lethal dose of bacteria. Typically, the dose is such that 90–100% of animals die within two days. The choice of a microorganism strain for this assay depends, in part, upon the intended application of the cationic peptide. Briefly, shortly before or after inoculation (generally within 60 minutes), cationic peptide is injected in a suitable formulation buffer. Multiple injections of cationic peptide may be administered. Animals are observed for up to eight days post-infection and the survival of animals is recorded. Successful treatment either rescues animals from death or delays death to a statistically significant level, as compared with non-treatment control animals.

In vivo toxicity of a peptide can be measured by administration of a range of doses to animals, typically mice, by a route defined in part by the intended clinical use. The survival of the animals is recorded and $LD_{50}$, $LD_{90-100}$, and maximum tolerated dose (MTD) can be calculated to enable comparison of cationic peptides.

Low immunogenicity of the cationic peptide is also a preferred characteristic for in vivo use. To measure immunogenicity, peptides are injected into normal animals, generally rabbits. At various times after a single or multiple injections, serum is obtained and tested for antibody reactivity to the peptide analogue. Antibodies to peptides may be identified by ELISA, immunoprecipitation assays, Western blots, and other methods (see, generally, Harlow and Lane, *Antibodies: A Laboratory Manual*, (Cold Spring Harbor Laboratory Press, 1988)).

Expression vectors comprising the multi-domain fusion proteins described herein can be used to produce multi-domain fusion protein representing more than 25% of the total protein of a recombinant host cell. Since the multi-domain fusion proteins comprise multiple copies of a cationic peptide gene, the cationic peptide component of a fusion protein can be practically attained as more than 50% of the fusion protein.

The present invention, thus generally described, will be understood more readily by reference to the following examples, which are provided by way of illustration and are not intended to be limiting of the present invention.

EXAMPLE 1

Construction Of Plasmids pET21CBD-X (B) and pET21 CBD96

Figure 10A:
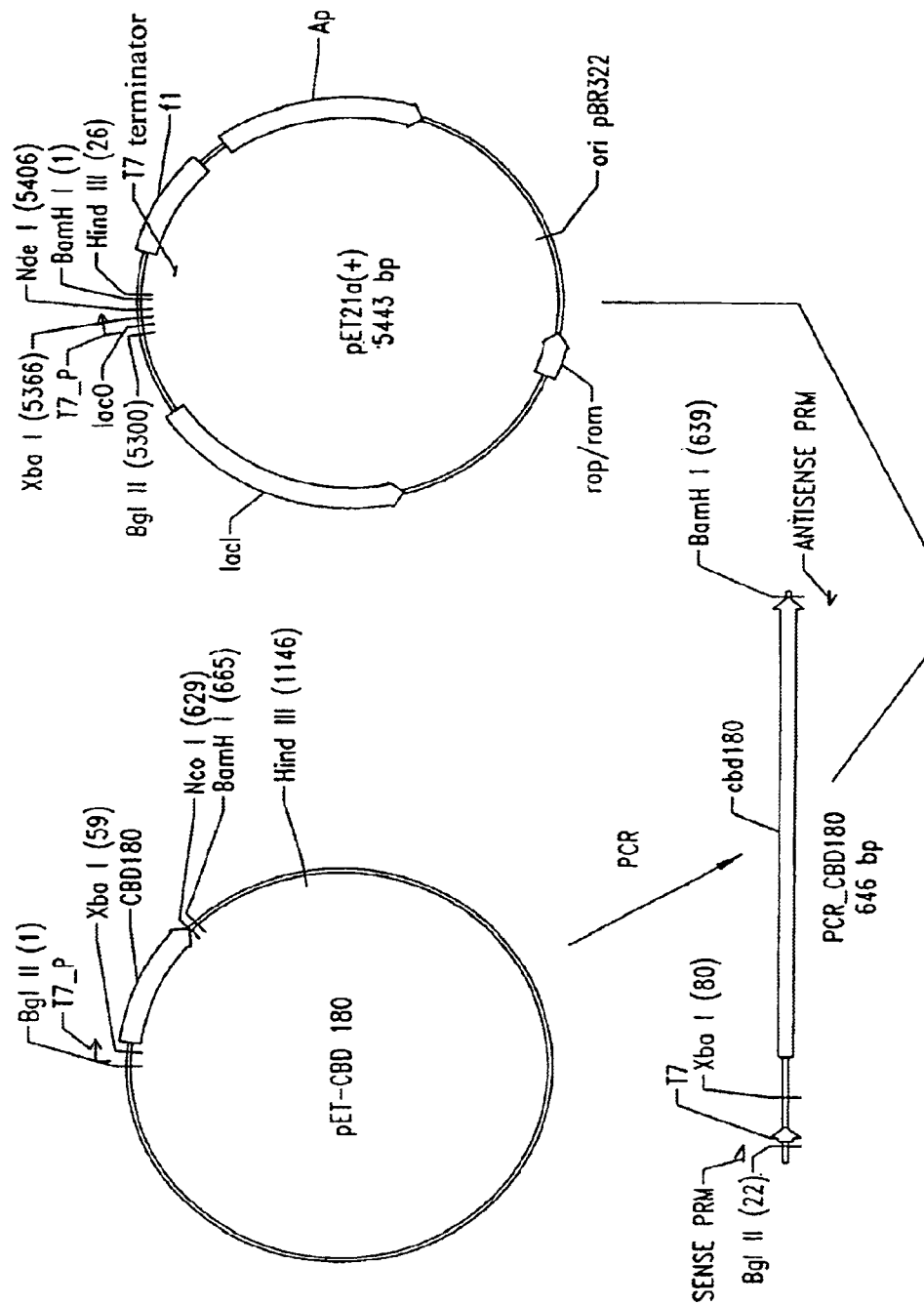
FIG. 10 is a schematic drawing that illustrates the construction of plasmids pET21CBD-X and pET21CBD-B.
Figure 10B:
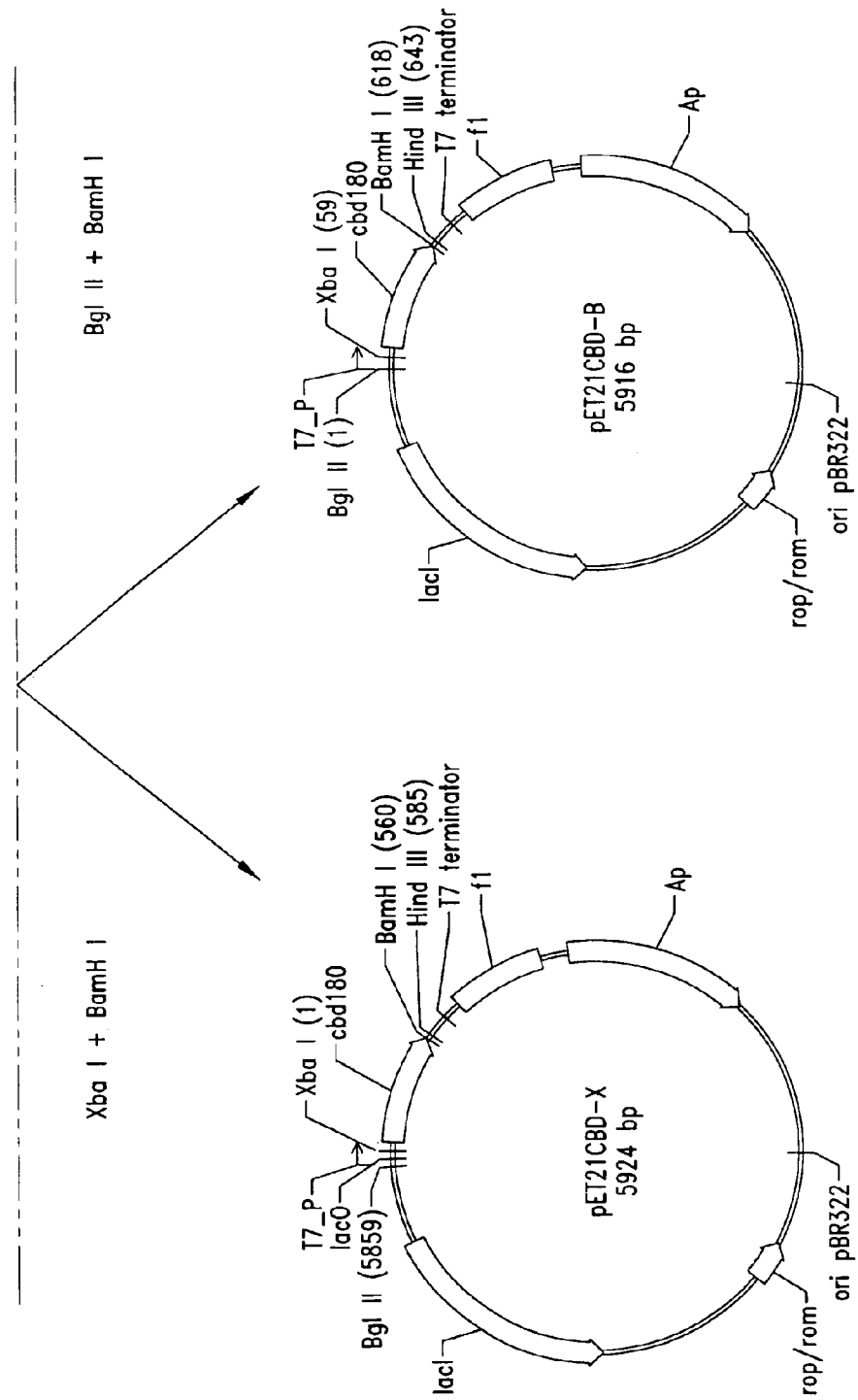
Figure 11:
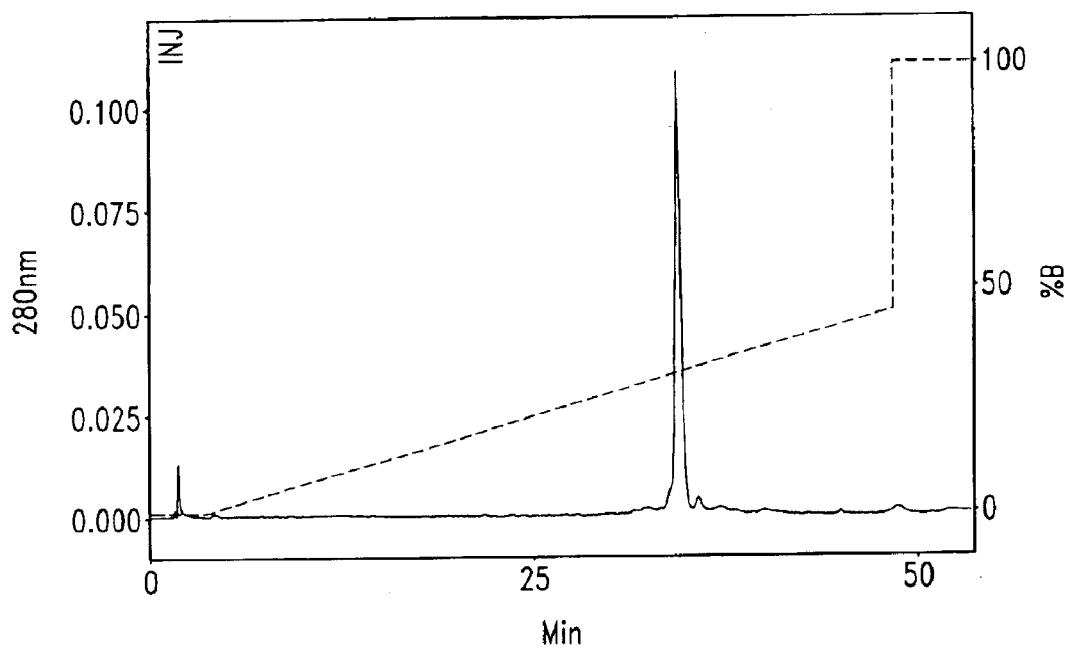
FIG. 11 is a graph showing the results of reverse-phase analysis of the Q-Sepharose chromatography leading peak, representing pure cationic peptide. In this study, a C8-column (4.6x10, Nova-Pak, Waters) was equilibrated with 0.1% TFA in water at 1 m/min flow rate. Then 50 µl of Q-Sepharose chromatography leading peak material, diluted with 50 µl equilibration solution, was loaded on the column. Elution was performed with a 0–45% gradient of solution B (0.1% TFA, 99.9% Acetonitrile) at 1% increase B per min, then step to 100% B.

Plasmid vector pET21a(+) (Novagen Corporation, USA), a T7 expression plasmid, was used as the core plasmid for all expression systems (FIGS. 1A and 10). The cellulose binding domain (CBD) from *Clostridium cellulovorans* was selected as a carrier protein for expression of antibacterial cationic peptides. Plasmid pET-CBD 180 (Shpigel et al., supra) was used as the +starting material (FIGS. 11B and 10). Restriction enzymes except VspI and NsiI (Promega Corporation, USA), T4 DNA ligase and Taq polymerase were purchased from Pharmacia Biotech. The relevant part of CBD, including the T7 promoter of pET-CBD180, was amplified by PCR using 25 pmol each of each of the primers GCGT CCGG CGTA GAGG ATCG (SEQ ID NO:11) and CCGG GATC CAAT GTTG CAGA AGT AG (SEQ ID NO:2), 2 U of Taq DNA polymerase, corresponding reaction buffer (10x PCR reaction buffer: 500 mM KCl, 15 mM $MgCl_2$, 100 mM Tris-HCl, pH 9), 0.2 mM dNTPs (dATP, dGTP, dTTP) and dCTP. Pharmacia Biotech) and 20 ng of heat-denatured pET-CBD180. PCR was performed in MJ-Research PTC-100 Thermo-cycler in 50 μl reaction volume and 30 cycles of 94° C., 30 sec.; 55° C., 30 sec. and 72° C., 30 sec. A BamHI restriction site (GGATCC) was incorporated at the 3'-end of the cbd gene to allow it to be cloned into pET21a(+). The BglII (AGATCT) or XbaI (TCTAGA) sites already present on pET-CBD 180 were used to cut the 5'-end of the PCR fragment. One μg of PCR product was digested in a 100 μl reaction containing 1.5× OPA (Pharmacia Biotech assay buffer One-Phor-All is supplied at 10× concentration: 100 mM Tris-acetate, pH 7.5; 100 mM magnesium acetate and 500 mM potassium acetate) and 10 U of BamHI and 10 U of HindIII. Plasmid pET21a(+) was digested in the same way, in 2×50 μl reactions each containing 0.25 μg of plasmid DNA, 1.5×OPA and 2 U of BamHI and HindIII each. Reactions were stopped by phenol/$CHCl_3$ extraction and ethanol precipitation. The resultant DNA pellets of digested pET21a(+) and relevant cbd and cbd96 inserts were dissolved in 8 μl of water and mixed, then 2 μl of 10 mM ATP, 2 μl of 10× OPA and 2 U of T4 DNA ligase were added and reactions were incubated at 10° C. for 1 hour. Then is 2 μl of each ligation mixture were used to electroporate 40 μl of *E. coli* XL1 Blue (Promega Corporation) using a sterile Gene Pulser cuvette (0.2 cm electrode gap) and Gene Pulser electroporator apparatus (Bio-Rad Laboratories) set to 2.5 kV, 200 ohms and 250° F. After an electroporation pulse, 1 ml of TB media (Maniatis, et al., *Molecular Cloning: A Laboratory Manual*, 2$^{nd}$ Ed., (Cold Spring Harbor Laboratory Press 1989) was added to the cell suspension and bacteria were incubated for 1 hour at 37° C. with rigorous shaking. Then 10, 50 and 100 μl of cell suspension were plated on MacKonkey agar (BBL, Becton Dickinson and Company, USA) plates with 100 μg/ml of Ampicillin and incubated overnight at 37° C. The next day, several colonies were transferred to 2 ml of TB and cultivated at 37° C. with vigorous shaking overnight. Then plasmid DNA was isolated and analyzed, including DNA sequencing by methods known to those skilled in the art. Positive clones contained plasmids pET21CBD-B or pET21CBD-X, respectively (FIG. 10). Plasmid pET21CBD-X contains lacO, which improves the regulation of the T7 expression system. Both plasmids contain a stop codon downstream of BamHI to allow expression of CBD180 protein. A T7 expression system was prepared in *E. coli* MC4100F (Strain MC4100F was prepared by mating *E. coli* XL1Blue and *E. coli* MC4100; ATCC Number 35695) based on pET variants and pGP1-2, which carries the T7 RNA polymerase gene under a λR promoter controlled by cI857 thermo-sensitive repressor (Tabor and Richardson, *Biochemistry* 82: 1074, 1985). CBD180 protein was expressed at high levels in both systems. Plasmid pET21CBD-X was used for subsequent work.

Plasmid pET21CBD96 (FIG. 5) was prepared using the same PCR conditions and cloning procedures. In this experiment the carrier protein CBD180 was truncated to about 96 amino acids. Therefore a pair of PCR primers GCGT CCGG CGTA GAGG ATCG (SEQ ID NO:3) and ATAT GGAT CCAG ATAT GTAT CATA GGTT GATG TTGG GC (SEQ ID NO:4) was used to prepare the relevant DNA fragment encoding cbd96 (FIG. 5), which was then cloned into pET21a(+). Then again a T7 expression system was prepared in *E. coli* MC4100F based on plasmids pET21CBD96 and pGP1-2 and protein CBD96 was expressed at high levels. pET21CBD96 was used for most of the subsequent work.

EXAMPLE 2

Construction and Expression of CBD—MBI-11FUSIONS

Sequences encoding all cationic peptides were designed from modified indolicidin, a natural anti-microbial peptide. Plasmids pET21CBD-X and pET21CBD96 (0.25 µg each) were digested with 2 U of BamHI and 2 U of HindIII in 1.5×OPA in 50 reactions at 37° C. for 1 hour. In the same way, a fragment encoding MBI-11 was digested (Example 4) using about 1 µg of DNA and 25U of BamHI and HindIII each in a 100 µl reaction. Both reactions were stopped by phenol/CHCl$_3$ (Sigma-Aldrich Canada Ltd.) extraction and ethanol precipitation. The resultant DNAs of each vector and MBI-11 insert were dissolved in 8 µl of water and mixed, then 2 µl of 10 mM ATP, 2 µl of 10× OPA and 2 U of T4 DNA ligase were added and ligation reactions were incubated at 10° C. for 1 hour. Then 2 µl of each ligation mixture was used to electroporate 40 µl of *E. coli* XL1 Blue using sterile Gene Pulser cuvettes (0.2 cm electrode gap) and Gene Pulser electroporator apparatus set to 2.5 kV, 200 ohms and 250µ F. After an electroporation pulse, 1 ml of TB media was added to the cell suspension and bacteria were incubated for 1 hour at 37° C. with rigorous shaking. Then 10, 50 and 100 µl of cell suspension were plated on MacKonkey agar plates with 100 P g/ml of Ampicillin (Sigma-Aldrich Canada Ltd.) and incubated overnight at 37° C. The next day, several colonies were transferred to 2 ml of TB and cultivated at 37° C. with vigorous shaking overnight. Then plasmid DNA was isolated and analyzed, including DNA sequencing by methods known to those skilled in the art. Positive clones contained MBI-11 fused to CBD180 or CBD96. Expression strains of *E. coli* MC4100F harboring plasmids pGP1-2 and pET21CBD-11 or pET21CBD96-11 respectively were prepared by electroporation. Final strains were incubated overnight in 2 ml TB at 30C with rigorous shaking and the next day 1 ml of cell suspension was diluted with the equal volume of fresh TB and cultivation temperature was increased to 42° C. for a minimum of 2 hours. Samples of preinduced and induced cells were analyzed by SDS-PAGE. The level of expression of the fusion protein caring MBI-11 or 2x MBI-11 gene was high and equal to expression of CBD 180 or CBD96 alone.

EXAMPLE 3

Expression of CBD Fused Polycationic Peptide Tandem Domains

This experiment was designed to test how many peptide genes in tandem can be fused to a carrier protein and expressed. It was necessary to create two DNA fragments encoding MBI-11, one for polymerization by DNA cloning and another one as the last gene in the tandem. Therefore, the original DNA fragment encoding MBI-11 peptide with COOH end was modified in order to create the last gene in tandem (Example 4) and a new gene was designed for a specific cloning procedure, which allowed construction of multiple tandem peptide genes fused to CBD180 or CBD96 carrier proteins genes (Example 4). The cloning procedure resulted in addition of an extra isoleucine to the MBI-11 tandem sequences. Therefore in order to produce identical peptide molecules, an isoleucine codon was also added to the last gene sequence. CNBr will be used to cleave the peptide from fusion proteins, which means that peptide molecules would have a homoserine lactone on the end. Therefore the last peptide gene was also modified to have a methionine followed by two tyrosines at the end for CNBr cleavage in order to produce equivalent peptide products.

CBD180 and CBD96 fused peptide polygenes of up to 10 units in tandem were prepared. However good expression was only achieved with a fusion containing two and three MBI-11 domains and practically stopped when the number of peptide genes exceeded four. DNA synthesis and construction of plasmids containing MBI-11 polymers is described in Example 4.

EXAMPLE 4

Synthesis and Modification of DNA Fragments Encoding Cationic Peptides

The desired sequences were conventionally synthesized by the phosphoramidite method of oligonucleotide synthesis using the Applied Biosystems Model 391 DNA Synthesizer with connected chemicals and protocols. Desired oligonucleotides were used as templates in the PCR reaction to produce double stranded DNA suitable for DNA cloning.

A. SYNTHESIS OF THE MBI-11 DNA DOMAIN

An oligonucleotide TTTA ACGG GGAT CCGT CTCA TATG ATCC TGAA AAAA TGG (SEQ ID NO:5) CCGT GGTG GCCG TGGC GTCG TAAA TAAG CTTG ATAT CTTG GTAC CTGC G (SEQ ID NO:6) was synthesized and used as a template for PCR using primers TTTA ACGG GGAT CCG TCTC ATAT G (SEQ ID NO:7) and TAAG CTTG ATAT CTTG GTAC CTGC G (SEQ ID NO:8). The PCR was performed in MJ-Research PTC-100 Thermocycler in a 50 µl reaction volume with 30 cycles of 94° C., 30 sec.; 50° C., 30 sec. and 72° C., 30 sec., 2 U of Taq DNA polymerase, corresponding reaction buffer (10x PCR reaction buffer: 500 mM KCl, 15 mM MgCl$_2$, 100 mM Tris-HCl pH 9), 0.2 mM dNTPs (dATP, dGTP, dTTP and dCTP), 25 pmol of each primer and 50 pmol of template oligonucleotide resulting in an 88 bp dsDNA MBI-11 fragment. DNA was used for the cloning procedure described in Example 2.

B. Modification of MBI-11 Domain as the Last Domain In Tandem

PCR was used to modify the original DNA fragment encoding MBI-11 for use as the last gene in the tandem polypeptide gene. The original oligonucleotide (A) was used as a template. The sense primer TTTA ACGG GGAT CCGT CTCA TATG (SEQ ID NO:9) was identical to that used in the synthesis PCR reaction, but a new antisense primer CGCG AAGC TTAA TAAT ACAT AATT TTAC GACG CCAC GGCC ACCA CGGC (SEQ ID NO:10) was designed to modify the end of the MBI-11 gene (for explanation, see Example 3). The PCR was performed in MJ-Research PTC-100 Thermo-cycler in a 50 µl reaction volume with 30 cycles of 94° C. 30 sec., 51° C., 30 sec. and 72° C., 30 sec., 2 U of Taq DNA polymerase, corresponding reaction buffer (10x PCR reaction buffer: 500 mM KCl, 15 mM MgCl$_2$, 100 mM Tris-HCl pH 9), 0.2 mM dNTPs (dATP, dGTP, dTTP and dCTP), 25 pmol of each primer and 50 pmol of the template oligonucleotide. The PCR product was then cloned as a BamHI-HindIII fragment into pBCKS(+) (Stratagene, USA) resulting in plasmid pBCKS-11. Modification was verified by DNA sequencing.

C. Synthesis of MBI-11 Fragment Designated for the Polymerization Cloning Procedure An oligonucleotide CGCC AGGG TTTT CCCA GTCA CGAC GGAT CCGT CTCA TATG ATCC TGAA AAAA TGGC CGTG GTGG CCGT GGCG TCGT AAAA TTAA TTGA ATTC GTCA TAGC TGTT TCCT GTGT GA (SEQ ID NO:11) was synthesized and used as a template for PCR using primers CGCC AGGG TTTT CCCA GTCA CGAC (SEQ ID NO:12) and TCAC ACAG GAAA CAGC TATG AC (SEQ ID NO:13). The PCR was performed in MJ-Research PTC-100 Thermo-cycler in a 50 µl reaction volume with 30 cycles of 94° C., 30 sec., 51° C., 30 sec. and 72° C., 30 sec., 2U of Taq DNA polymerase, corresponding reaction buffer (10x PCR reaction buffer: 500 mM KCl, 15 mM MgCl$_2$, 100 mM Tris-HCl pH 9), 0.2 mM dNTPs (dATP, dGTP, dTTP and dCTP), 25 pmol of each primer and 50 pmol of template oligonucleotide resulting in 114 bp dsDNA MBI-11-BE fragment. This fragment was cloned as a BamHI-EcoRI insert into vector pBCKS(+) resulting in pBCKS-11BE.

D. Polymerization Cloning Procedure

The copy of MBI-11 designed for the polymerization cloning procedure was cloned into pET21 CBD96-11 resulting in pET21 CBD96-2x11. pBCKS-11BE was digested with 2 U of BamHI and VspI in 2x OPA in 50 µl reactions at 37° C. for 1 hour and pET21CBD96-11 was digested with 2 U of BamHI and NdeI in 2x OPA in a 50 µl reaction at 37° C. for 1 hour. Reactions were stopped by phenol/CHCl$_3$ extraction and ethanol precipitation. The resulting DNA pellets were dissolved in 8 µl of water each and mixed, then 2 µl of 10 mM ATP, 2 µl of 10x OPA and 2 U of T4 DNA ligase were added and reactions were incubated at 10° C. for 1 hour. Then 2 µl of the ligation mixture was used to electroporate 40 µl of E. coli XL1 Blue using Gene Pulser cuvettes (0.2 cm electrode gap) and Gene Pulser (Bio-Rad Laboratories) set to 2.5 kV, 200 ohms and 250 µF. After an electroporation pulse, 1 ml of TB media was added to the cell suspension and bacteria were incubated 1 hour at 37° C. with rigorous shaking. Then 10, 50 and 100 µl of cell suspension were plated on MacKonkey agar plates with 100 µg/ml of Ampicillin and incubated overnight at 37° C. The next day, several colonies were transferred to 2 ml of TB and cultivated at 37° C. with vigorous shaking overnight. Then plasmid DNA was isolated and analyzed, including DNA sequencing by methods known to those skilled in the art. Positive clones contained pET21CBD96-2x11. The ligation of compatible VspI and NdeI cohesive ends resulted to elimination of both restriction sites. At the same time, the insertion of the mbi-11 be cassette introduced a new NdeI site, which allowed repetition of the cloning procedure and insertion of another mbi-11 be. This procedure could be repeated theoretically without limitation. In this particular case the serial cloning was repeated nine times and constructs up to pET21 CBD96-10x11 were prepared.

EXAMPLE 5

Synthesis of DNA Cassettes for Construction of Fused and Unfused Multi-Domain Expression Systems A. Synthesis of MBI 2x11B7-Last Cassette An oligonucleotide CGCC AGGG TTTT CCCA GTCA CGAC GGAT CCGT CTCA TATG ATTC TGCG TTGG CCGT GGTG GGCG TGGC GTCG CAAA ATGA TTCT GCGT TGGC CGTG GTGG CCGT GGCG TCGC AAAA TGGC GGCC TAAG CTTC GATC CTCT ACGC GGA CGC (SEQ ID NO:14) was synthesized and used as a template for PCR using primers CGCC AGGG TTTT CCCA GTCA CGAC (SEQ ID NO:15) and GCGT CCGG CGTA GAGG ATCG (SEQ ID NO:16). The PCR was performed in MJ-Research PTC-100 Thermo-cycler in a 50 µl reaction volume with 30 cycles of 94° C., 30 sec.; 55° C., 30 sec. and 72° C., 30 sec. 2 U of Taq DNA polymerase, corresponding reaction buffer (10x PCR reaction buffer: 500 mM KCl, 15 mM MgCl$_2$, 100 mM Tris-HCl pH 9), 0.2 mM dNTPs (dATP, dGTP, dTTP and dCTP), 25 pmol of each primer and 50 pmol of template oligonucleotide resulting in 151 bp dsDNA MBI-11 fragment. The PCR product was purified by phenol/CHCl$_3$ extraction and ethanol precipitation. The resulting DNA was dissolved in 100 µl 1x OPA, 20 U of BamHI and 20 U of HindIII and the reaction was incubated at 37° C. for 2 hours. The vector pBCKS(+) (0.25 µg) was digested in the same way. Both reactions were stopped by phenol/CHCl$_3$ extraction and ethanol precipitation. The resultant DNAs of each vector and MBI-11 insert were dissolved in 8 µl of water and mixed, then 2 µl of 10 mM ATP, 2 µl of 10x OPA and 2 U of T4 DNA ligase were added and ligation reactions were incubated at 10° C. for 1 hour. Then 2 µl of each ligation mixture was used to electroporate 40 µl of E. coli XL1 Blue using a sterile Gene Pulser cuvette (0.2 cm electrode gap) and Gene Pulser electroporator apparatus set to 2.5 kV, 200 ohms and 250 µF. After an electroporation pulse, 1 ml of TB media was added to the cell suspension and bacteria were incubated 1 hour at 37° C. with rigorous shaking. Then 10, 50 and 100 µl of cell suspension were plated on MacKonkey agar plates with 100 µg/ml of Ampicillin and incubated overnight at 37° C. The next day, several colonies were transferred to 2 ml of TB and cultivated at 37° C. with vigorous shaking overnight. Then plasmid DNA was isolated and analyzed, including DNA sequencing by methods known to those skilled in the art. The resulting plasmid was pBCKS-2x11B7. The insert was later recloned into pBCKS-V resulting in pBCKS-V-2x11B7.

B. Synthesis of MBI-11B 7-Poly Cassette

An oligonucleotide CGCC AGGG TTTT CCCA GTCA CGAC GGAT CCGT CTCA TATG ATTC TGCG TTGG CCGT GGTG GCCG TGGC GTCG CAAA ATGC ATAA GCTT CGAT CCTC TACG CCGG ACGC (SEQ ID NO:17) was synthesized and used as a template for PCR using primers CGCC AGGG TTTT CCCA GTCA CGAC (SEQ ID NO:18) and GCGT CCGG CGTA GAGG ATCG (SEQ ID NO:19). The PCR was performed in MJ-Research PTC-100 Thermo-cycler in a 50 µl reaction volume with 30 cycles of 94° C., 30 sec.; 55° C., 30 sec. and 72° C., 30 sec., 2 U of Taq DNA polymerase, corresponding reaction buffer (10x PCR reaction buffer: 500 mM KCl, 15 mM MgCl$_2$, 100 mM Tris-HCl pH 9), 0.2 mM dNTPs (dATP, dGTP, dTTP and dCTP), 25 pmol of each primer and 50 pmol of template oligonucleotide resulting in a 112 bp dsDNA MBI-11 fragment. The resulting DNA fragment was cloned into pTZ18R (Pharmacia Biotech) as a BamHI-HindIII fragment as described in paragraph (A) resulting in plasmid pTZ18R-11B7poly.

C. Synthesis of Avionic Spacer Cassette

An oligonucleotide CGCC AGGG TTTT CCCA GTCA CGAC GGAT CCGT CTAT GCAT GAAG CGGA ACCG GAAG CGGA ACCG ATTA ATTA AGCT TCGA TCCT CTAC GCCG GACG C (SEQ ID NO:20) was synthesized and used as a template for PCR using primers CGCC AGGG TTTT CCCA GTCA CGAC (SEQ ID NO:21) and GCGT CCGG CGTA GAGG ATCG (SEQ ID NO:22). The PCR was performed in MJ-Research PTC-100 Thermo-cycler in a 50 µl reaction volume with 30 cycles of 94° C., 30 sec.; 55° C., 30 sec. and 72° C., 30 sec., 2 U of Taq DNA polymerase, corresponding reaction buffer (10x PCR reaction buffer: 500 mM KCl, 15 mM MgCl$_2$, 100 mM Tris-HCl pH 9), 0.2 mM dNTPs (dATP, dGTP, dTTP and dCTP), 25 pmol of each primer and 50 pmol of template oligonucleotide resulting in a 97 bp dsDNA MBI-11 fragment. The resulting DNA fragment was cloned into pBCKS-V as a BamHI-HindIII fragment as described in paragraph (A), resulting in plasmid pBCKS-V-S.

D. Synthesis of MBI-11B7-First Cassette

An oligonucleotide CGCC AGGG TTTT CCCA GTCA CGAC GGAT CCGT CTCA TATG ACTA TGAT TCTG CGTT GGCC GTGG TGGC CGTG GCGT CGCA AAAT GCAT AAGC TTCG ATCC TCTA CGCC GGAC GC (SEQ ID NO:23) was synthesized and used as a template for PCR using primers CGCC AGGG TT TT CCCA GTCA CGAC (SEQ ID NO:24) and GCGT CCGG CGTA GAGG ATCG (SEQ ID NO:25). The PCR was performed in MJ-Research PTC-100 Thermo-cycler in a 50 µl reaction volume with 30 cycles of 94° C., 30 sec.; 55° C., 30 sec. and 72° C., 30 sec, 2 U of Taq DNA polymerase, corresponding reaction buffer (10x PCR reaction buffer: 500 mM KCl, 15 mM MgCl$_2$, 100 mM Tris-HCl, pH 9), 0.2 mM dNTPs (dATP, dGTP, dTTP and dCTP), 25 pmol of each primer and 50 pmol of template oligonucleotide resulting in a 114 bp dsDNA MBI-11 fragment. The resulting DNA fragment was cloned into pBCKS-V-S as a BamHI-NsiI fragment basically as described in paragraph (A), resulting in plasmid pBCKS-V-11 B7S-F. The only exception was that 2x OPA was used in the restriction enzyme digest reaction.

E. Construction of Plasmid pBCKS-V

Plasmid pBCKS-V was prepared from pBCKS(+). The goal was to eliminate all VspI restriction sites from the original plasmid and use the resulting plasmid for cloning of some of DNA cassettes.

About 1 µg of pBCKS(+) was digested with VspI (Promega) in 50 µl reaction using 1x OPA. The reaction was stopped by phenol/CHCl$_3$ extraction and ethanol precipitation. The resulting DNA was dissolved in 50 µl of 1x OPA, 0.2 mM dNTPs and 1 U of Klenow polymerase. The reaction was incubated at 30° C., for 30 min. and then stopped by phenol/CHCl$_3$ extraction and ethanol precipitation. DNA was then dissolved in 50 µl of 1x OPA, 0.5 mM ATP and 15U of T4 DNA ligase and the reaction was incubated at 10° C. and after 4 hours stopped by incubation at 65° C. for 30 min. Then 20 U of VspI was added to the reaction to digest any remaining pBCKS(+) molecules and after 3 hours incubation at 37° C., 2 µl of the ligation mixture were used to electroporate 40 µl of E. coli MC4100F using a sterile Gene Pulser cuvette (0.2 cm electrode gap) and Gene Pulser electroporator apparatus set to 2.5 kV, 200 ohms and 250 µF.

After an electroporation pulse, 1 ml of TB media was added to the cell suspension and bacteria were incubated 1 hour at 37° C. with rigorous shaking. Then 10, 50 and 100 µl of cell suspension were plated on MacKonkey agar plates with 25 µg/ml of Chloramphenicol and incubated overnight at 37° C. The next day, several colonies were transferred to 2 ml of TB and cultivated at 37° C. with vigorous shaking overnight. Then plasmid DNA was isolated and analyzed by VspI restriction analysis. All plasmids lacked VspI sites and their size corresponded with the calculated size of pBCKS-V.

EXAMPLE 6

Construction of Fused Multi-Domain Expression Systems

A. Construction of pET21CBD96-2x11B7

Plasmids pET21CBD96 (0.25 µg) and pBCKS-2x11B7 (2.5 µg) were digested with BamHI and HindIII in 1.5x OPA in a 50 µl reaction at 37° C. for 1 hour using 2 U of each restriction enzyme and 20 U of each enzyme respectively. Both reactions were stopped by phenol/CHCl$_3$ extraction and ethanol precipitation. The resulting DNAs were dissolved in 8 µl of water and mixed, then 2 µl of 10 mM ATP, 2 µl of 10x OPA and 2 U of T4 DNA ligase were added and the ligation reaction was incubated at 10° C. for 1 hour. Then 2 µl of the ligation mixture was used to electroporate 40 µl of E. coli XL1 Blue using a sterile Gene Pulser cuvette (0.2 cm electrode gap) and Gene Pulser electroporator apparatus set to 2.5 kV, 200 ohms and 250 µF. After an electroporation pulse, 1 ml of TB media was added to the cell suspension and bacteria were incubated 1 hour at 37° C. with rigorous shaking. Then 10, 50 and 100 µl of cell suspension were plated on MacKonkey agar plates with 100 µg/ml of Ampicillin and incubated overnight at 37° C. The next day several colonies were transferred to 2 ml of TB and cultivated at 37° C. with vigorous shaking overnight. Then plasmid DNA was isolated and analyzed, including DNA sequencing by methods known to those skilled in the art. Positive clones pET21CBD96-2x11B7 contained tandem MBI-11 genes fused to cbd96.

B. The Use of Serial Cloning Procedure For Construction Of Fused Multi-Domain Plasmids The idea of the serial cloning procedure is that the insertion of the BamHI-MBI-11B7-P-VspI cassette into the BamHI-NdeI sites of pET21CBD96-2x11B7 and subsequent multi-domain clones always eliminates the original NdeI site by NdeI/VspI ligation and a new NdeI site is introduced with each insertion, which together with BamHI is used for the next cycle of cloning.

Plasmid pET21CBD96-2x11B7 (0.25 µg) was digested with 2 U of BamHI and NdeI in 2x OPA in 50 µl reaction at 37° C. for 1 hour. Plasmid pBCKS-V-11B7S (2.5 µg) was digested in a 100 µl reaction with 20 U of BamHI and VspI in 2x OPA at 37° C. for 1 hour. Both reactions were stopped by phenol/CHCl$_3$ extraction and ethanol precipitation. The resulting DNAs were dissolved in 8 µl of water and mixed, then 2 µl of 10 mM ATP, 2 µl of 10x OPA and 2 U of T4 DNA ligase were added and the ligation reaction was incubated at 10° C. for 1 hour. Then 2 µl of the ligation mixture were used to electroporate 40 µl of E. coli XL1 Blue using a sterile Gene Pulser cuvette (0.2 cm electrode gap) and Gene Pulser electroporator apparatus set to 2.5 kV, 200 ohms and 250 µF. After an electroporation pulse, 1 ml of TB media was added to the cell suspension and bacteria were incubated 1 hour at 37° C. with rigorous shaking. Then 10, 50 and 100 µl of cell suspension were plated on MacKonkey agar plates with 100 p g/ml of Ampicillin and incubated overnight at 37° C. The next day, several colonies were transferred to 2 ml of TB and cultivated at 37° C. with vigorous shaking overnight. Then plasmid DNA was isolated and analyzed, including DNA sequencing by methods known to those skilled in the art. Positive clones pET21CBD96-1s-3x11B7 contained three MBI-11 units with one spacer fused to cbd96. This was the first cycle of the serial cloning. In the next cycle pET21CBD96-1s-3x11B7 and pBCKS-V-11B7S were used and cloning was repeated resulting in pET21CBD96-2s-4x11B7. Then pET21CBD96-2s-4x11B7 and pBCKS-V-11B7S were used for the next cloning resulting in pET21CBD96-3s-5x11B7 and soon.

In order to accelerate the serial cloning procedure plasmid pBCKS-V-5x11B7S was prepared and each cloning cycle would add five 11B7S domains. First the 11B7S insert of pBCKS-V-11B7S was recloned into pTZ18R, resulting in pTZ18R-11B7S. Then this plasmid was used as the donor of the 11B7S domain for the serial cloning into pBCKS-V-11B7S using the BamHI-NdeI/VspI strategy. The serial cloning procedure was repeated four times resulting in pBCKS-V-5S-5x11B7S. The 5S-5x11B7 cassette was then used for construction of CBD96-fused systems containing more than fifteen. 11B7 domains and also CBD96-fused multidomain systems with equal numbers of 11B7 and anionic spacer domains (Table 2).

The cassette 5S-5x11B7 of pBCKS-V-5S-5x11B7 with anionic spacer domain at the end was cloned into pET21CBD96 using BamHI and KpnI restriction enzymes resulting in pET21CBD96-5S-5x11B7. In the second cloning cycle the same cassette was ligated as BamHI-VspI fragment of pBCKS-V-5x11B7S into BamHI-NdeI sites of pET21CBD96-5S-5x11B7 resulting in pET21CBD96-10S-10x11B7. This can be repeated several times to receive constructs with 15, 20, 25 etc. 11B7 domains and equal numbers of anionic spacer domains. Conditions for restriction enzymes, ligation, electroporation and analysis of recombinant plasmids are described above.

EXAMPLE 7

Construction Of Unfused Multi-Domain Expression Systems

In *E. coli*, the first amino acid in all proteins is f-methionine. However, this amino acid is not cleaved by CNBr, which means that one peptide domain released from a multi-domain protein would start with f-methionine. The solution was to create a modified MBI-11 cassette encoding f-methionine and methionine in tandem at the beginning of the peptide, so the second one would be cleaved by CNBr. The result was the synthesis of the special first domain in multi-domain genes, cassette MBI-11B7F, encoding MTM amino acids at the beginning. This domain was fused to the spacer domain in pBCKS-V-S resulting in plasmid pBCKS-V-11B7S-F.

Plasmid pBCKS-V-11B7S-F and the relevant pET21CBD96-multi-domain-11B7 plasmids were used for construction of unfused multi-domain MBI-11B7 genes. Multi-domain genes were liberated from cbd96 by NdeI-XhoI digestion and cloned into the VspI-XhoI sites of pBCKS-V-11B7S-F downstream of the 11B7S insert. This created a line of unfused multi-domain 11B7 genes in plasmid pBCKS-V. These genes were then recloned as NdeI-XhoI fragments into pET21a(+) resulting in a series of pET plasmids capable of expression of multi-domain proteins using the T7 promoter system.

Plasmid pBCKS-V-11B7S-F (0.25 µg) was digested with 2 U of NdeI and XhoI in 2x OPA in several 50 µl reactions at 37° C. for 1 hour. Relevant plasmids pET21CBD96-multidomain-11B7 (2.5 µg) were digested in 100 µl reactions with 20 U of NdeI and XhoI in 2x OPA at 37° C. for 1 hour. All reactions were stopped by phenol/CHCl$_3$ extraction and ethanol precipitation. The resultant vector and insert DNAs were dissolved in 8 µl of water and mixed, then 2 µl of 10 mM ATP, 2 µl of 10x OPA and 2 U of T4 DNA ligase were added and ligation reactions were incubated at 10° C. for 1 hour. Then 2 µL of each ligation mixture was used to electroporate 40 µl of *E. coli* XL1 Blue using a sterile Gene Pulser cuvette (0.2 cm electrode gap) and Gene Pulser electroporator apparatus set to 2.5 kV, 200 ohms and 250 µF. After an electroporation pulse, 1 ml of TB media was added to the cell suspension and bacteria were incubated 1 hour at 37° C. with rigorous shaking. Then 10, 50 and 100 µl of cell suspension were plated on MacKonkey agar plates with 100 µg/ml of Ampicillin and incubated overnight at 37° C. The next day several colonies were transferred to 2 ml of TB and cultivated at 37° C. with rigorous shaking overnight. Then plasmid DNA was isolated and analyzed, including DNA sequencing by methods known to those skilled in the art. Positive clones contained pET21-multidomain-11B7 plasmids containing 5, 6, 7, 8, 9, 10, 11, 12, 13, 14, 15, 16 and 21 MBI-11B7 domains.

In the same way, constructs were prepared containing equal numbers of 11B7 and anionic spacer domains. By way of illustration: pET21 CBD96-5S-5x11B7 was digested with BamHI and XhoI (or HindIII) and fragment 5S-x11B7 was ligated into BamHI-XhoI (or HindIII) of pBCKS-V-11B7S-F resulting in pBCKS-V-6S-6x11B7. The BamHI-6S-6x11B7-XhoI cassette of pBCKS-V-6S-6x11B7 was then recloned into BamHI-XhoI of pET21a(+) resulting in pET21-6S-6x11B7. All cloning procedures and clone analysis are described above.

EXAMPLE 8

Construction of Fused Multidomain Mb126 Expression Systems

In our previous work we solved all major problems connected to the construction of multidomain cationic peptide expression systems. This example demonstrates we were able to simplify the process, especially the need for synthesis of multiple specific DNA cassettes; only one mbi26 cassette was prepared and used at the first and last position as well as for the serial cloning procedure. Plasmids pET21CBD96-1s-26 and pET21CBD96-2s-2x26 were prepared. We tested expression of a combination of mbi26 and mbi11 B7 domains. We performed two cloning cycles, inserting mbi26S cassettes into pET21 CBD96-1 S-3x11 B7, resulting in pET21 CBD96-26S-3x11B7 and pET21CBD96-2x26S-3x11B7. Both constructs expressed the combined mbi26-11B7 multidomain proteins at good levels.

A. Synthesis Of Universal MB126 Domain

An oligonucleotide CGCC AGGG TTTT CCCA GTCA CGAC GGAT CCGT CTCA TATG ACCA TGAA ATGG AAAT CTTT CATC AAAA AACT GACC TCTG CTGC TAAA AAAG TTGT TACC ACCG CTAA ACCG CTGA TCTC TATG CATG CTTA AGCT TCGA TCCT CTAC GCCG GACG C (SEQ ID NO: 26) was synthesized and used as a template for PCR using primers CGCC AGGG TTTT CCCA GTCA CGAC (SEQ ID NO:18) and GCGT CCGG CGTA GAGG ATCG (SEQ ID NO:19). PCR was performed in an MJ-Research PTC-100 Thermo-cycler in a 50 µl reaction volume with 30 cycles of 94° C., 30 sec.; 55° C., 30 sec. and 72° C., 30 sec., 2 U of Taq DNA polymerase, corresponding reaction buffer (10x PCR reaction buffer: 500 mM KCl, 15 mM MgCl$_2$, 100 mM Tris-HCl pH 9), 0.2 mM dNTPs (dATP, dGTP, dTTP and dCTP), 25 pmol of each primer and 50 pmol of template oligonucleotide resulting in a 112 bp dsDNA MBI26 fragment. The resulting DNA fragment was cloned into pTZ18R as a BamHI-HindIII fragment as described in Example 2, paragraph (A) resulting in plasmid pTZ18R-26GT. After verification of DNA sequence, the BamHI-HindIII mbi26 fragment was recloned into pBCKS(+) resulting in pBCKS-26GT.

B. Construction of MBI126 Fused Multidomain System

The first step in construction was a direct fusion of the mbi26 cassette to cbd96 in pET21CBD96. Plasmids pET21CBD96 (0.25 µg) and pBCKS-26GT (2.5 µg) were digested with BamHI and HindIII in 1.5x OPA (50 µl reaction volume) at 37° C. for 1 hour using 2 U of each restriction enzyme and 20 U of each enzyme respectively. Both reactions were stopped by phenol/CHCl$_3$ extraction and ethanol precipitation. Each resulting DNA was dissolved in 8 µl of water; the two were mixed together with 2 µl of 10 mM ATP, 2 µl of 10x OPA and 2 U of T4 DNA ligase and the ligation reaction was incubated at 10° C. for 1 hour. 2 µl of the ligation mixture was used to electroporate 40 µl of E. coli XL1 Blue using a sterile Gene Pulser cuvette (0.2 cm electrode gap) and Gene Pulser electroporator apparatus set to 2.5 kV, 200 ohms and 250 µF. After an electroporation pulse, 1 ml of TB media was added to the cell suspension and bacteria were incubated 1 hour at 37° C. with rigorous shaking. Then 10, 50 and 100 µl of cell suspension were plated on MacKonkey agar plates with 100 µg/ml of Ampicillin and incubated overnight at 37° C. The next day several colonies were transferred to 2 ml of TB and cultivated at 37° C. with rigorous shaking overnight. Then plasmid DNA was isolated and analyzed, including DNA sequencing by methods known to those skilled in the art; Positive clones pET21CBD96-26 contained the MBI-26 gene fused to cbd96.

The second step was preparation of a cassette for the serial cloning procedure. The mbi26 fragment of pTZ18R-026GT was cloned into pBCKS-V-S as a BamHI-NsiI fragment basically as described in Example 5 (A), resulting in plasmid pBCKS-V-26S with an mbi26 domain fused to the anionic spacer-encoding sequence. The only exception was that 2x OPA was used in the restriction enzyme digest reaction. The insert was then cloned into pTZ18R resulting in pTZ18R-26S. This allowed the cloning of the BamHI-26S-VspI insert into the BamHI-NdeI sites of pBCKS-V-26S, resulting in pBCKS-V-2S-2x26.

The third step was the actual serial cloning procedure (for details see Example 6B). Briefly, pBCKS-V-26S was digested with BamHI and VspI resulting in fragment BamHI-26S-VspI, which was ligated into plasmid pET21CBD96-26GT digested with BamHI and NdeI. Positive clones pET21CBD96-1s-2x26contained two MBI-26 units with one spacer fused to cbd96. This was the first cycle of the serial cloning. In the next cycle pET21CBD96-1s-2x26 and pBCKS-V-26S could be used to prepare pET21CBD96-2s-3x26 and so on.

C. Construction and Expression Of Combined MBI26-MBI11B7 Multidomain Genes

Plasmid pET21CBD96-1S-3x11B7 was used as a vector for serial cloning of the mbi26S domain of pBCKS-V-26S. Briefly, pBCKS-V-26S was digested with BamHI and VspI restriction endonucleases resulting in fragment BamHI-26S-VspI, which was ligated into plasmid pET21CBD96-1S-3x11B7 digested with BamHI and NdeI. Positive clones pET21CBD96-2S-26-3x11B7 contained an MBI-26 unit with one spacer fused to three 11B7 units with one spacer. This was the first cycle of the serial cloning. In the next cycle pET21CBD96-2S-26-3x11B7 and pBCKS-V-26S were used to prepare pET21CBD96-3S-2x26-3x11B7.

T7 expression systems were prepared in E. coli MC4100F based on plasmids pET21CBD96-2S-26-3x11B7 or pET21CBD96-3S-2x26-3x11B7 and pGP1-2. Proteins CBD96-2S-26-3x11B7 and CBD96-3S-2x26-3x11B7 were expressed at good levels after temperature induction.

EXAMPLE 9

Production in Shake Flask Fermentation of Multi-Domain Cationic Peptide Fused to Truncated CBD or Unfused Systems Each of the different pET21CBD96-(n-2)S-nx11B7, pET21CBD96-nS-nx11B7, pET21-(n-2)S-nx11B7 and pET21-nS-nx11B7F constructs (where n=number of copies, S represents the anionic spacer, and 11B7 or 11B7F represents the cationic MBI-11B7 peptide) were expressed in E. coli strain MC4100F.

All fermentations are done in TB broth, which is prepared as follows: 12 g of Trypticase Peptone (BBL), 24 g of yeast Extract (BBL) and 4 ml of glycerol (Fisher) is added to 900 ml of Milli-Q water. The material is allowed to dissolve and 100 ml of 0.17 M KH$_2$PO$_4$ (BDH), 0.72 M K$_2$HPO$_4$ (Fisher) is added. The broth is autoclaved at 121° C. for 20 minutes. The resulting pH is 7.4.

A one liter Erlenmeyer flask with 170 ml medium, containing 100 µg/ml ampicillin (Sigma-Aldrich Corp.) and 30 µg/ml kanamycin A (Sigma-Aldrich Corp.), was inoculated with the relevant 0.5 ml frozen stock and shaken at 300 rpm in a shaking incubator (model 4628, Lab Line Instrument Inc.), at 30° C. for 16 hr.

The culture was then transferred to a 2.0 L flask with 330 ml fresh TB medium (no antibiotics), preincubated at 30° C. After dilution, protein expression was induced by raising the culture temperature to 42° C. and shaking at 300 rpm for another 5 to 7 hours. The pH was kept between 6.7 and 7.1 using 30% ammonium hydroxide. Bacteria were fed at least twice during induction with 0.5 g glucose per flask. Cells were harvested by centrifugation (Sorvall® RC-5B) at 15,000 xg for 15 minutes and cell pellets were stored at −70° C. prior to cell lysis.

EXAMPLE 10

Crude Fractionation and Inclusion Bodies Isolation

The bacteria produce the multi-domain proteins as insoluble inclusion bodies. To release and isolate the inclusion bodies, the harvested cells were suspended in 200 ml buffer (50 mM Tris-HCl, 10 mM EDTA, pH 8.0) and lysed by sonication (Vibra-Cell™, Sonic and material Inc.) five times for 45 seconds, on ice, then centrifuged (Sorvall® RC-5B) at 21,875 xg for 15 min at 4° C. The pellet was homogenized (PolyScience, Niles, Ill. USA) in 160 ml of lysis buffer (20 mM Tris-HCl, 100 µg/ml lysozyme, pH 8.0) and incubated at room temperature for 45 min. Next Triton X-100 was added (1% v/v), and the mixture was homogenized thoroughly and centrifuged at 21,875 xg for 15 min at 4° C. The inclusion bodies pellet was resuspended in 200 ml of 0.1 M NaCl, homogenized, and precipitated by centrifugation as described above, then resuspended in 200 ml water and precipitated again by centrifugation. At this stage, the inclusion bodies contained greater than 70% fusion protein.

EXAMPLE 11

Releasing of Cationic Peptide By Chemical Cleavage

The isolated inclusion bodies were dissolved in 70% formic acid (100 mg wet weight IB per ml), then CNBr was added to a final concentration of 0.1 to 0.15 M. The cleavage reaction which allowed the release of cationic peptide from the fusion protein and spacer was performed under nitrogen and with stirring, in the dark, for 4 hr. Next the reaction mixture was diluted with 15 volumes of Milli-Q water and dried in a rotovap machine (Rotovapore, R-124VP, BUCHI Switzerland). The dried pellet was then dissolved in 10 ml of 7–8 M urea and insoluble materials were separated by centrifugation at 21,875 xg for 15 min.

At this stage, the soluble materials, at acidic pH (2–3.3) and low conductivity (1–5 mS), contain the homoserine lactone form of the cationic peptide. This material was further purified using a chromatography procedure.

EXAMPLE 12

Free Cationic Peptide Purification

The purification of the homoserine lactone form of MB-11B7 peptide was performed on a BioSys™ 2000 chromatography work station (Beckman Instruments, Inc.), using Fast Flow Q-Sepharose anion exchange resin (Pharmacia Biotech AB) packed in an XK column (1.6×11 cm). The column was equilibrated with 2 column volumes (CV) of 1 M NaOH at a flow rate of 9 ml/min, followed by a water wash. Conductivity, pH and absorbency at 280 nm were monitored. When the conductivity dropped below 5 mS, the dried cleavage materials, dissolved in 7–8 M urea, were loaded onto the column and washed with 4 M urea. The unbound pure cationic peptide flowed through the column and was monitored as the leading peak. When the absorbance dropped to baseline, the bound material (i.e., impurities) was washed off the column with 1 M NaOH and appeared as the second peak (FIG. 9).

The flow-through peak was collected and pooled and the pH was adjusted to 7.0–7.5 with 0.2 N HCl. The sample was analyzed for purity by reverse phase HPLC (FIG. 11), using a C8 column (4.6×10, Nova-Pak, Waters) and by acid-urea gel electrophoresis (West and Bonner, *Biochemistry* 19: 3238, 1980). The identity of the MBI-11B7 peptide was confirmed by mass spectrometry to show that the flow through peak represents the homoserine form of the MBI-11B7 peptide.

EXAMPLE 13

Urea Separation and Further Purification

The separation of the urea from the purified peptide utilized a high-throughput reverse phase chromatography technique by using the BioCAD™ (PerSeptive Biosystems Inc.) perfusion chromatography workstation and Poros®R-II 20column, 4.6×100 mm (PerSeptive Biosystems Inc.). About 10 mg of the peptide were applied on the column at 5 ml/min, followed by equilibration of the column with 0.1% TFA. The peptide was eluted from the column by a gradient of increasing acetonitrile from 0 to 50% for 10 minutes at a flow rate of 5 mL/min. The peak of the further purified and urea free peptide was collected and lyophilized.

EXAMPLE 14

Bactericidal Activity of MBI-11B7CN Peptide and its Homoserine/Homoserine Lactone Isoforms A comparison of anti-microbial activity between chemically and recombinantly synthesized cationic peptide was carried out.

The antimicrobial activities of the chemically synthesized MBI-11B7CN peptide and recombinant DNA synthesized MBI-11B7HSL (homoserine lactone form) and MBI-11B7HS (homoserine form) peptides were tested against various gram-negative and positive strains of bacteria, including antibiotic resistant strains. The Agarose Dilution Assay was performed as described in "Methods for Dilution Antimicrobial Susceptibility Tests for Bacteria That Grow Aerobically-Fourth Edition; Approved Standard" NCCLS document M7-A4 (ISBN 1-56238-309-4) Vol. 17, No 2 (1977).

The agarose dilution assay measures antimicrobial activity of peptides and peptide analogues, which is expressed as the minimum inhibitory concentration (MIC) of the peptides.

In order to mimic in vivo conditions, calcium and magnesium supplemented Mueller Hinton broth is used in combination with a low EEO agarose as the bacterial growth medium. Agarose, rather than agar, is used as the charged groups in agar prevent peptide diffusion through the media. The medium is autoclaved and then cooled to 50° C.–55° C. in a water bath before aseptic addition of anti-microbial solutions. The same volume of different concentrations of peptide solution are added to the cooled molten agarose which is then poured to a depth of 3–4 mm.

The bacterial inoculum is adjusted to a 0.5 McFarland turbidity standard (PML Microbiological) and then diluted 1:10 before application on to the agarose plate. The final inoculum applied to the agarose is approximately $10^4$ CFU in a 5–8 mm diameter spot. The agarose plates are incubated at 35° C.–37° C. for 16 to 20 hours.

The MIC is recorded as the lowest concentration of peptide that completely inhibits growth of the organism as determined by visual inspection. Representative MICs for the cationic peptides against various bacterial strains are shown in Table 3.

TABLE 3

MINIMUM INHIBITORY CONCENTRATION (MIC) VALUES FOR MBI-11B7CN (CARBOXY-AMIDATED), MBI-11B7HSL (HOMOSERINE LACTONE FORM) AND MBI-11B7HS (HOMOSERINE FORM) PEPTEDES, AGAINST VARIOUS GRAM-NEGATIVE AND GRAM-POSITIVE BACTERIA STRAINS

| | | | MIC (g/ml) | | |
|---|---|---|---|---|---|
| Organism | Organism # | Source | 11B7CN 92A1 | 11B7HSL 293B1 | 11B7HS 203B1 |
| A. calcoaceticus | AC2 | ATCC | 2 | 4 | 2 |
| E. cloacae | ECL7 | ATCC | >64 | >64 | >64 |
| E. coli | ECO5 | ATCC | 8 | 32 | |
| K. pneumoniae | KP1 | ATCC | 8 | 8 | 32 |
| P. aeruginosa | PA4 | ATCC | >64 | >64 | >64 |
| S. maltophilia | SMA2 | ATCC | 32 | 32 | 64 |
| S. marcescens | SMS3 | ATCC | >64 | >64 | >64 |
| E. faecalis | EFS1 | ATCC | 2 | 1 | 2 |
| E. faecalis | EFS8 | ATCC | 16 | 16 | 32 |
| S. aureus | SA14 | Bayer | 4 | 1 | 2 |
| S. aureus | SA93 | Bayer | 1 | 1 | 1 |
| S. epidermidis | SE10 | Chow | 2 | 4 | 8 |

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

We claim:

1. A multi-domain fusion protein expression cassette, comprising a promoter operably linked to a nucleic acid molecule that encodes a fusion protein, wherein the encoded fusion protein comprises a structure of [(cleavage site)-(cationic peptide)-(cleavage site)-(anionic spacer peptide)]$_n$ with n being an integer having a value between 2 and 40, and wherein the cationic peptides have at least 30% tryptophan and have antimicrobial activity.

2. The expression cassette according to claim 1 wherein the promoter is selected from the group consisting of lacP promoter, tacP promoter, trcP promoter, srpP promoter, SP6 promoter, T7 promoter, araP promoter, trpP promoter, and λ promoter.

3. The expression cassette according to claim 1 wherein the anionic spacer has no cysteine residue.

4. The expression cassette according to claim 1 wherein the cumulative charge of the anionic spacer peptide reduces the cumulative charge of the cationic peptide.

5. The expression cassette according to claim 1 wherein n has a value of between 5 and 30.

6. The expression cassette according to claim 1 wherein n has a value of between 10 and 20.

7. The expression cassette according to claim 1 wherein the cationic peptide has up to 35 amino acids comprising the sequence of SEQ ID NO:35 or SEQ ID NO:36.

8. The expression cassette according to claim 1 wherein the cleavage site can be cleaved by low pH or by a reagent selected from cyanogen bromide, N-chlorosuccinimide, 2-(2-nitrophenylsulphenyl)-3-methyl-3'-bromoindolenine, hydroxylamine, o-iodosobenzoic acid, Factor Xa, Factor XIIa, thrombin, enterokinase, collagenase, *Staphylococcus aureus* V8 protease, endoproteinase Glu-C, endoproteinase Arg-C, endoproteinase Lys-C, chymotrypsin, trypsin, or a combination thereof.

9. The expression cassette according to claim 1 wherein the encoded fusion protein further comprises one additional cationic peptide or two additional cationic peptides, wherein the additional peptide or peptides are at the carboxy-terminus of the encoded fusion protein.

10. The expression cassette according to claim 1 or claim 9 wherein the expression cassette is contained in an expression vector.

11. The expression cassette according to claim 1 or claim 9 wherein the cationic peptide is SEQ ID NO:36.

12. The expression cassette according to claim 1 or claim 9 further comprising a carrier amino acid sequence wherein the carrier amino acid sequence is at the amino-terminus of the encoded fusion protein.

13. The expression cassette according to claim 12 wherein the carrier is selected from cellulose binding domain, glutathione-S-transferase, outer membrane protein F, β-galactosidase, protein A, or IgG-binding domain.

14. The expression cassette according to claim 12 wherein the carrier is less than 100 amino acid residues in length.

15. The expression cassette according to claim 14 wherein the carrier is a truncated cellulose binding domain.

16. The expression cassette according to claim 12 wherein the cationic peptide is SEQ ID NO:36.

17. A recombinant host cell comprising the expression cassette according to claim 16 wherein the expression cassette is contained in an expression vector.

18. The recombinant host cell according to claim 17 wherein the encoded fusion protein is expressed as an insoluble protein.

19. A method of producing a fusion protein, comprising culturing a recombinant host cell according to claim 17 under conditions and for a time sufficient to produce said fusion protein.

20. The method according to claim 19 wherein the fusion protein is cleaved at the cleavage sites to release the cationic peptides from the anionic spacers.

21. The method according to claim 20 wherein the fusion protein is cleaved by endoproteinase Lys-C.

22. The method according to claim 20 wherein the released cationic peptides are amidated at the carboxy-terminus.

23. A recombinant host cell comprising the expression cassette according to any one of claims 1, 3, 5, and 6.

24. The recombinant host cell of claim 23 wherein the host cell is a yeast, a fungus, a bacteria or a plant cell.

25. The recombinant host cell of claim 24 wherein the bacteria is *Escherichia coli*.

26. A method of producing a fusion protein, comprising culturing the recombinant host cell of claim 23 under conditions and for a time sufficient to produce the fusion protein.

27. The recombinant host cell of claim 23 wherein the expression cassette is contained in an expression vector.

28. The recombinant host cell according to claim 27 wherein the encoded cationic peptide fusion protein is expressed as an insoluble protein.

29. A method of producing a fusion protein, comprising culturing a recombinant host cell according to claim 28 under conditions and for a time sufficient to produce said fusion protein.

\* \* \* \* \*

UNITED STATES PATENT AND TRADEMARK OFFICE
CERTIFICATE OF CORRECTION

PATENT NO. : 6,946,261 B1
DATED : September 20, 2005
INVENTOR(S) : Jan Burian et al.

It is certified that error appears in the above-identified patent and that said Letters Patent is hereby corrected as shown below:

<u>Title page,</u>
Item [56], References Cited, FOREIGN PATENT DOCUMENTS, delete "6/1902" and insert -- 6/2002 --.
OTHER PUBLICATIONS,
"Stratagene Product Catalog" reference, after "pp" insert -- . --.
"Zhang et al." reference, delete "Catiionic" and insert -- Cationic --.

<u>Column 1,</u>
Line 61, delete "et al", and insert -- et al., --.

<u>Column 2,</u>
Line 13, delete "et at", and insert -- et al., --.
Line 14, delete "et al,", and insert -- et al., --.
Line 14, delete "Acad" and insert -- Acad. --.

<u>Column 4,</u>
Line 23, after "purified" delete "1".

<u>Column 5,</u>
Line 35, delete "1 m/min" and insert -- 1 ml/min --.

<u>Column 8,</u>
Line 46, delete "L" before "3.".

<u>Column 10,</u>
Line 10, delete "antifingal" and insert -- antifungal --.
Lines 20 and 22, Table 1, Col. 3, after "AVATVGQAAAIARG" insert -- * --.
Line 29, Table 1, Col. 3, delete "GIGSAILSAGKSALKGIAKGLAE" and insert
-- GIGSAILSAGKSALKGLAKGLAE --.

<u>Column 13,</u>
Line 4, (Excluding Table 1), after "(1992);" delete "Bulet et al," and insert -- Bulet et al., --; and after "JBC" insert -- 268: --.
Line 13, after "Lambert" delete "er al." and insert -- et al., --.

<u>Column 16,</u>
Line 46, after "Microbiol" insert -- . --.

<u>Column 18,</u>
Line 31, delete "JM105" and insert -- JM101 --.

UNITED STATES PATENT AND TRADEMARK OFFICE
CERTIFICATE OF CORRECTION

PATENT NO. : 6,946,261 B1
DATED : September 20, 2005
INVENTOR(S) : Jan Burian et al.

It is certified that error appears in the above-identified patent and that said Letters Patent is hereby corrected as shown below:

Column 19,
Line 13, delete "SF21(AQTCC CRL 1711)" and insert -- sf9 (ATCC CRL 1711) --.

Column 21,
Line 5, "pET21CBD96x11B7" and insert -- pET21CBD96-2x11B7 --.
Line 50, "MBI-11 B7" and insert -- MBI-11B7 --.

Column 22,
Line 19, delete "65" and insert -- 6S --.

Column 26,
Line 9, delete "pET21 CBD96" and insert -- pET21CBD96 --.
Line 16, after "the" delete "+".
Line 21, after "pmol each of" delete "each of".
Line 22, after delete "(SEQ ID NO:11)" and insert -- (SEQ ID NO:1) --.
Line 49, after "Then" delete "is".
Line 54, delete "250° F." and insert -- 250 μF --.

Column 27,
Line 35, insert -- μl -- before "reactions".
Line 42, delete "2 lμl" and insert -- 2μl --.
Line 52, delete "100 Pg/ml" and insert -- 100 μg/ml --
Line 62, delete "30C" and insert -- 30°C --.

Column 29,
Line 41, delete "pET21 CBD96-11" and insert -- pET21CBD96-11 --.
Line 42, delete "pET21 CBD96-2x11" and insert -- pET21CBD96-2x11 --.

Column 30,
Line 5, delete "pET21 CBD96-10x11" and insert -- pET21CBD96-10x11 --.
Line 14, delete "GGCG" and insert -- GCCG --.
Line 54, delete "11B 7" and insert -- 11B7 --.

Column 31,
Line 7, delete "Avionic" and insert -- Anionic --.
Line 44, delete "11 B7S" and insert -- 11B7S --.

Column 32,
Lines 65-66, delete "100 p g/ml" and insert -- 100 μg/ml --.

UNITED STATES PATENT AND TRADEMARK OFFICE
CERTIFICATE OF CORRECTION

PATENT NO. : 6,946,261 B1
DATED : September 20, 2005
INVENTOR(S) : Jan Burian et al.

It is certified that error appears in the above-identified patent and that said Letters Patent is hereby corrected as shown below:

Column 33,
Line 11, delete "soon" and insert -- so on. --.
Line 22, after "fifteen" delete ".".

Column 34,
Line 8, delete "2µL" and insert -- 2µl --.
Line 27, delete "5S-x11B7" and insert -- 5S-5x11B7 --.
Line 37, delete "Mb126" and insert -- MBI26 --.
Line 48, delete "mbi11 B7" and insert -- mbi11B7 --.
Line 53, delete "MB126" and insert -- MBI26 --.

Column 35,
Line 9, delete "MBI126" and insert -- MBI26 --.
Line 33, after "art" delete ";" and insert -- . --.
Line 37, delete "pTZ18R-026GT" and insert -- pTZ18R-26GT --.

Column 37,
Line 20, delete "MB-11B7" and insert -- MBI-11B7 --.
Line 56, delete "5 mL/min." and insert -- 5 ml/min. --.

Column 38,
Line 43, delete "PEPTEDES" and insert -- PEPTIDES --.
Line 47, Table 3, delete "293B1" and insert -- 203B1 --.
Line 52, Table 3, delete "32" and insert -- 8 --.
Line 52, Table 3, below ">64" insert -- 32 --.

Signed and Sealed this

Twenty-first Day of March, 2006

JON W. DUDAS
*Director of the United States Patent and Trademark Office*

SEQUENCE LISTING

<160> NUMBER OF SEQ ID NOS: 113

<210> SEQ ID NO 1
<211> LENGTH: 20
<212> TYPE: DNA
<213> ORGANISM: Artificial Sequence
<220> FEATURE:
<223> OTHER INFORMATION: Primer for PCR amplification

<400> SEQUENCE: 1
gcgtccggcg tagaggatcg                                              20

<210> SEQ ID NO 2
<211> LENGTH: 25
<212> TYPE: DNA
<213> ORGANISM: Artificial Sequence
<220> FEATURE:
<223> OTHER INFORMATION: Primer for PCR amplification

<400> SEQUENCE: 2
ccgggatcca atgttgcaga agtag                                        25

<210> SEQ ID NO 3
<211> LENGTH: 20
<212> TYPE: DNA
<213> ORGANISM: Artificial Sequence
<220> FEATURE:
<223> OTHER INFORMATION: Primer for PCR amplification

<400> SEQUENCE: 3
gcgtccggcg tagaggatcg                                              20

<210> SEQ ID NO 4
<211> LENGTH: 38
<212> TYPE: DNA
<213> ORGANISM: Artificial Sequence
<220> FEATURE:
<223> OTHER INFORMATION: Primer for PCR amplification

<400> SEQUENCE: 4
atatggatcc agatatgtat cataggttga tgttgggc                          38

<210> SEQ ID NO 5
<211> LENGTH: 39
<212> TYPE: DNA
<213> ORGANISM: Artificial Sequence
<220> FEATURE:
<223> OTHER INFORMATION: Synthesized oligonucleotide used as template
      for PCR

<400> SEQUENCE: 5
tttaacgggg atccgtctca tatgatcctg aaaaaatgg                         39

<210> SEQ ID NO 6
<211> LENGTH: 49
<212> TYPE: DNA
<213> ORGANISM: Artificial Sequence
<220> FEATURE:
<223> OTHER INFORMATION: Synthesized Oligonucleotide used as a template
      for PCR

<400> SEQUENCE: 6
ccgtggtggc cgtggcgtcg taaataagct tgatatcttg gtacctgcg              49

```
<210> SEQ ID NO 7
<211> LENGTH: 24
<212> TYPE: DNA
<213> ORGANISM: Artificial Sequence
<220> FEATURE:
<223> OTHER INFORMATION: Primer for PCR amplification

<400> SEQUENCE: 7 tttaacggggg atccgtctca tatg                                           24

<210> SEQ ID NO 8
<211> LENGTH: 25
<212> TYPE: DNA
<213> ORGANISM: Artificial Sequence
<220> FEATURE:
<223> OTHER INFORMATION: Primer for PCR amplification

<400> SEQUENCE: 8
taagcttgat atcttggtac ctgcg                                           25

<210> SEQ ID NO 9
<211> LENGTH: 24
<212> TYPE: DNA
<213> ORGANISM: Artificial Sequence
<220> FEATURE:
<223> OTHER INFORMATION: Primer used for PCR modification of DNA
      fragment encoding MBI-11

<400> SEQUENCE: 9 tttaacggggg atccgtctca tatg                                           24

<210> SEQ ID NO 10
<211> LENGTH: 48
<212> TYPE: DNA
<213> ORGANISM: Artificial Sequence
<220> FEATURE:
<223> OTHER INFORMATION: Primer used for PCR modification of DNA
      fragment encoding MBI-11

<400> SEQUENCE: 10
cgcgaagctt aataatacat aattttacga cgccacggcc accacggc                  48

<210> SEQ ID NO 11
<211> LENGTH: 114
<212> TYPE: DNA
<213> ORGANISM: Artificial Sequence
<220> FEATURE:
<223> OTHER INFORMATION: Synthesized oligonucleotide used as a template
      for PCR

<400> SEQUENCE: 11
cgccagggtt tccccagtca cgacggatcc gtctcatatg atcctgaaaa aatggccgtg     60
gtggccgtgg cgtcgtaaaa ttaattgaat tcgtcatagc tgtttcctgt gtga          114

<210> SEQ ID NO 12
<211> LENGTH: 24
<212> TYPE: DNA
<213> ORGANISM: Artificial Sequence
<220> FEATURE:
<223> OTHER INFORMATION: Primer for PCR amplification

<400> SEQUENCE: 12
cgccagggtt tccccagtca cgac                                            24

<210> SEQ ID NO 13
<211> LENGTH: 22
```

```
<212> TYPE: DNA
<213> ORGANISM: Artificial Sequence
<220> FEATURE:
<223> OTHER INFORMATION: Primer for PCR amplification

<400> SEQUENCE: 13
tcacacagga aacagctatg ac                                              22

<210> SEQ ID NO 14
<211> LENGTH: 151
<212> TYPE: DNA
<213> ORGANISM: Artificial Sequence
<220> FEATURE:
<223> OTHER INFORMATION: Synthesized oligonucleotide used as a template
      for PCR

<400> SEQUENCE: 14
cgccagggtt ttcccagtca cgacggatcc gtctcatatg attctgcgtt ggccgtggtg     60
gccgtggcgt cgcaaaatga ttctgcgttg gccgtggtgg ccgtggcgtc gcaaaatggc    120
ggcctaagct tcgatcctct acgccggacg c                                   151

<210> SEQ ID NO 15
<211> LENGTH: 24
<212> TYPE: DNA
<213> ORGANISM: Artificial Sequence
<220> FEATURE:
<223> OTHER INFORMATION: Primer for PCR amplification

<400> SEQUENCE: 15
cgccagggtt ttcccagtca cgac                                            24

<210> SEQ ID NO 16
<211> LENGTH: 20
<212> TYPE: DNA
<213> ORGANISM: Artificial Sequence
<220> FEATURE:
<223> OTHER INFORMATION: Primer for PCR amplification

<400> SEQUENCE: 16
gcgtccggcg tagaggatcg                                                 20

<210> SEQ ID NO 17
<211> LENGTH: 108
<212> TYPE: DNA
<213> ORGANISM: Artificial Sequence
<220> FEATURE:
<223> OTHER INFORMATION: Synthesized oligonucleotide us as a template
      for PCR

<400> SEQUENCE: 17
cgccagggtt ttcccagtca cgacggatcc gtctcatatg attctgcgtt ggccgtggtg     60
gccgtggcgt cgcaaaatgc ataagcttcg atcctctacg ccggacgc                 108

<210> SEQ ID NO 18
<211> LENGTH: 24
<212> TYPE: DNA
<213> ORGANISM: Artificial Sequence
<220> FEATURE:
<223> OTHER INFORMATION: Primer for PCR amplification

<400> SEQUENCE: 18
cgccagggtt ttcccagtca cgac                                            24

<210> SEQ ID NO 19
```

```
<211> LENGTH: 20
<212> TYPE: DNA
<213> ORGANISM: Artificial Sequence
<220> FEATURE:
<223> OTHER INFORMATION: Primer for PCR amplification

<400> SEQUENCE: 19
gcgtccggcg tagaggatcg                                                   20

<210> SEQ ID NO 20
<211> LENGTH: 97
<212> TYPE: DNA
<213> ORGANISM: Artificial Sequence
<220> FEATURE:
<223> OTHER INFORMATION: Synthesized oligonucleotide used as a template
      for PCR

<400> SEQUENCE: 20
cgccagggtt ttcccagtca cgacggatcc gtctatgcat gaagcggaac cggaagcgga       60
accgattaat taagcttcga tcctctacgc cggacgc                                97

<210> SEQ ID NO 21
<211> LENGTH: 24
<212> TYPE: DNA
<213> ORGANISM: Artificial Sequence
<220> FEATURE:
<223> OTHER INFORMATION: Primer for PCR amplification

<400> SEQUENCE: 21
cgccagggtt ttcccagtca cgac                                              24

<210> SEQ ID NO 22
<211> LENGTH: 20
<212> TYPE: DNA
<213> ORGANISM: Artificial Sequence
<220> FEATURE:
<223> OTHER INFORMATION: Primer for PCR amplification

<400> SEQUENCE: 22
gcgtccggcg tagaggatcg                                                   20

<210> SEQ ID NO 23
<211> LENGTH: 114
<212> TYPE: DNA
<213> ORGANISM: Artificial Sequence
<220> FEATURE:
<223> OTHER INFORMATION: Synthesized oligonucleotide used as a template
      for PCR

<400> SEQUENCE: 23
cgccagggtt ttcccagtca cgacggatcc gtctcatatg actatgattc tgcgttggcc       60
gtggtggccg tggcgtcgca aaatgcataa gcttcgatcc tctacgccgg acgc            114

<210> SEQ ID NO 24
<211> LENGTH: 24
<212> TYPE: DNA
<213> ORGANISM: Artificial Sequence
<220> FEATURE:
<223> OTHER INFORMATION: Primer for PCR amplification

<400> SEQUENCE: 24
cgccagggtt ttcccagtca cgac                                              24

<210> SEQ ID NO 25
<211> LENGTH: 20
```

```
<212> TYPE: DNA
<213> ORGANISM: Artificial Sequence
<220> FEATURE:
<223> OTHER INFORMATION: Primer for PCR amplification

<400> SEQUENCE: 25
gcgtccggcg tagaggatcg                                              20

<210> SEQ ID NO 26
<211> LENGTH: 157
<212> TYPE: DNA
<213> ORGANISM: Artificial Sequence
<220> FEATURE:
<223> OTHER INFORMATION: Synthesized oligonucleotide used as a template
      for PCR

<400> SEQUENCE: 26
cgccagggtt tcccagtca cgacggatcc gtctcatatg accatgaaat ggaaatcttt   60
catcaaaaaa ctgacctctg ctgctaaaaa agttgttacc accgctaaac cgctgatctc  120
tatgcatgct taagcttcga tcctctacgc cggacgc                          157

<210> SEQ ID NO 27
<211> LENGTH: 11
<212> TYPE: PRT
<213> ORGANISM: Apis mellifera
<220> FEATURE:
<223> OTHER INFORMATION: Anionic spacer peptide

<400> SEQUENCE: 27

His Glu Ala Glu Pro Glu Ala Glu Pro Ile Met
 1               5                  10

<210> SEQ ID NO 28
<211> LENGTH: 8
<212> TYPE: PRT
<213> ORGANISM: Apis mellifera

<400> SEQUENCE: 28

Glu Ala Glu Pro Glu Ala Glu Pro
 1               5

<210> SEQ ID NO 29
<211> LENGTH: 8
<212> TYPE: PRT
<213> ORGANISM: Apis mellifera

<400> SEQUENCE: 29

Glu Ala Lys Pro Glu Ala Glu Pro
 1               5

<210> SEQ ID NO 30
<211> LENGTH: 8
<212> TYPE: PRT
<213> ORGANISM: Apis mellifera

<400> SEQUENCE: 30

Glu Ala Glu Pro Lys Ala Glu Pro
 1               5

<210> SEQ ID NO 31
<211> LENGTH: 8
<212> TYPE: PRT
<213> ORGANISM: Apis mellifera

<400> SEQUENCE: 31
```

-continued

```
Glu Ala Glu Ser Glu Ala Glu Pro
 1               5
```

<210> SEQ ID NO 32
<211> LENGTH: 8
<212> TYPE: PRT
<213> ORGANISM: Apis mellifera

<400> SEQUENCE: 32

```
Glu Ala Glu Leu Glu Ala Glu Pro
 1               5
```

<210> SEQ ID NO 33
<211> LENGTH: 6
<212> TYPE: PRT
<213> ORGANISM: Apis mellifera

<400> SEQUENCE: 33

```
Glu Pro Glu Ala Glu Pro
 1               5
```

<210> SEQ ID NO 34
<211> LENGTH: 4
<212> TYPE: PRT
<213> ORGANISM: Apis mellifera

<400> SEQUENCE: 34

```
Glu Ala Glu Pro
 1
```

<210> SEQ ID NO 35
<211> LENGTH: 13
<212> TYPE: PRT
<213> ORGANISM: Artificial Sequence
<220> FEATURE:
<223> OTHER INFORMATION: Modified indolicidin cationic peptide

<400> SEQUENCE: 35

```
Ile Leu Lys Lys Trp Pro Trp Trp Pro Trp Arg Arg Lys
 1               5                  10
```

<210> SEQ ID NO 36
<211> LENGTH: 12
<212> TYPE: PRT
<213> ORGANISM: Artificial Sequence
<220> FEATURE:
<223> OTHER INFORMATION: Modified indolicidin cationic peptide

<400> SEQUENCE: 36

```
Ile Leu Arg Trp Pro Trp Trp Pro Trp Arg Arg Lys
 1               5                  10
```

<210> SEQ ID NO 37
<211> LENGTH: 34
<212> TYPE: PRT
<213> ORGANISM: Apis mellifera

<400> SEQUENCE: 37

```
Tyr Val Pro Leu Pro Asn Val Pro Gln Pro Gly Arg Arg Pro Phe Pro
 1               5                  10                  15
Thr Phe Pro Gly Gln Gly Pro Phe Asn Pro Lys Ile Lys Trp Pro Gln
                20                  25                  30
Gly Tyr
```

-continued

<210> SEQ ID NO 38
<211> LENGTH: 34
<212> TYPE: PRT
<213> ORGANISM: Drosophila melanogaster

<400> SEQUENCE: 38

Val Phe Ile Asp Ile Leu Asp Lys Val Glu Asn Ala Ile His Asn Ala
1               5                   10                  15

Ala Gln Val Gly Ile Gly Phe Ala Lys Pro Phe Glu Lys Leu Ile Asn
            20                  25                  30

Pro Lys

<210> SEQ ID NO 39
<211> LENGTH: 18
<212> TYPE: PRT
<213> ORGANISM: Apis mellifera

<400> SEQUENCE: 39

Gly Asn Asn Arg Pro Val Tyr Ile Pro Gln Pro Arg Pro Pro His Pro
1               5                   10                  15

Arg Ile

<210> SEQ ID NO 40
<211> LENGTH: 18
<212> TYPE: PRT
<213> ORGANISM: Apis mellifera

<400> SEQUENCE: 40

Gly Asn Asn Arg Pro Val Tyr Ile Pro Gln Pro Arg Pro Pro His Pro
1               5                   10                  15

Arg Leu

<210> SEQ ID NO 41
<211> LENGTH: 18
<212> TYPE: PRT
<213> ORGANISM: Apis mellifera

<400> SEQUENCE: 41

Gly Asn Asn Arg Pro Ile Tyr Ile Pro Gln Pro Arg Pro Pro His Pro
1               5                   10                  15

Arg Leu

<210> SEQ ID NO 42
<211> LENGTH: 12
<212> TYPE: PRT
<213> ORGANISM: Bos taurus

<400> SEQUENCE: 42

Arg Leu Cys Arg Ile Val Val Ile Arg Val Cys Arg
1               5                   10

<210> SEQ ID NO 43
<211> LENGTH: 42
<212> TYPE: PRT
<213> ORGANISM: Bos taurus

<400> SEQUENCE: 43

Arg Phe Arg Pro Pro Ile Arg Arg Pro Pro Ile Arg Pro Pro Phe Tyr
1               5                   10                  15

Pro Pro Phe Arg Pro Pro Ile Arg Pro Pro Ile Phe Pro Pro Ile Arg
            20                  25                  30

```
Pro Pro Phe Arg Pro Pro Leu Arg Phe Pro
        35                  40
```

<210> SEQ ID NO 44
<211> LENGTH: 59
<212> TYPE: PRT
<213> ORGANISM: Bos taurus

<400> SEQUENCE: 44

```
Arg Arg Ile Arg Pro Arg Pro Arg Leu Pro Arg Pro Arg Pro Arg
  1               5                  10                  15

Pro Leu Pro Phe Pro Arg Pro Gly Pro Arg Pro Ile Pro Arg Pro Leu
                20                  25                  30

Pro Phe Pro Arg Pro Gly Pro Arg Pro Ile Pro Arg Pro Leu Pro Phe
            35                  40                  45

Pro Arg Pro Gly Pro Arg Pro Ile Pro Arg Pro
         50                  55
```

<210> SEQ ID NO 45
<211> LENGTH: 37
<212> TYPE: PRT
<213> ORGANISM: Manduca sexta

<400> SEQUENCE: 45

```
Trp Asn Pro Phe Lys Glu Leu Glu Arg Ala Gly Gln Arg Val Arg Asp
  1               5                  10                  15

Ala Val Ile Ser Ala Ala Pro Val Ala Thr Val Gly Gln Ala Ala
                20                  25                  30

Ala Ile Ala Arg Gly
         35
```

<210> SEQ ID NO 46
<211> LENGTH: 37
<212> TYPE: PRT
<213> ORGANISM: Manduca sexta

<400> SEQUENCE: 46

```
Trp Asn Pro Phe Lys Glu Leu Glu Arg Ala Gly Gln Arg Val Arg Asp
  1               5                  10                  15

Ala Ile Ile Ser Ala Gly Pro Val Ala Thr Val Gly Gln Ala Ala
                20                  25                  30

Ala Ile Ala Arg Gly
         35
```

<210> SEQ ID NO 47
<211> LENGTH: 37
<212> TYPE: PRT
<213> ORGANISM: Manduca sexta

<400> SEQUENCE: 47

```
Trp Asn Pro Phe Lys Glu Leu Glu Arg Ala Gly Gln Arg Val Arg Asp
  1               5                  10                  15

Ala Ile Ile Ser Ala Ala Pro Val Ala Thr Val Gly Gln Ala Ala
                20                  25                  30

Ala Ile Ala Arg Gly
         35
```

<210> SEQ ID NO 48
<211> LENGTH: 37
<212> TYPE: PRT

<213> ORGANISM: Manduca sexta

<400> SEQUENCE: 48

Trp Asn Pro Phe Lys Glu Leu Glu Arg Ala Gly Gln Arg Val Arg Asp
1               5                   10                  15

Ala Val Ile Ser Ala Ala Val Ala Thr Val Gly Gln Ala Ala Ala
            20                  25                  30

Ile Ala Arg Gly Gly
        35

<210> SEQ ID NO 49
<211> LENGTH: 24
<212> TYPE: PRT
<213> ORGANISM: Bombina variegata

<400> SEQUENCE: 49

Gly Ile Gly Ala Leu Ser Ala Lys Gly Ala Leu Lys Gly Leu Ala Lys
1               5                   10                  15

Gly Leu Ala Glx His Phe Ala Asn
            20

<210> SEQ ID NO 50
<211> LENGTH: 27
<212> TYPE: PRT
<213> ORGANISM: Bombina orientalis

<400> SEQUENCE: 50

Gly Ile Gly Ala Ser Ile Leu Ser Ala Gly Lys Ser Ala Leu Lys Gly
1               5                   10                  15

Leu Ala Lys Gly Leu Ala Glu His Phe Ala Asn
            20                  25

<210> SEQ ID NO 51
<211> LENGTH: 27
<212> TYPE: PRT
<213> ORGANISM: Bombina orientalis

<400> SEQUENCE: 51

Gly Ile Gly Ser Ala Ile Leu Ser Ala Gly Lys Ser Ala Leu Lys Gly
1               5                   10                  15

Leu Ala Lys Gly Leu Ala Glu His Phe Ala Asn
            20                  25

<210> SEQ ID NO 52
<211> LENGTH: 17
<212> TYPE: PRT
<213> ORGANISM: Megabombus pennsylvanicus

<400> SEQUENCE: 52

Ile Lys Ile Thr Thr Met Leu Ala Lys Leu Gly Lys Val Leu Ala His
1               5                   10                  15

Val

<210> SEQ ID NO 53
<211> LENGTH: 17
<212> TYPE: PRT
<213> ORGANISM: Megabombus pennsylvanicus

<400> SEQUENCE: 53

Ser Lys Ile Thr Asp Ile Leu Ala Lys Leu Gly Lys Val Leu Ala His
1               5                   10                  15

Val

<210> SEQ ID NO 54
<211> LENGTH: 58
<212> TYPE: PRT
<213> ORGANISM: Bos taurus

<400> SEQUENCE: 54

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 55
<211> LENGTH: 24
<212> TYPE: PRT
<213> ORGANISM: Rana esculenta

<400> SEQUENCE: 55

Phe Leu Pro Leu Leu Ala Gly Leu Ala Ala Asn Phe Leu Pro Lys Ile
1               5                   10                  15

Phe Cys Lys Ile Thr Arg Lys Cys
            20

<210> SEQ ID NO 56
<211> LENGTH: 33
<212> TYPE: PRT
<213> ORGANISM: Rana esculenta

<400> SEQUENCE: 56

Gly Ile Met Asp Thr Leu Lys Asn Leu Ala Lys Thr Ala Gly Lys Gly
1               5                   10                  15

Ala Leu Gln Ser Leu Leu Asn Lys Ala Ser Cys Lys Leu Ser Gly Gln
            20                  25                  30

Cys

<210> SEQ ID NO 57
<211> LENGTH: 37
<212> TYPE: PRT
<213> ORGANISM: Hyalophora cecropia

<400> SEQUENCE: 57

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 58
<211> LENGTH: 35
<212> TYPE: PRT
<213> ORGANISM: Hyalophora cecropia

<400> SEQUENCE: 58

Lys Trp Lys Val Phe Lys Lys Ile Glu Lys Met Gly Arg Asn Ile Arg
1               5                   10                  15

Asn Gly Ile Val Lys Ala Gly Pro Ala Ile Ala Val Leu Gly Glu Ala
            20                  25                  30

Lys Ala Leu
        35

<210> SEQ ID NO 59
<211> LENGTH: 40
<212> TYPE: PRT
<213> ORGANISM: Drosophila melanogaster

<400> SEQUENCE: 59

Gly Trp Leu Lys Lys Leu Gly Lys Arg Ile Glu Arg Ile Gly Gln His
 1               5                  10                  15

Thr Arg Asp Ala Thr Ile Gln Gly Leu Gly Ile Ala Gln Gln Ala Ala
            20                  25                  30

Asn Val Ala Ala Thr Ala Arg Gly
            35                  40

<210> SEQ ID NO 60
<211> LENGTH: 36
<212> TYPE: PRT
<213> ORGANISM: Hyalophora cecropia

<400> SEQUENCE: 60

Trp Asn Pro Phe Lys Glu Leu Glu Lys Val Gly Gln Arg Val Arg Asp
 1               5                  10                  15

Ala Val Ile Ser Ala Gly Pro Ala Val Ala Thr Val Ala Gln Ala Thr
            20                  25                  30

Ala Leu Ala Lys
        35

<210> SEQ ID NO 61
<211> LENGTH: 31
<212> TYPE: PRT
<213> ORGANISM: Sus scrofa

<400> SEQUENCE: 61

Ser Trp Leu Ser Lys Thr Ala Lys Lys Leu Glu Asn Ser Ala Lys Lys
 1               5                  10                  15

Arg Ile Ser Glu Gly Ile Ala Ile Ala Ile Gln Gly Gly Pro Arg
            20                  25                  30

<210> SEQ ID NO 62
<211> LENGTH: 37
<212> TYPE: PRT
<213> ORGANISM: Leiurus quin-questriatus hebraeus

<400> SEQUENCE: 62

Glx Phe Thr Asn Val Ser Cys Thr Thr Ser Lys Glu Cys Trp Ser Val
 1               5                  10                  15

Cys Gln Arg Leu His Asn Thr Ser Arg Gly Lys Cys Met Asn Lys Lys
            20                  25                  30

Cys Arg Cys Tyr Ser
        35

<210> SEQ ID NO 63
<211> LENGTH: 13
<212> TYPE: PRT
<213> ORGANISM: Vespa crabo

<400> SEQUENCE: 63

```
Phe Leu Pro Leu Ile Leu Arg Lys Ile Val Thr Ala Leu
 1               5                  10
```

<210> SEQ ID NO 64
<211> LENGTH: 35
<212> TYPE: PRT
<213> ORGANISM: Mus musculus

<400> SEQUENCE: 64

```
Leu Arg Asp Leu Val Cys Tyr Cys Arg Ser Arg Gly Cys Lys Gly Arg
 1               5                  10                  15

Glu Arg Met Asn Gly Thr Cys Arg Lys Gly His Leu Leu Tyr Thr Leu
            20                  25                  30

Cys Cys Arg
        35
```

<210> SEQ ID NO 65
<211> LENGTH: 35
<212> TYPE: PRT
<213> ORGANISM: Mus musculus

<400> SEQUENCE: 65

```
Leu Arg Asp Leu Val Cys Tyr Cys Arg Thr Arg Gly Cys Lys Arg Arg
 1               5                  10                  15

Glu Arg Met Asn Gly Thr Cys Arg Lys Gly His Leu Met Tyr Thr Leu
            20                  25                  30

Cys Cys Arg
        35
```

<210> SEQ ID NO 66
<211> LENGTH: 33
<212> TYPE: PRT
<213> ORGANISM: Oryctolagus cuniculus

<400> SEQUENCE: 66

```
Val Val Cys Ala Cys Arg Arg Ala Leu Cys Leu Pro Arg Glu Arg Arg
 1               5                  10                  15

Ala Gly Phe Cys Arg Ile Arg Gly Arg Ile His Pro Leu Cys Cys Arg
            20                  25                  30

Arg
```

<210> SEQ ID NO 67
<211> LENGTH: 33
<212> TYPE: PRT
<213> ORGANISM: Oryctolagus cuniculus

<400> SEQUENCE: 67

```
Val Val Cys Ala Cys Arg Arg Ala Leu Cys Leu Pro Leu Glu Arg Arg
 1               5                  10                  15

Ala Gly Phe Cys Arg Ile Arg Gly Arg Ile His Pro Leu Cys Cys Arg
            20                  25                  30

Arg
```

<210> SEQ ID NO 68
<211> LENGTH: 31
<212> TYPE: PRT
<213> ORGANISM: Cavia cutteri

<400> SEQUENCE: 68

```
Arg Arg Cys Ile Cys Thr Thr Arg Thr Cys Arg Phe Pro Tyr Arg Arg
```

```
                    1               5               10              15
              Leu Gly Thr Cys Ile Phe Gln Asn Arg Val Tyr Thr Phe Cys Cys
                              20              25              30

<210> SEQ ID NO 69
<211> LENGTH: 31
<212> TYPE: PRT
<213> ORGANISM: Cavia cutteri

<400> SEQUENCE: 69

Arg Arg Cys Ile Cys Thr Thr Arg Thr Cys Arg Phe Pro Tyr Arg Arg
               1               5               10              15
              Leu Gly Thr Cys Leu Phe Gln Asn Arg Val Tyr Thr Phe Cys Cys
                              20              25              30

<210> SEQ ID NO 70
<211> LENGTH: 30
<212> TYPE: PRT
<213> ORGANISM: Homo Sapien

<400> SEQUENCE: 70

Ala Cys Tyr Cys Arg Ile Pro Ala Cys Ile Ala Gly Glu Arg Arg Tyr
               1               5               10              15
              Gly Thr Cys Ile Tyr Gln Gly Arg Leu Trp Ala Phe Cys Cys
                              20              25              30

<210> SEQ ID NO 71
<211> LENGTH: 29
<212> TYPE: PRT
<213> ORGANISM: Homo Sapien

<400> SEQUENCE: 71

Cys Tyr Cys Arg Ile Pro Ala Cys Ile Ala Gly Glu Arg Arg Tyr Gly
               1               5               10              15
              Thr Cys Ile Tyr Gln Gly Arg Leu Trp Ala Phe Cys Cys
                              20              25

<210> SEQ ID NO 72
<211> LENGTH: 33
<212> TYPE: PRT
<213> ORGANISM: Oryctolagus cuniculus

<400> SEQUENCE: 72

Val Val Cys Ala Cys Arg Arg Ala Leu Cys Leu Pro Arg Glu Arg Arg
               1               5               10              15
              Ala Gly Phe Cys Arg Ile Arg Gly Arg Ile His Pro Leu Cys Cys Arg
                              20              25              30
              Arg

<210> SEQ ID NO 73
<211> LENGTH: 33
<212> TYPE: PRT
<213> ORGANISM: Oryctolagus cuniculus

<400> SEQUENCE: 73

Val Val Cys Ala Cys Arg Arg Ala Leu Cys Leu Pro Leu Glu Arg Arg
               1               5               10              15
              Ala Gly Phe Cys Arg Ile Arg Gly Arg Ile His Pro Leu Cys Cys Arg
                              20              25              30
              Arg
```

```
<210> SEQ ID NO 74
<211> LENGTH: 32
<212> TYPE: PRT
<213> ORGANISM: Rattus norvegicus

<400> SEQUENCE: 74

Val Thr Cys Tyr Cys Arg Arg Thr Arg Cys Gly Phe Arg Glu Arg Leu
 1               5                  10                  15

Ser Gly Ala Cys Gly Tyr Arg Gly Arg Ile Tyr Arg Leu Cys Cys Arg
            20                  25                  30

<210> SEQ ID NO 75
<211> LENGTH: 32
<212> TYPE: PRT
<213> ORGANISM: Rattus norvegicus

<400> SEQUENCE: 75

Val Thr Cys Tyr Cys Arg Ser Thr Arg Cys Gly Phe Arg Glu Arg Leu
 1               5                  10                  15

Ser Gly Ala Cys Gly Tyr Arg Gly Arg Ile Tyr Arg Leu Cys Cys Arg
            20                  25                  30

<210> SEQ ID NO 76
<211> LENGTH: 38
<212> TYPE: PRT
<213> ORGANISM: Bos taurus

<400> SEQUENCE: 76

Asp Phe Ala Ser Cys His Thr Asn Gly Gly Ile Cys Leu Pro Asn Arg
 1               5                  10                  15

Cys Pro Gly His Met Ile Gln Ile Gly Ile Cys Phe Arg Pro Arg Val
            20                  25                  30

Lys Cys Cys Arg Ser Trp
        35

<210> SEQ ID NO 77
<211> LENGTH: 40
<212> TYPE: PRT
<213> ORGANISM: Bos taurus

<400> SEQUENCE: 77

Val Arg Asn His Val Thr Cys Arg Ile Asn Arg Gly Phe Cys Val Pro
 1               5                  10                  15

Ile Arg Cys Pro Gly Arg Thr Arg Gln Ile Gly Thr Cys Phe Gly Pro
            20                  25                  30

Arg Ile Lys Cys Cys Arg Ser Trp
        35                  40

<210> SEQ ID NO 78
<211> LENGTH: 38
<212> TYPE: PRT
<213> ORGANISM: Bos taurus

<400> SEQUENCE: 78

Asn Pro Val Ser Cys Val Arg Asn Lys Gly Ile Cys Val Pro Ile Arg
 1               5                  10                  15

Cys Pro Gly Ser Met Lys Gln Ile Gly Thr Cys Val Gly Arg Ala Val
            20                  25                  30

Lys Cys Cys Arg Lys Lys
        35
```

```
<210> SEQ ID NO 79
<211> LENGTH: 40
<212> TYPE: PRT
<213> ORGANISM: Sacrophaga peregrina

<400> SEQUENCE: 79

Ala Thr Cys Asp Leu Leu Ser Gly Thr Gly Ile Asn His Ser Ala Cys
 1               5                  10                  15

Ala Ala His Cys Leu Leu Arg Gly Asn Arg Gly Gly Tyr Cys Asn Gly
            20                  25                  30

Lys Ala Val Cys Val Cys Arg Asn
        35                  40

<210> SEQ ID NO 80
<211> LENGTH: 38
<212> TYPE: PRT
<213> ORGANISM: Aeschna cyanea

<400> SEQUENCE: 80

Gly Phe Gly Cys Pro Leu Asp Gln Met Gln Cys His Arg His Cys Gln
 1               5                  10                  15

Thr Ile Thr Gly Arg Ser Gly Gly Tyr Cys Ser Gly Pro Leu Lys Leu
            20                  25                  30

Thr Cys Thr Cys Tyr Arg
        35

<210> SEQ ID NO 81
<211> LENGTH: 38
<212> TYPE: PRT
<213> ORGANISM: Leiurus quinquestriatus

<400> SEQUENCE: 81

Gly Phe Gly Cys Pro Leu Asn Gln Gly Ala Cys His Arg His Cys Arg
 1               5                  10                  15

Ser Ile Arg Arg Arg Gly Gly Tyr Cys Ala Gly Phe Phe Lys Gln Thr
            20                  25                  30

Cys Thr Cys Tyr Arg Asn
        35

<210> SEQ ID NO 82
<211> LENGTH: 32
<212> TYPE: PRT
<213> ORGANISM: Phyllomedusa sauvagii

<400> SEQUENCE: 82

Ala Leu Trp Lys Thr Met Leu Lys Lys Leu Gly Thr Met Ala Leu His
 1               5                  10                  15

Ala Gly Lys Ala Ala Leu Gly Ala Ala Asp Thr Ile Ser Gln Thr Gln
            20                  25                  30

<210> SEQ ID NO 83
<211> LENGTH: 19
<212> TYPE: PRT
<213> ORGANISM: Drosophila melanogaster

<400> SEQUENCE: 83

Gly Lys Pro Arg Pro Tyr Ser Pro Arg Pro Thr Ser His Pro Arg Pro
 1               5                  10                  15

Ile Arg Val
```

<210> SEQ ID NO 84
<211> LENGTH: 46
<212> TYPE: PRT
<213> ORGANISM: Rana esculenta

<400> SEQUENCE: 84

Gly Ile Phe Ser Lys Leu Gly Arg Lys Lys Ile Lys Asn Leu Leu Ile
 1               5                  10                  15

Ser Gly Leu Lys Asn Val Gly Lys Glu Val Gly Met Asp Val Val Arg
            20                  25                  30

Thr Gly Ile Asp Ile Ala Gly Cys Lys Ile Lys Gly Glu Cys
        35                  40                  45

<210> SEQ ID NO 85
<211> LENGTH: 13
<212> TYPE: PRT
<213> ORGANISM: Bos taurus

<400> SEQUENCE: 85

Ile Leu Pro Trp Lys Trp Pro Trp Trp Pro Trp Arg Arg
 1               5                  10

<210> SEQ ID NO 86
<211> LENGTH: 25
<212> TYPE: PRT
<213> ORGANISM: Bos taurus

<400> SEQUENCE: 86

Phe Lys Cys Arg Arg Trp Gln Trp Arg Met Lys Lys Leu Gly Ala Pro
 1               5                  10                  15

Ser Ile Thr Cys Val Arg Arg Ala Phe
            20                  25

<210> SEQ ID NO 87
<211> LENGTH: 34
<212> TYPE: PRT
<213> ORGANISM: Lactococcus lactis

<400> SEQUENCE: 87

Ile Thr Ser Ile Ser Leu Cys Thr Pro Gly Cys Lys Thr Gly Ala Leu
 1               5                  10                  15

Met Gly Cys Asn Met Lys Thr Ala Thr Cys His Cys Ser Ile His Val
            20                  25                  30

Ser Lys

<210> SEQ ID NO 88
<211> LENGTH: 34
<212> TYPE: PRT
<213> ORGANISM: Staphylococcus epidermidis

<400> SEQUENCE: 88

Thr Ala Gly Pro Ala Ile Arg Ala Ser Val Lys Gln Cys Gln Lys Thr
 1               5                  10                  15

Leu Lys Ala Thr Arg Leu Phe Thr Val Ser Cys Lys Gly Lys Asn Gly
            20                  25                  30

Cys Lys

<210> SEQ ID NO 89
<211> LENGTH: 56
<212> TYPE: PRT
<213> ORGANISM: Bacillus subtilis -continued

<400> SEQUENCE: 89

Met Ser Lys Phe Asp Asp Phe Asp Leu Asp Val Val Lys Val Ser Lys
1               5                   10                  15

Gln Asp Ser Lys Ile Thr Pro Gln Trp Lys Ser Glu Ser Leu Cys Thr
            20                  25                  30

Pro Gly Cys Val Thr Gly Ala Leu Gln Thr Cys Phe Leu Gln Thr Leu
        35                  40                  45

Thr Cys Asn Cys Lys Ile Ser Lys
    50                  55

<210> SEQ ID NO 90
<211> LENGTH: 37
<212> TYPE: PRT
<213> ORGANISM: Leuconostoc gelidum

<400> SEQUENCE: 90

Lys Tyr Tyr Gly Asn Gly Val His Cys Thr Lys Ser Gly Cys Ser Val
1               5                   10                  15

Asn Trp Gly Glu Ala Phe Ser Ala Gly Val His Arg Leu Ala Asn Gly
            20                  25                  30

Gly Asn Gly Phe Trp
        35

<210> SEQ ID NO 91
<211> LENGTH: 23
<212> TYPE: PRT
<213> ORGANISM: Xenopus laevis

<400> SEQUENCE: 91

Gly Ile Gly Lys Phe Leu His Ser Ala Gly Lys Phe Gly Lys Ala Phe
1               5                   10                  15

Val Gly Glu Ile Met Lys Ser
            20

<210> SEQ ID NO 92
<211> LENGTH: 23
<212> TYPE: PRT
<213> ORGANISM: Xenopus laevis

<400> SEQUENCE: 92

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 93
<211> LENGTH: 21
<212> TYPE: PRT
<213> ORGANISM: Xenopus laevis

<400> SEQUENCE: 93

Gly Met Ala Ser Lys Ala Gly Ala Ile Ala Gly Lys Ile Ala Lys Val
1               5                   10                  15

Ala Leu Lys Ala Leu
            20

<210> SEQ ID NO 94
<211> LENGTH: 24
<212> TYPE: PRT
<213> ORGANISM: Xenopus laevis -continued

```
<400> SEQUENCE: 94

Gly Val Leu Ser Asn Val Ile Gly Tyr Leu Lys Lys Leu Gly Thr Gly
1               5                   10                  15

Ala Leu Asn Ala Val Leu Lys Gln
            20

<210> SEQ ID NO 95
<211> LENGTH: 25
<212> TYPE: PRT
<213> ORGANISM: Xenopus laevis

<400> SEQUENCE: 95

Gly Trp Ala Ser Lys Ile Gly Gln Thr Leu Gly Lys Ile Ala Lys Val
1               5                   10                  15

Gly Leu Lys Glu Leu Ile Gln Pro Lys
            20                  25

<210> SEQ ID NO 96
<211> LENGTH: 14
<212> TYPE: PRT
<213> ORGANISM: Vespula lewisii

<400> SEQUENCE: 96

Ile Asn Leu Lys Ala Leu Ala Ala Leu Ala Lys Lys Ile Leu
1               5                   10

<210> SEQ ID NO 97
<211> LENGTH: 26
<212> TYPE: PRT
<213> ORGANISM: Apis mellifera

<400> SEQUENCE: 97

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 98
<211> LENGTH: 40
<212> TYPE: PRT
<213> ORGANISM: Phormia terronovae

<400> SEQUENCE: 98

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Gly Val Cys Val Cys Arg Asn
        35                  40

<210> SEQ ID NO 99
<211> LENGTH: 39
<212> TYPE: PRT
<213> ORGANISM: Phormia terronovae

<400> SEQUENCE: 99

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Arg
            20                  25                  30

Lys Gly Val Cys Val Arg Asn
```

<210> SEQ ID NO 100
<211> LENGTH: 18
<212> TYPE: PRT
<213> ORGANISM: Limulus polyphemus

<400> SEQUENCE: 100

Arg Arg Trp Cys Phe Arg Val Cys Tyr Arg Gly Phe Cys Tyr Arg Lys
 1               5                  10                  15

Cys Arg

<210> SEQ ID NO 101
<211> LENGTH: 18
<212> TYPE: PRT
<213> ORGANISM: Limulus polyphemus

<400> SEQUENCE: 101

Arg Arg Trp Cys Phe Arg Val Cys Tyr Lys Gly Phe Cys Tyr Arg Lys
 1               5                  10                  15

Cys Arg

<210> SEQ ID NO 102
<211> LENGTH: 18
<212> TYPE: PRT
<213> ORGANISM: Sus scrofa

<400> SEQUENCE: 102

Arg Gly Gly Arg Leu Cys Tyr Cys Arg Arg Arg Phe Cys Val Cys Val
 1               5                  10                  15

Gly Arg

<210> SEQ ID NO 103
<211> LENGTH: 16
<212> TYPE: PRT
<213> ORGANISM: Sus scrofa

<400> SEQUENCE: 103

Arg Gly Gly Arg Leu Cys Tyr Cys Arg Arg Arg Phe Cys Ile Cys Val
 1               5                  10                  15

<210> SEQ ID NO 104
<211> LENGTH: 18
<212> TYPE: PRT
<213> ORGANISM: Sus scrofa

<400> SEQUENCE: 104

Arg Gly Gly Gly Leu Cys Tyr Cys Arg Arg Arg Phe Cys Val Cys Val
 1               5                  10                  15

Gly Arg

<210> SEQ ID NO 105
<211> LENGTH: 51
<212> TYPE: PRT
<213> ORGANISM: Apis mellifera

<400> SEQUENCE: 105

Val Thr Cys Asp Leu Leu Ser Phe Lys Gly Gln Val Asn Asp Ser Ala
 1               5                  10                  15

Cys Ala Ala Asn Cys Leu Ser Leu Gly Lys Ala Gly Gly His Cys Glu
                20                  25                  30

```
Lys Gly Val Cys Ile Cys Arg Lys Thr Ser Phe Lys Asp Leu Trp Asp
         35                  40                  45
Lys Tyr Phe
     50

<210> SEQ ID NO 106
<211> LENGTH: 39
<212> TYPE: PRT
<213> ORGANISM: Sacrophaga peregrina

<400> SEQUENCE: 106

Gly Trp Leu Lys Lys Ile Gly Lys Lys Ile Glu Arg Val Gly Gln His
 1               5                  10                  15

Thr Arg Asp Ala Thr Ile Gln Gly Leu Gly Ile Ala Gln Gln Ala Ala
             20                  25                  30

Asn Val Ala Ala Thr Ala Arg
         35

<210> SEQ ID NO 107
<211> LENGTH: 39
<212> TYPE: PRT
<213> ORGANISM: Sacrophaga peregrina

<400> SEQUENCE: 107

Gly Trp Leu Lys Lys Ile Gly Lys Lys Ile Glu Arg Val Gly Gln His
 1               5                  10                  15

Thr Arg Asp Ala Thr Ile Gln Val Ile Gly Val Ala Gln Gln Ala Ala
             20                  25                  30

Asn Val Ala Ala Thr Ala Arg
         35

<210> SEQ ID NO 108
<211> LENGTH: 47
<212> TYPE: PRT
<213> ORGANISM: Bos taurus

<400> SEQUENCE: 108

Ser Asp Glu Lys Ala Ser Pro Asp Lys His His Arg Phe Ser Leu Ser
 1               5                  10                  15

Arg Tyr Ala Lys Leu Ala Asn Arg Leu Ala Asn Pro Lys Leu Leu Glu
             20                  25                  30

Thr Phe Leu Ser Lys Trp Ile Gly Asp Arg Gly Asn Arg Ser Val
         35                  40                  45

<210> SEQ ID NO 109
<211> LENGTH: 17
<212> TYPE: PRT
<213> ORGANISM: Tachypleus tridentatus

<400> SEQUENCE: 109

Lys Trp Cys Phe Arg Val Cys Tyr Arg Gly Ile Cys Tyr Arg Arg Cys
 1               5                  10                  15

Arg

<210> SEQ ID NO 110
<211> LENGTH: 17
<212> TYPE: PRT
<213> ORGANISM: Tachypleus tridentatus

<400> SEQUENCE: 110

Arg Trp Cys Phe Arg Val Cys Tyr Arg Gly Ile Cys Tyr Arg Lys Cys
```

```
                1               5                  10                 15
Arg

<210> SEQ ID NO 111
<211> LENGTH: 46
<212> TYPE: PRT
<213> ORGANISM: Hordeum vulgare

<400> SEQUENCE: 111

Lys Ser Cys Cys Lys Asp Thr Leu Ala Arg Asn Cys Tyr Asn Thr Cys
  1               5                  10                 15

Arg Phe Ala Gly Gly Ser Arg Pro Val Cys Ala Gly Ala Cys Arg Cys
             20                  25                 30

Lys Ile Ile Ser Gly Pro Lys Cys Pro Ser Asp Tyr Pro Lys
         35                  40                 45

<210> SEQ ID NO 112
<211> LENGTH: 23
<212> TYPE: PRT
<213> ORGANISM: Trimeresurus wagleri

<400> SEQUENCE: 112

Gly Gly Lys Pro Asp Leu Arg Pro Cys Ile Ile Pro Pro Cys His Tyr
  1               5                  10                 15

Ile Pro Arg Pro Lys Pro Arg
             20

<210> SEQ ID NO 113
<211> LENGTH: 63
<212> TYPE: PRT
<213> ORGANISM: Androctonus australis hector

<400> SEQUENCE: 113

Val Lys Asp Gly Tyr Ile Val Asp Asp Val Asn Cys Thr Tyr Phe Cys
  1               5                  10                 15

Gly Arg Asn Ala Tyr Cys Asn Glu Glu Cys Thr Lys Leu Lys Gly Glu
             20                  25                 30

Ser Gly Tyr Cys Gln Trp Ala Ser Pro Tyr Gly Asn Ala Cys Tyr Cys
         35                  40                 45

Lys Leu Pro Asp His Val Arg Thr Lys Gly Pro Gly Arg Cys His
         50                  55                 60
```